(12) United States Patent
Wong et al.

(10) Patent No.: US 11,480,391 B2
(45) Date of Patent: Oct. 25, 2022

(54) RECOMBINANT VIRUS, COMPOSITION COMPRISING THE SAME, AND USES THEREOF

(71) Applicant: Academia Sinica, Taipei (TW)

(72) Inventors: Chi-Huey Wong, Rancho Santa Fe, CA (US); Chung-Yi Wu, Taichung (TW)

(73) Assignee: ACADEMIA SINICA, Taipei (TW)

( * ) Notice: Subject to any disclaimer, the term of this patent is extended or adjusted under 35 U.S.C. 154(b) by 3 days.

(21) Appl. No.: 16/348,421

(22) PCT Filed: Nov. 8, 2017

(86) PCT No.: PCT/US2017/060510
§ 371 (c)(1),
(2) Date: May 8, 2019

(87) PCT Pub. No.: WO2018/089407
PCT Pub. Date: May 17, 2018

(65) Prior Publication Data
US 2019/0328863 A1    Oct. 31, 2019

Related U.S. Application Data

(60) Provisional application No. 62/418,800, filed on Nov. 8, 2016.

(51) Int. Cl.
| | | |
|---|---|---|
| *F27D 1/12* | (2006.01) | |
| *A61K 39/12* | (2006.01) | |
| *F27B 3/14* | (2006.01) | |
| *F27B 3/24* | (2006.01) | |
| *F27D 11/08* | (2006.01) | |
| *F27D 9/00* | (2006.01) | |

(52) U.S. Cl.
CPC ............ *F27D 1/12* (2013.01); *F27B 3/14* (2013.01); *F27B 3/24* (2013.01); *F27D 11/08* (2013.01); *F27D 2009/0021* (2013.01)

(58) Field of Classification Search
None
See application file for complete search history.

(56) References Cited

U.S. PATENT DOCUMENTS

| | | | |
|---|---|---|---|
| 7,871,626 B2 | 1/2011 | Hoffmann et al. | |
| 2015/0132330 A1* | 5/2015 | Garcia-Sastre | ...... A61K 39/145 |
| | | | 424/186.1 |
| 2016/0199481 A1 | 7/2016 | Bloom | |
| 2018/0043007 A1* | 2/2018 | LeFebvre | ................. C12N 7/00 |

FOREIGN PATENT DOCUMENTS

| | | |
|---|---|---|
| WO | WO2012-088428 A1 | 6/2012 |
| WO | WO2015-028478 A1 | 3/2015 |

OTHER PUBLICATIONS

Gen Bank Accession CCH23214, haemagglutinin [Influenza A virus (A/WSN/1933(H1N1))], 2013.*
Gen Bank Accession, ACF54601, neuraminidase [Influenza A virus (A/WSN/1933(H1N1, 2008.*
Li et al., Glycosylation of Neuraminidase Determines the Neurovirulence of Influenza A/WSN/33 Virus, 1993, Journal of Virology, vol. 67, No. 11, pp. 6667-6673.*
Sun et al., N-Linked Glycosylation of the Hemagglutinin Protein Influences Virulence and Antigenicity of the 1918 Pandemic and Seasonal H1N1 Influenza A Viruses, 2013, Journal of Virology, vol. 87, No. 15, pp. 8756-8766.*
Hughes et al., Adaptation of Influenza A Viruses to Cells Expressing Low Levels of Sialic Acid Leads to Loss of Neuraminidase Activity, Journal of Virology, 2001, vol. 75, No. 8, pp. 3766-3770.*
Castrucci, M.R. et al., "Biologic importance of neuraminidase stalk length in influenza A virus", Journal of Virology, 1993, vol. 67, No. 2, pp. 759-764.
Wu, Chung-Yi et al., "Influenza A surface glycosylation and vaccine design", PNAS, Jan. 2017 (Epub Dec. 27, 2016), vol. 114, No. 2, pp. 280-285.

* cited by examiner

*Primary Examiner* — Benjamin P Blumel
(74) *Attorney, Agent, or Firm* — Muncy, Geissler, Olds & Lowe P.C.

(57) ABSTRACT

Immunogenic compositions comprising hemagglutinin (HA) variants and/or neuraminidase (NA) variants, which may be contained in an influenza A virus, and uses thereof for eliciting immune responses against influenza A virus.

12 Claims, 36 Drawing Sheets

Specification includes a Sequence Listing.

A

```
                            ✂ Add stop codon
         N  TM  Stalk Catalytic domain
                     104                  121
              WSN...ATA ATC TCA ATA TGG ATT...
         LAIV WSN-NA...ATA ATC TGA ATA TGG ATT...
```

Lipid bilayer

NA, HA, M1, M2, RNA segments

B

Antibody response (dilution fold): Inactivated WSN ~1100, Inactivated WSN-NA ~950, PBS 0

C H5N1
Mouse survival rate (%) vs Time after infection (day)
— LAIV WSN-NA
— WSN
— LAIV WSN-NA
— PBS

Ectodomain | TM | amphipathic helix | C-terminal

B (bar chart: Log₁₀(virus titer(pfu/ml)) for WT, M2 N-G, M2 S-I, all approximately 7.3)

SEQUENCE LISTING

```
<160> NUMBER OF SEQ ID NOS: 23

<210> SEQ ID NO 1
<211> LENGTH: 565
<212> TYPE: PRT
<213> ORGANISM: Artificial Sequence
<220> FEATURE:
<223> OTHER INFORMATION: Synthetic polypeptide

<400> SEQUENCE: 1

Met Lys Ala Phe Val Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
            20                  25                  30

Val Asp Thr Ile Phe Glu Lys Asn Val Ala Val Thr His Ser Val Asn
        35                  40                  45

Leu Leu Glu Asp Arg His Asn Gly Lys Leu Cys Lys Leu Lys Gly Ile
```

```
                50             55              60
Ala Pro Leu Gln Leu Gly Lys Cys Asn Ile Thr Gly Trp Leu Leu Gly
65                  70                  75                  80

Asn Pro Glu Cys Asp Ser Leu Leu Pro Ala Arg Ser Trp Ser Tyr Ile
                    85                  90                  95

Val Glu Thr Pro Asn Ser Glu Asn Gly Ala Cys Tyr Pro Gly Asp Phe
                100                 105                 110

Ile Asp Tyr Glu Glu Leu Arg Glu Gln Leu Ser Ser Val Ser Ser Leu
                115                 120                 125

Glu Arg Phe Glu Ile Phe Pro Lys Glu Ser Ser Trp Pro Asn His Thr
                130                 135                 140

Phe Asn Gly Val Thr Val Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
                180                 185                 190

Trp Gly Val His His Pro Ser Ser Asp Glu Gln Gln Ser Leu Tyr
                195                 200                 205

Ser Asn Gly Asn Ala Tyr Val Ser Val Ala Ser Ser Asn Tyr Asn Arg
210                 215                 220

Arg Phe Thr Pro Glu Ile Ala Ala Arg Pro Lys Val Lys Asp Gln His
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
                260                 265                 270

Leu Ser Arg Gly Phe Glu Ser Gly Ile Ile Thr Ser Ala Ala Ser Met
                275                 280                 285

His Glu Cys Asn Thr Lys Cys Gln Thr Pro Gln Gly Ser Ile Asn Ser
290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
                340                 345                 350

Ile Glu Gly Gly Trp Thr Gly Met Ile Asp Gly Trp Tyr Gly Tyr His
                355                 360                 365

His Gln Asn Glu Gln Gly Ser Gly Tyr Ala Ala Asp Gln Lys Ser Thr
                370                 375                 380

Gln Asn Ala Ile Asn Arg Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
                435                 440                 445

Arg Thr Leu Asp Phe His Asp Leu Asn Val Lys Asn Leu Tyr Glu Lys
                450                 455                 460

Val Lys Ser Gln Leu Lys Asn Asn Ala Lys Glu Ile Gly Asn Gly Cys
465                 470                 475                 480
```

Phe Glu Phe Tyr His Lys Cys Asp Asn Glu Cys Met Glu Ser Val Arg
                485                 490                 495

Ala Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Ala Gly Ser Leu Gln
545                 550                 555                 560

Cys Arg Ile Cys Ile
            565

<210> SEQ ID NO 2
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 2

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile
            20                  25                  30

<210> SEQ ID NO 3
<211> LENGTH: 565
<212> TYPE: PRT
<213> ORGANISM: Influenza A

<400> SEQUENCE: 3

Met Lys Ala Phe Val Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
            20                  25                  30

Val Asp Thr Ile Phe Glu Lys Asn Val Ala Val Thr His Ser Val Asn
            35                  40                  45

Leu Leu Glu Asp Arg His Asn Gly Lys Leu Cys Lys Leu Lys Gly Ile
        50                  55                  60

Ala Pro Leu Gln Leu Gly Lys Cys Asn Ile Thr Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ala Cys Tyr Pro Gly Asp Phe
            100                 105                 110

Ile Asp Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Asn His Thr
130                 135                 140

Phe Asn Gly Val Thr Val Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
            180                 185                 190

```
Trp Gly Val His His Pro Ser Ser Asp Glu Gln Gln Ser Leu Tyr
            195                 200                 205
Ser Asn Gly Asn Ala Tyr Val Ser Val Ala Ser Ser Asn Tyr Asn Arg
        210                 215                 220
Arg Phe Thr Pro Glu Ile Ala Ala Arg Pro Lys Val Lys Asp Gln His
225                 230                 235                 240
Gly Arg Met Asn Tyr Tyr Trp Thr Leu Leu Glu Pro Gly Asp Thr Ile
                245                 250                 255
Ile Phe Glu Ala Thr Gly Asn Leu Ile Ala Pro Trp Tyr Ala Phe Ala
            260                 265                 270
Leu Ser Arg Gly Phe Glu Ser Gly Ile Ile Thr Ser Asn Ala Ser Met
        275                 280                 285
His Glu Cys Asn Thr Lys Cys Gln Thr Pro Gln Gly Ser Ile Asn Ser
290                 295                 300
Asn Leu Pro Phe Gln Asn Ile His Pro Val Thr Ile Gly Glu Cys Pro
305                 310                 315                 320
Lys Tyr Val Arg Ser Thr Lys Leu Arg Met Val Thr Gly Leu Arg Asn
                325                 330                 335
Ile Pro Ser Ile Gln Tyr Arg Gly Leu Phe Gly Ala Ile Ala Gly Phe
            340                 345                 350
Ile Glu Gly Gly Trp Thr Gly Met Ile Asp Gly Trp Tyr Gly Tyr His
        355                 360                 365
His Gln Asn Glu Gln Gly Ser Gly Tyr Ala Ala Asp Gln Lys Ser Thr
370                 375                 380
Gln Asn Ala Ile Asn Arg Ile Thr Asn Lys Val Asn Ser Val Ile Glu
385                 390                 395                 400
Lys Met Asn Thr Gln Phe Thr Ala Val Gly Lys Glu Phe Asn Asn Leu
                405                 410                 415
Glu Lys Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Leu Asn Val Lys Asn Leu Tyr Glu Lys
450                 455                 460
Val Lys Ser Gln Leu Lys Asn Asn Ala Lys Glu Ile Gly Asn Gly Cys
465                 470                 475                 480
Phe Glu Phe Tyr His Lys Cys Asp Asn Glu Cys Met Glu Ser Val Arg
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 4
<211> LENGTH: 453
<212> TYPE: PRT
<213> ORGANISM: Influenza A

<400> SEQUENCE: 4
```

```
Met Asn Pro Asn Gln Lys Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Asn His Thr Gly Ile
            35                  40                  45

Cys Asn Gln Gly Ser Ile Thr Tyr Lys Val Val Ala Gly Gln Asp Ser
            50                  55                  60

Thr Ser Val Ile Leu Thr Gly Asn Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Arg Glu Pro Phe Ile Ser Cys Ser His Leu Glu
                100                 105                 110

Cys Arg Thr Phe Phe Leu Thr Gln Gly Ala Leu Leu Asn Asp Lys His
            115                 120                 125

Ser Arg Gly Thr Phe Lys Asp Arg Ser Pro Tyr Arg Ala Leu Met Ser
130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Gly Ile Ile Thr Glu Thr Ile Lys Ser Trp Arg Lys Asn Ile Leu
            195                 200                 205

Arg Thr Gln Glu Ser Glu Cys Thr Cys Val Asn Gly Ser Cys Phe Thr
210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
            245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
            275                 280                 285

Ser Phe Asp Gln Asn Leu Asp Tyr Lys Ile Gly Tyr Ile Cys Ser Gly
            290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
                340                 345                 350

His Gly Phe Glu Met Ile Trp Asp Pro Asn Gly Trp Thr Glu Thr Asp
            355                 360                 365

Ser Arg Phe Ser Met Arg Gln Asp Val Val Ala Met Thr Asp Arg Ser
            370                 375                 380

Gly Tyr Ser Gly Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
                405                 410                 415
```

-continued

```
Glu Asn Ala Ile Trp Thr Ser Gly Ser Ile Ile Ser Phe Cys Gly Val
                420                 425                 430

Asn Ser Asp Thr Val Asp Trp Ser Trp Pro Asp Gly Ala Glu Leu Pro
            435                 440                 445

Phe Thr Ile Asp Lys
        450

<210> SEQ ID NO 5
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 5

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile
            20                  25

<210> SEQ ID NO 6
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 6

Ile Ser Ile Trp Ile Ser His Ser Ile Gln Thr Gly Asn Gln Asn His
1               5                   10                  15

Thr Gly Ile Cys Asn Gln Gly Ser Ile Thr Tyr Lys Val Val Ala Gly
            20                  25                  30

Gln Asp Ser Thr Ser Val Ile Leu Thr Gly Asn Ser Ser
        35                  40                  45

<210> SEQ ID NO 7
<211> LENGTH: 379
<212> TYPE: PRT
<213> ORGANISM: Artificial Sequence
<220> FEATURE:
<223> OTHER INFORMATION: Synthetic polypeptide

<400> SEQUENCE: 7

Leu Cys Pro Ile Arg Gly Trp Ala Ile His Ser Lys Asp Asn Gly Ile
1               5                   10                  15

Arg Ile Gly Ser Lys Gly Asp Val Phe Val Ile Arg Glu Pro Phe Ile
            20                  25                  30

Ser Cys Ser His Leu Glu Cys Arg Thr Phe Phe Leu Thr Gln Gly Ala
        35                  40                  45

Leu Leu Asn Asp Lys His Ser Arg Gly Thr Phe Lys Asp Arg Ser Pro
    50                  55                  60

Tyr Arg Ala Leu Met Ser Cys Pro Val Gly Glu Ala Pro Ser Pro Tyr
65                  70                  75                  80

Asn Ser Arg Phe Glu Ser Val Ala Trp Ser Ala Ser Ala Cys His Asp
                85                  90                  95

Gly Met Gly Trp Leu Thr Ile Gly Ile Ser Gly Pro Asp Asp Gly Ala
            100                 105                 110

Val Ala Val Leu Lys Tyr Asn Gly Ile Ile Thr Glu Thr Ile Lys Ser
        115                 120                 125

Trp Arg Lys Asn Ile Leu Arg Thr Gln Glu Ser Glu Cys Thr Cys Val
```

```
                130                 135                 140
Asn Gly Ser Cys Phe Thr Ile Met Thr Asp Gly Pro Ser Asp Gly Leu
145                 150                 155                 160

Ala Ser Tyr Lys Ile Phe Lys Ile Glu Lys Gly Lys Val Thr Lys Ser
                165                 170                 175

Ile Glu Leu Asn Ala Pro Asn Ser His Tyr Glu Cys Ser Cys Tyr
                180                 185                 190

Pro Asp Thr Gly Lys Val Met Cys Val Cys Arg Asp Asn Trp His Gly
                195                 200                 205

Ser Asn Arg Pro Trp Val Ser Phe Asp Gln Asn Leu Asp Tyr Lys Ile
            210                 215                 220

Gly Tyr Ile Cys Ser Gly Val Phe Gly Asp Asn Pro Arg Pro Lys Asp
225                 230                 235                 240

Gly Thr Gly Ser Cys Gly Pro Val Ser Ala Asp Gly Ala Asn Gly Val
                245                 250                 255

Lys Gly Phe Ser Tyr Lys Tyr Gly Asn Gly Val Trp Ile Gly Arg Thr
                260                 265                 270

Lys Ser Asp Ser Ser Arg His Gly Phe Glu Met Ile Trp Asp Pro Asn
            275                 280                 285

Gly Trp Thr Glu Thr Asp Ser Arg Phe Ser Met Arg Gln Asp Val Val
        290                 295                 300

Ala Met Thr Asp Arg Ser Gly Tyr Ser Gly Ser Phe Val Gln His Pro
305                 310                 315                 320

Glu Leu Thr Gly Leu Asp Cys Met Arg Pro Cys Phe Trp Val Glu Leu
                325                 330                 335

Ile Arg Gly Leu Pro Glu Glu Asn Ala Ile Trp Thr Ser Gly Ser Ile
                340                 345                 350

Ile Ser Phe Cys Gly Val Asn Ser Asp Thr Val Asp Trp Ser Trp Pro
                355                 360                 365

Asp Gly Ala Glu Leu Pro Phe Thr Ile Asp Lys
        370                 375

<210> SEQ ID NO 8
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 8

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
                20                  25                  30

Trp Ile Ser His Ser Ile Gln Thr Gly Asn Gln Ala His Thr Gly Ile
            35                  40                  45

Cys Asn Gln Gly Ser Ile Thr Tyr Lys Val Val Ala Gly Gln Asp Ser
        50                  55                  60

Thr Ser Val Ile Leu Thr Gly Asn Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Arg Glu Pro Phe Ile Ser Cys Ser His Leu Glu
                100                 105                 110

Cys Arg Thr Phe Phe Leu Thr Gln Gly Ala Leu Leu Asn Asp Lys His
```

```
            115                 120                 125
Ser Arg Gly Thr Phe Lys Asp Arg Ser Pro Tyr Arg Ala Leu Met Ser
130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Gly Ile Ile Thr Glu Thr Ile Lys Ser Trp Arg Lys Asn Ile Leu
        195                 200                 205

Arg Thr Gln Glu Ser Glu Cys Thr Cys Val Asn Gly Ser Cys Phe Thr
210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
        275                 280                 285

Ser Phe Asp Gln Asn Leu Asp Tyr Lys Ile Gly Tyr Ile Cys Ser Gly
290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
        355                 360                 365

Ser Arg Phe Ser Met Arg Gln Asp Val Val Ala Met Thr Asp Arg Ser
370                 375                 380

Gly Tyr Ser Gly Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
                405                 410                 415

Glu Asn Ala Ile Trp Thr Ser Gly Ser Ile Ile Ser Phe Cys Gly Val
            420                 425                 430

Asn Ser Asp Thr Val Asp Trp Ser Trp Pro Asp Gly Ala Glu Leu Pro
        435                 440                 445

Phe Thr Ile Asp Lys
        450

<210> SEQ ID NO 9
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 9

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
```

-continued

```
              20                  25                  30
Trp Ile Ser His Ser Ile Gln Thr Gly Asn Gln Asn His Thr Gly Ile
             35                  40                  45
Cys Asn Gln Gly Ser Ile Thr Tyr Lys Val Val Ala Gly Gln Asp Ser
 50                  55                  60
Thr Ser Val Ile Leu Thr Gly Ala Ser Ser Leu Cys Pro Ile Arg Gly
 65                  70                  75                  80
Trp Ala Ile His Ser Lys Asp Asn Gly Ile Arg Ile Gly Ser Lys Gly
                 85                  90                  95
Asp Val Phe Val Ile Arg Glu Pro Phe Ile Ser Cys Ser His Leu Glu
                100                 105                 110
Cys Arg Thr Phe Phe Leu Thr Gln Gly Ala Leu Leu Asn Asp Lys His
                115                 120                 125
Ser Arg Gly Thr Phe Lys Asp Arg Ser Pro Tyr Arg Ala Leu Met Ser
                130                 135                 140
Cys Pro Val Gly Glu Ala Pro Ser Pro Tyr Asn Ser Arg Phe Glu Ser
145                 150                 155                 160
Val Ala Trp Ser Ala Ser Ala Cys His Asp Gly Met Gly Trp Leu Thr
                165                 170                 175
Ile Gly Ile Ser Gly Pro Asp Asp Gly Ala Val Ala Val Leu Lys Tyr
                180                 185                 190
Asn Gly Ile Ile Thr Glu Thr Ile Lys Ser Trp Arg Lys Asn Ile Leu
                195                 200                 205
Arg Thr Gln Glu Ser Glu Cys Thr Cys Val Asn Gly Ser Cys Phe Thr
                210                 215                 220
Ile Met Thr Asp Gly Pro Ser Asp Gly Leu Ala Ser Tyr Lys Ile Phe
225                 230                 235                 240
Lys Ile Glu Lys Gly Lys Val Thr Lys Ser Ile Glu Leu Asn Ala Pro
                245                 250                 255
Asn Ser His Tyr Glu Glu Cys Ser Cys Tyr Pro Asp Thr Gly Lys Val
                260                 265                 270
Met Cys Val Cys Arg Asp Asn Trp His Gly Ser Asn Arg Pro Trp Val
                275                 280                 285
Ser Phe Asp Gln Asn Leu Asp Tyr Lys Ile Gly Tyr Ile Cys Ser Gly
                290                 295                 300
Val Phe Gly Asp Asn Pro Arg Pro Lys Asp Gly Thr Gly Ser Cys Gly
305                 310                 315                 320
Pro Val Ser Ala Asp Gly Ala Asn Gly Val Lys Gly Phe Ser Tyr Lys
                325                 330                 335
Tyr Gly Asn Gly Val Trp Ile Gly Arg Thr Lys Ser Asp Ser Ser Arg
                340                 345                 350
His Gly Phe Glu Met Ile Trp Asp Pro Asn Gly Trp Thr Glu Thr Asp
                355                 360                 365
Ser Arg Phe Ser Met Arg Gln Asp Val Val Ala Met Thr Asp Arg Ser
                370                 375                 380
Gly Tyr Ser Gly Ser Phe Val Gln His Pro Glu Leu Thr Gly Leu Asp
385                 390                 395                 400
Cys Met Arg Pro Cys Phe Trp Val Glu Leu Ile Arg Gly Leu Pro Glu
                405                 410                 415
Glu Asn Ala Ile Trp Thr Ser Gly Ser Ile Ile Ser Phe Cys Gly Val
                420                 425                 430
Asn Ser Asp Thr Val Asp Trp Ser Trp Pro Asp Gly Ala Glu Leu Pro
                435                 440                 445
```

Phe Thr Ile Asp Lys
    450

<210> SEQ ID NO 10
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 10

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Ala His Thr Gly Ile
        35                  40                  45

Cys Asn Gln Gly Ser Ile Thr Tyr Lys Val Val Ala Gly Gln Asp Ser
    50                  55                  60

Thr Ser Val Ile Leu Thr Gly Ala Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Arg Glu Pro Phe Ile Ser Cys Ser His Leu Glu
            100                 105                 110

Cys Arg Thr Phe Phe Leu Thr Gln Gly Ala Leu Leu Asn Asp Lys His
        115                 120                 125

Ser Arg Gly Thr Phe Lys Asp Arg Ser Pro Tyr Arg Ala Leu Met Ser
    130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Gly Ile Ile Thr Glu Thr Ile Lys Ser Trp Arg Lys Asn Ile Leu
        195                 200                 205

Arg Thr Gln Glu Ser Glu Cys Thr Cys Val Asn Gly Ser Cys Phe Thr
    210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
        275                 280                 285

Ser Phe Asp Gln Asn Leu Asp Tyr Lys Ile Gly Tyr Ile Cys Ser Gly
    290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
        355                 360                 365

Ser Arg Phe Ser Met Arg Gln Asp Val Val Ala Met Thr Asp Arg Ser
    370                 375                 380

Gly Tyr Ser Gly Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
                405                 410                 415

Glu Asn Ala Ile Trp Thr Ser Gly Ser Ile Ile Ser Phe Cys Gly Val
            420                 425                 430

Asn Ser Asp Thr Val Asp Trp Ser Trp Pro Asp Gly Ala Glu Leu Pro
        435                 440                 445

Phe Thr Ile Asp Lys
        450

<210> SEQ ID NO 11
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 11

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Ala His Thr Gly Ile
        35                  40                  45

Cys Asn Gln Gly Ser Ile Thr Tyr Lys Val Val Ala Gly Gln Asp Ser
    50                  55                  60

Thr Ser Val Ile Leu Thr Gly Ala Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Arg Glu Pro Phe Ile Ser Cys Ser His Leu Glu
            100                 105                 110

Cys Arg Thr Phe Phe Leu Thr Gln Gly Ala Leu Leu Asn Asp Lys His
        115                 120                 125

Ser Arg Gly Thr Phe Lys Asp Arg Ser Pro Tyr Arg Ala Leu Met Ser
    130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Gly Ile Ile Thr Glu Thr Ile Lys Ser Trp Arg Lys Asn Ile Leu
        195                 200                 205

Arg Thr Gln Glu Ser Glu Cys Thr Cys Val Ala Gly Ser Cys Phe Thr
    210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

```
Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
        275                 280                 285

Ser Phe Asp Gln Asn Leu Asp Tyr Lys Ile Gly Tyr Ile Cys Ser Gly
    290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
        355                 360                 365

Ser Arg Phe Ser Met Arg Gln Asp Val Val Ala Met Thr Asp Arg Ser
    370                 375                 380

Gly Tyr Ser Gly Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
                405                 410                 415

Glu Asn Ala Ile Trp Thr Ser Gly Ser Ile Ile Ser Phe Cys Gly Val
            420                 425                 430

Asn Ser Asp Thr Val Asp Trp Ser Trp Pro Asp Gly Ala Glu Leu Pro
        435                 440                 445

Phe Thr Ile Asp Lys
    450

<210> SEQ ID NO 12
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 12

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Asn His Thr Gly Ile
        35                  40                  45

Cys Asn Gln Gly Ser Ile Thr Tyr Lys Val Val Ala Gly Gln Asp Ser
    50                  55                  60

Thr Ser Val Ile Leu Thr Gly Asn Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Ala Glu Pro Phe Ile Ser Cys Ser His Leu Glu
            100                 105                 110

Cys Arg Thr Phe Phe Leu Thr Gln Gly Ala Leu Leu Asn Asp Lys His
        115                 120                 125

Ser Arg Gly Thr Phe Lys Asp Arg Ser Pro Tyr Arg Ala Leu Met Ser
    130                 135                 140

Cys Pro Val Gly Glu Ala Pro Ser Pro Tyr Asn Ser Arg Phe Glu Ser
145                 150                 155                 160
```

```
Val Ala Trp Ser Ala Ser Ala Cys His Asp Gly Met Gly Trp Leu Thr
            165                 170                 175

Ile Gly Ile Ser Gly Pro Asp Asp Gly Ala Val Ala Val Leu Lys Tyr
        180                 185                 190

Asn Gly Ile Ile Thr Glu Thr Ile Lys Ser Trp Arg Lys Asn Ile Leu
    195                 200                 205

Arg Thr Gln Glu Ser Glu Cys Thr Cys Val Asn Gly Ser Cys Phe Thr
210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
        275                 280                 285

Ser Phe Asp Gln Asn Leu Asp Tyr Lys Ile Gly Tyr Ile Cys Ser Gly
    290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
        355                 360                 365

Ser Arg Phe Ser Met Arg Gln Asp Val Val Ala Met Thr Asp Arg Ser
    370                 375                 380

Gly Tyr Ser Gly Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
                405                 410                 415

Glu Asn Ala Ile Trp Thr Ser Gly Ser Ile Ile Ser Phe Cys Gly Val
            420                 425                 430

Asn Ser Asp Thr Val Asp Trp Ser Trp Pro Asp Gly Ala Glu Leu Pro
        435                 440                 445

Phe Thr Ile Asp Lys
    450

<210> SEQ ID NO 13
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 13

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Asn His Thr Gly Ile
        35                  40                  45

Cys Asn Gln Gly Ser Ile Thr Tyr Lys Val Val Ala Gly Gln Asp Ser
    50                  55                  60
```

Thr Ser Val Ile Leu Thr Gly Asn Ser Ser Leu Cys Pro Ile Arg Gly
 65                  70                  75                  80

Trp Ala Ile His Ser Lys Asp Asn Gly Ile Arg Ile Gly Ser Lys Gly
                 85                  90                  95

Asp Val Phe Val Ile Arg Glu Pro Phe Ile Ser Cys Ser His Leu Glu
            100                 105                 110

Cys Arg Thr Phe Phe Leu Thr Gln Gly Ala Leu Leu Asn Asp Lys His
        115                 120                 125

Ser Arg Gly Thr Phe Lys Ala Arg Ser Pro Tyr Arg Ala Leu Met Ser
130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Gly Ile Ile Thr Glu Thr Ile Lys Ser Trp Arg Lys Asn Ile Leu
        195                 200                 205

Arg Thr Gln Glu Ser Glu Cys Thr Cys Val Asn Gly Ser Cys Phe Thr
210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
        275                 280                 285

Ser Phe Asp Gln Asn Leu Asp Tyr Lys Ile Gly Tyr Ile Cys Ser Gly
290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
        355                 360                 365

Ser Arg Phe Ser Met Arg Gln Asp Val Val Ala Met Thr Asp Arg Ser
370                 375                 380

Gly Tyr Ser Gly Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
                405                 410                 415

Glu Asn Ala Ile Trp Thr Ser Gly Ser Ile Ile Ser Phe Cys Gly Val
            420                 425                 430

Asn Ser Asp Thr Val Asp Trp Ser Trp Pro Asp Gly Ala Glu Leu Pro
        435                 440                 445

Phe Thr Ile Asp Lys
450

<210> SEQ ID NO 14
<211> LENGTH: 453

<212> TYPE: PRT
<213> ORGANISM: Artificial Sequence
<220> FEATURE:
<223> OTHER INFORMATION: Synthetic polypeptide

<400> SEQUENCE: 14

```
Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Asn His Thr Gly Ile
        35                  40                  45

Cys Asn Gln Gly Ser Ile Thr Tyr Lys Val Val Ala Gly Gln Asp Ser
    50                  55                  60

Thr Ser Val Ile Leu Thr Gly Asn Ser Ser Leu Cys Pro Ile Arg Gly
65                  70                  75                  80

Trp Ala Ile His Ser Lys Asp Asn Gly Ile Arg Ile Gly Ser Lys Gly
                85                  90                  95

Asp Val Phe Val Ile Arg Glu Pro Phe Ile Ser Cys Ser His Leu Glu
            100                 105                 110

Cys Arg Thr Phe Phe Leu Thr Gln Gly Ala Leu Leu Asn Asp Lys His
        115                 120                 125

Ser Arg Gly Thr Phe Lys Asp Arg Ser Pro Tyr Arg Ala Leu Met Ser
    130                 135                 140

Cys Pro Val Gly Glu Ala Pro Ser Pro Tyr Asn Ser Arg Phe Glu Ser
145                 150                 155                 160

Val Ala Trp Ser Ala Ser Ala Cys His Asp Gly Met Gly Trp Leu Thr
                165                 170                 175

Ile Gly Ile Ser Gly Pro Asp Asp Gly Ala Val Ala Val Leu Lys Tyr
            180                 185                 190

Asn Gly Ile Ile Thr Glu Thr Ile Lys Ser Trp Arg Lys Asn Ile Leu
        195                 200                 205

Arg Thr Gln Glu Ser Glu Cys Thr Cys Val Asn Gly Ser Cys Phe Thr
    210                 215                 220

Ile Met Thr Asp Gly Pro Ser Asp Gly Leu Ala Ser Tyr Lys Ile Phe
225                 230                 235                 240

Lys Ile Glu Lys Gly Lys Val Thr Lys Ser Ile Glu Leu Asn Ala Pro
                245                 250                 255

Asn Ser His Tyr Glu Glu Cys Ser Cys Tyr Pro Asp Thr Gly Lys Val
            260                 265                 270

Met Cys Val Cys Arg Asp Asn Trp His Gly Ser Asn Arg Pro Trp Val
        275                 280                 285

Ser Phe Asp Gln Asn Leu Asp Tyr Lys Ile Gly Tyr Ile Cys Ser Gly
    290                 295                 300

Val Phe Gly Asp Asn Pro Arg Pro Lys Asp Gly Thr Gly Ser Cys Gly
305                 310                 315                 320

Pro Val Ser Ala Asp Gly Ala Asn Gly Val Lys Gly Phe Ser Tyr Lys
                325                 330                 335

Tyr Gly Asn Gly Val Trp Ile Gly Arg Thr Lys Ser Asp Ser Ser Arg
            340                 345                 350

His Gly Phe Glu Met Ile Trp Asp Pro Asn Gly Trp Thr Glu Thr Asp
        355                 360                 365

Ser Arg Phe Ser Met Arg Gln Asp Val Val Ala Met Thr Asp Arg Ser
    370                 375                 380
```

```
Gly Tyr Ser Ala Ser Phe Val Gln His Pro Glu Leu Thr Gly Leu Asp
385                 390                 395                 400

Cys Met Arg Pro Cys Phe Trp Val Glu Leu Ile Arg Gly Leu Pro Glu
            405                 410                 415

Glu Asn Ala Ile Trp Thr Ser Gly Ile Ile Ser Phe Cys Gly Val
        420                 425                 430

Asn Ser Asp Thr Val Asp Trp Ser Trp Pro Asp Gly Ala Glu Leu Pro
            435                 440                 445

Phe Thr Ile Asp Lys
        450

<210> SEQ ID NO 15
<211> LENGTH: 74
<212> TYPE: PRT
<213> ORGANISM: Artificial Sequence
<220> FEATURE:
<223> OTHER INFORMATION: Synthetic polypeptide

<400> SEQUENCE: 15

Met Asn Pro Asn Gln Lys Ile Ile Thr Ile Gly Ser Ile Cys Met Val
1               5                   10                  15

Val Gly Ile Ile Ser Leu Ile Leu Gln Ile Gly Asn Ile Ile Ser Ile
            20                  25                  30

Trp Ile Ser His Ser Ile Gln Thr Gly Asn Gln Asn His Thr Gly Ile
        35                  40                  45

Cys Asn Gln Gly Ser Ile Thr Tyr Lys Val Val Ala Gly Gln Asp Ser
    50                  55                  60

Thr Ser Val Ile Leu Thr Gly Asn Ser Ser
65                  70

<210> SEQ ID NO 16
<211> LENGTH: 565
<212> TYPE: PRT
<213> ORGANISM: Artificial Sequence
<220> FEATURE:
<223> OTHER INFORMATION: Synthetic polypeptide

<400> SEQUENCE: 16

Met Lys Ala Phe Val Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
            20                  25                  30

Val Asp Thr Ile Phe Glu Lys Asn Val Ala Val Thr His Ser Val Asn
            35                  40                  45

Leu Leu Glu Asp Arg His Asn Gly Lys Leu Cys Lys Leu Lys Gly Ile
    50                  55                  60

Ala Pro Leu Gln Leu Gly Lys Cys Asn Ile Thr Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ala Cys Tyr Pro Gly Asp Phe
            100                 105                 110

Ile Asp Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Ala His Thr
    130                 135                 140

Phe Asn Gly Val Thr Val Ser Cys Ser His Arg Gly Lys Ser Ser Phe
145                 150                 155                 160
```

Tyr Arg Asn Leu Leu Trp Leu Thr Lys Lys Gly Asp Ser Tyr Pro Lys
            165                 170                 175

Leu Thr Asn Ser Tyr Val Asn Lys Gly Lys Glu Val Leu Val Leu
            180                 185                 190

Trp Gly Val His His Pro Ser Ser Asp Glu Gln Gln Ser Leu Tyr
            195                 200                 205

Ser Asn Gly Asn Ala Tyr Val Ser Val Ala Ser Ser Asn Tyr Asn Arg
            210                 215                 220

Arg Phe Thr Pro Glu Ile Ala Ala Arg Pro Lys Val Lys Asp Gln His
225                 230                 235                 240

Gly Arg Met Asn Tyr Tyr Trp Thr Leu Leu Glu Pro Gly Asp Thr Ile
            245                 250                 255

Ile Phe Glu Ala Thr Gly Asn Leu Ile Ala Pro Trp Tyr Ala Phe Ala
            260                 265                 270

Leu Ser Arg Gly Phe Glu Ser Gly Ile Ile Thr Ser Asn Ala Ser Met
            275                 280                 285

His Glu Cys Asn Thr Lys Cys Gln Thr Pro Gln Gly Ser Ile Asn Ser
            290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
            325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Arg Ile Thr Asn Lys Val Asn Ser Val Ile Glu
385                 390                 395                 400

Lys Met Asn Thr Gln Phe Thr Ala Val Gly Lys Glu Phe Asn Asn Leu
            405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Leu Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 17
<211> LENGTH: 565
<212> TYPE: PRT
<213> ORGANISM: Artificial Sequence
<220> FEATURE:
<223> OTHER INFORMATION: Synthetic polypeptide

<400> SEQUENCE: 17

```
Met Lys Ala Phe Val Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
                20                  25                  30

Val Asp Thr Ile Phe Glu Lys Asn Val Ala Val Thr His Ser Val Asn
            35                  40                  45

Leu Leu Glu Asp Arg His Asn Gly Lys Leu Cys Lys Leu Lys Gly Ile
    50                  55                  60

Ala Pro Leu Gln Leu Gly Lys Cys Asn Ile Thr Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ala Cys Tyr Pro Gly Asp Phe
            100                 105                 110

Ile Asp Tyr Glu Glu Leu Arg Glu Gln Leu Ser Ser Val Ser Ser Leu
        115                 120                 125

Glu Arg Phe Glu Ile Phe Pro Lys Glu Ser Ser Trp Pro Ala His Thr
130                 135                 140

Phe Asn Gly Val Thr Val Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
            180                 185                 190

Trp Gly Val His His Pro Ser Ser Ser Asp Glu Gln Gln Ser Leu Tyr
        195                 200                 205

Ser Asn Gly Asn Ala Tyr Val Ser Val Ala Ser Ser Asn Tyr Asn Arg
210                 215                 220

Arg Phe Thr Pro Glu Ile Ala Ala Arg Pro Lys Val Lys Asp Gln His
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Glu Ser Gly Ile Ile Thr Ser Ala Ala Ser Met
        275                 280                 285

His Glu Cys Asn Thr Lys Cys Gln Thr Pro Gln Gly Ser Ile Asn Ser
290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365
```

His Gln Asn Glu Gln Gly Ser Gly Tyr Ala Ala Asp Gln Lys Ser Thr
    370                 375                 380

Gln Asn Ala Ile Asn Arg Ile Thr Asn Lys Val Asn Ser Val Ile Glu
385                 390                 395                 400

Lys Met Asn Thr Gln Phe Thr Ala Val Gly Lys Glu Phe Asn Asn Leu
                    405                 410                 415

Glu Lys Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Leu Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Ala Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Ala Gly Ser Leu Gln
545                 550                 555                 560

Cys Arg Ile Cys Ile
            565

<210> SEQ ID NO 18
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 18

Gly Ile Leu Gly Phe Val Phe Thr Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 19

Arg Leu Glu Asp Val Phe Ala Gly Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 20

Ala Ser Cys Met Gly Leu Ile Tyr
1               5

```
<210> SEQ ID NO 21
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 21

Cys Thr Glu Leu Lys Leu Ser Asp Tyr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 22

Ser Arg Tyr Trp Ala Ile Arg Thr Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 23

Leu Glu Leu Arg Ser Arg Tyr Trp Ala
1               5
```

RECOMBINANT VIRUS, COMPOSITION COMPRISING THE SAME, AND USES THEREOF

CROSS REFERENCE TO RELATED APPLICATIONS

This application is a U.S. National Stage Filing under 35 U.S.C. 371 from International Patent Application Serial No. PCT/US2017/060510, filed Nov. 8, 2017, and published on May 17, 2018, which claims the priority of U.S. Ser. No. 62/418,800, filed Nov. 8, 2016, the disclosure of which are incorporated by reference herein in their entireties.

BACKGROUND OF THE INVENTION

Influenza A Virus (IAV) belongs to the Orthomyxoviridae family and can circulate widely and cross interspecies barriers. Given the prevalence of Influenza A epidemics in the past decade, IAV infection constitutes a major global health threat.

Hemagglutinin (HA) and neuraminidase (NA) are glycoproteins located on the surface of IAV. Antigenic drift and shift of HA and NA proteins necessitate development of vaccines that provide improved protection against IAV infection. It is therefore of great interest to identify HA and NA variants having improved immunogenicity for use in developing vaccines to combat the rapidly evolving IAV.

SUMMARY OF THE INVENTION

The present disclosure is based, at least in part, on the unexpected discoveries that recombinant influenza virus (IAV) comprising a mutant hemagglutinin (HA) antigen with a modified N-glycosylation pattern or comprising a mutant neuraminidase (NA) having defective neuraminidase activity exhibited enhanced immunogenicity as compared with wild-type counterparts.

Accordingly, one aspect of the present disclosure features a recombinant Influenza A virus (IAV), comprising a mutant hemagglutinin (HA), which, as compared with its wild-type counterpart, retains an Asn residue at a position corresponding to residue 142 in SEQ ID NO:1 (or SEQ ID NO: 3) and contains a mutation at one or more of positions corresponding to residues 285, 497 and 556 in SEQ ID NO:1 (or SEQ ID NO: 3), wherein the mutant HA is N-glycosylated at the position corresponding to residue 142 in SEQ ID NO:1 (or SEQ ID NO: 3) and is aglycosylated at the one or more mutated positions corresponding to residues 285, 497, and 556 in SEQ ID NO:1 (or SEQ ID NO: 3).

In some embodiments, the mutant HA may further retain an Asn residue at a position corresponding to residue 27 in SEQ ID NO:1, and wherein the mutant HA is N-glycosylated at the position corresponding to residue 27 in SEQ ID NO:1.

Any of the mutant HA antigens described herein may comprise an amino acid sequence at least 85% (e.g., 90%, 95%, 98%, or 99%) identical to SEQ ID NO:1 (or SEQ ID NO: 3). In one example, the HA mutant comprises the amino acid sequence of SEQ ID NO:1.

Any of the mutant HA antigens described herein is also within the scope of the present disclosure.

In another aspect, the present disclosure provides a recombinant Influenza A virus (IAV), comprising a mutant neuraminidase (NA), which, as compared with its wild-type counterpart, comprises (a) a mutation at one or more of the active sites, (b) a mutation at one or more of the N-glycosylation sites, or a combination of (a) and (b); wherein the mutant NA is defective in neuraminidase activity.

In some embodiments, the mutant NA may comprise a substitution at one or more N-glycosylation sites corresponding to positions 44, 72, and 219 in SEQ ID NO: 4. For example, the mutant NA may comprise (1) a substitution at the position corresponding to 44 in SEQ ID NO:4, (2) a substitution at the position corresponding to 72 in SEQ ID NO:4, (3) substitutions at the positions corresponding to 44 and 72 in SEQ ID NO:4, or (4) substitutions at the positions corresponding to 44, 72, and 219 in SEQ ID NO:4. Alternatively or in addition, the mutant NA comprises a substitution at one or more of active sites, which may be at the positions corresponding to 102 and 135 in SEQ ID NO: 4. Any of the NA mutants described herein may comprise an amino acid sequence at least 85% (e.g., 90%, 95%, 98%, or 99%) identical to SEQ ID NO: 4.

In some embodiments, the mutant NA may comprise a deletion at one or more regions containing one or more N-glycosylation sites, one or more active sites, or both. For example, the mutant NA may comprise a deletion in the stalk region, a deletion in the catalytic domain, or both. In one example, the mutant NA may have the whole catalytic domain deleted. In other examples, the mutant NA may have both the catalytic domain and the stalk region deleted. In one particular example, the mutant NA is the peptide of SEQ ID NO: 2.

Any of the NA mutants disclosed herein is also within the scope of the present disclosure.

In another aspect, the present disclosure provides an immunogenic composition, comprising (i) any of the recombinant Influenza A viruses (IAVs) or any of the HA mutants described herein, and (ii) a pharmaceutically acceptable carrier, which may be an adjuvant.

In yet another aspect, the present disclosure provides a method for inducing immune responses against influenza A virus in a subject, the method comprising administering to a subject in need thereof an effective amount of the immunogenic composition as described herein. In some embodiments, the subject is a human subject, who may be infected, suspected of being infected, or at risk for infection by an influenza A virus. Exemplary influenza A virus includes, but are not limited to, an H1N1 or H5N1 influenza A virus. The immunogenic composition can be administered to the subject via oral administration, enteral administration, nasal administration, topical administration, or transmucosal administration. In one example, the immunogenic composition can be administered to the subject parenterally.

Also within the scope of the present disclosure are recombinant IAVs, HA variants, or NA variants described herein, or immunogenic compositions comprising such for use in treating or preventing influenza A virus infection in a subject in need of the treatment, or uses of the IAVs, the HA variants, the NA variants, or the immunogenic compositions for manufacturing a medicament for use in treating or preventing influenza A virus infection.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 4 includes diagrams showing the impact of truncation on the immunogenicity of NA on a live attenuated influenza vaccine (LAIV). (A): a schematic overview of the LAIV H1N1 A/WSN/33 (WSN)-NA design. Numbers refer to the nucleotide numbers from the 5' end of the cRNA. TGA was the stop codon. (B): a diagram showing immunogenicity of WT IAV (WSN) and IAV variant as indicated in mice, which were immunized with inactivated viruses, using a hemagglutination inhibition assay of the sera obtained from the immunized mice. (C): a diagram showing the survival rate of mice treated with indicated virus and subsequently challenged with H5N1 virus. (D): a diagram showing the H5N1 virus replication kinetics in the lungs of mice treated as indicated. (E): a diagram showing immunogenicity of WT IAV (WSN) and LAIV WSN-NA as indicated in mice, using a hemagglutination inhibition assay of the sera obtained from the immunized mice. (F): a diagram showing the ability of LAIV WSN-NA to induce CD8+ T-cell activation upon virus infection, using flow cytometry analysis of INF-γ expression in CD8+ T cells after incubation of WSN virus (+virus) with peripheral blood mononuclear cells (PBMC) from immunized mice as indicated. (G): a diagram showing the ability of LAIV WSN-NA virus to induce CD8+ T-cell activation upon stimulation by M1 and NP epitopes, using flow cytometry analysis of INF-γ expression in CD8+ T cells after incubation of indicated epitopes with PBMC from immunized mice as indicated. In panels B, D and E, Mean±SEM of 10 independent experiments is shown; in panel C, 10 independent experiments are shown; in panels F and G, Data are representative of three similar experiments. *: $P<0.001$.

FIG. 9 includes diagrams showing the impact of glycosylation on the immunogenicity of NA on a live attenuated influenza vaccine (LAIV). (A): a chart showing the survival rate of WSN, LAIV WSN-44-72-219-G or PBS treatment mice after challenge with a lethal-dose of H5N1. (B): a diagram showing immunogenicity of WT IAV and LAIV variant as indicated in mice, which were immunized with inactivated viruses, using a hemagglutination inhibition assay of the sera obtained from the immunized mice. (C): a diagram showing the titer of NA antibody from mice, which were immunized as indicated, using the neuraminidase inhibition assay. The half maximal inhibitory concentration (IC50) of sera from WSN treated mice was 4.3 µg/ml, and LAIV WSN-44-72-219-G was 3.2 µg/ml. In panel A, 5 independent experiments is shown; in panels B and C, Mean±SEM of 5 independent experiments is shown.

FIG. 13 includes diagrams showing the impact of M2 glycosylation on IAV replication. (A): a schematic overview of M2 domain structure; the glycosites were highlighted. The glycosite sequence on M2 was NDS. Reverse genetics was used to change N to G or S to I. (B): a chart showing the comparison of virus replication rates of MDCK cells infected with indicated IAV variants at a MOI of 0.01, using the plaque assay to determine viral titer 24 hours post infection. Mean±SEM of 3 independent experiments is shown.

DETAILED DESCRIPTION OF THE INVENTION

Figure 1:
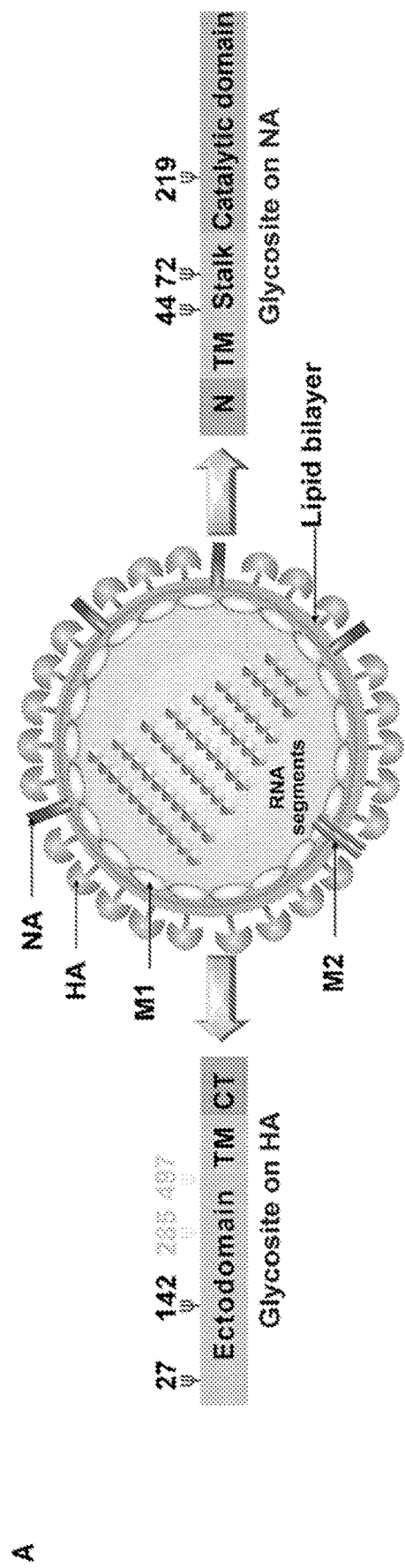
FIG. 1 includes diagrams showing the impact of glycosylation on immunogenicity of hemagglutinin (HA) on influenza A virus (IAV). (A): a schematic overview of glycosites (Ψ) on IAV surface proteins HA and neuraminidase (NA). CT: C-terminal cytoplasmic domain. TM: transmembrane domain. N: N-terminal cytoplasmic domain. (B): a chart showing the comparison of replication rates of viruses having different glycosylation patterns in MDCK cells. (C): a photo showing Western blot analysis of A549 cells infected with four variants of IAV as indicated, using anti-HA, anti-M1 and anti-β-actin antibodies. (D): a diagram showing HA binding patterns in a glycan array from wild-type (WT) and 142-G IAV strains. (E): a photo showing an hemagglutinination assay of IAV variants as indicated. (F): a diagram showing glycan array analysis of WT viruses having deglycosylated HA. (G): a diagram showing immunogenicity of WT IAV and IAV variants as indicated in mice, which were immunized with inactivated viruses, using a hemagglutination inhibition assay of the sera obtained from the immunized mice. (H): a diagram showing the survival rate of mice immunized with indicated virus and subsequently challenged with a lethal-dose of H5N1 virus. In panels (B), (D), and (F), Mean±standard error of the mean (SEM) for 3 independent experiments is shown; in panel (G), Mean±SEM for 10 independent experiments is shown; in panel (H), 10 independent experiments is shown. *: $P<0.001$. **: $P<0.05$.
Figure 1:
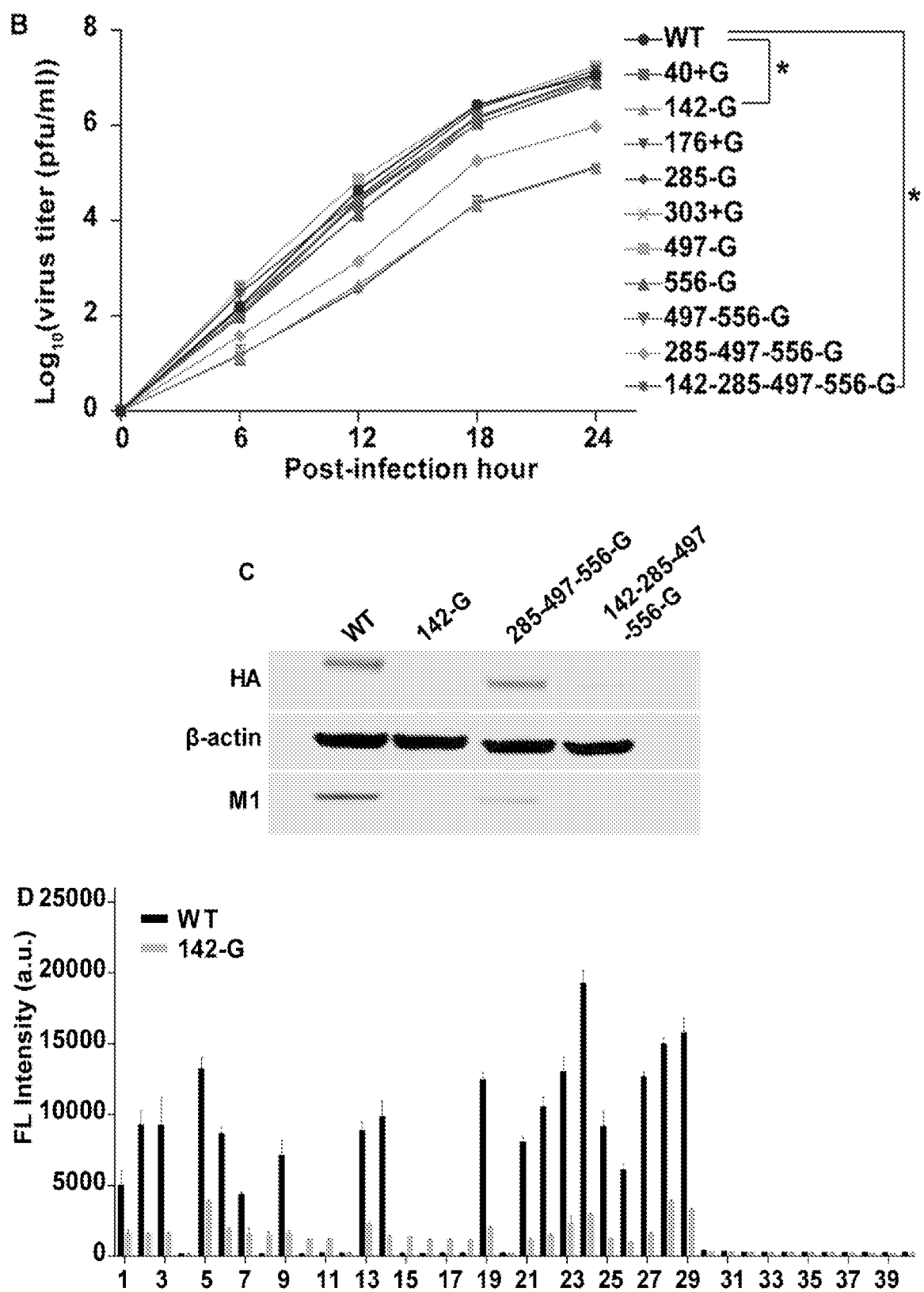
Figure 1:
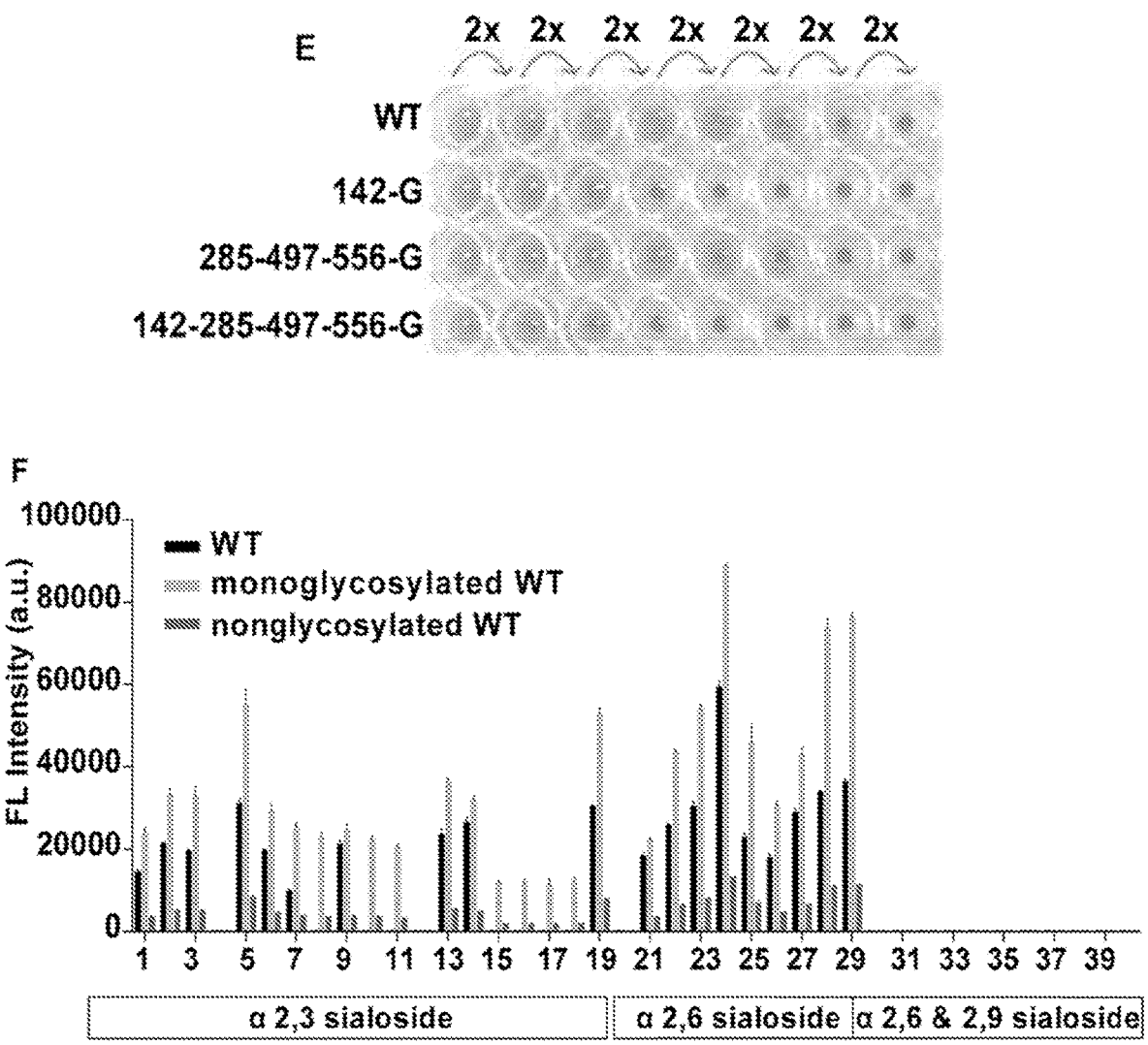
Figure 1:
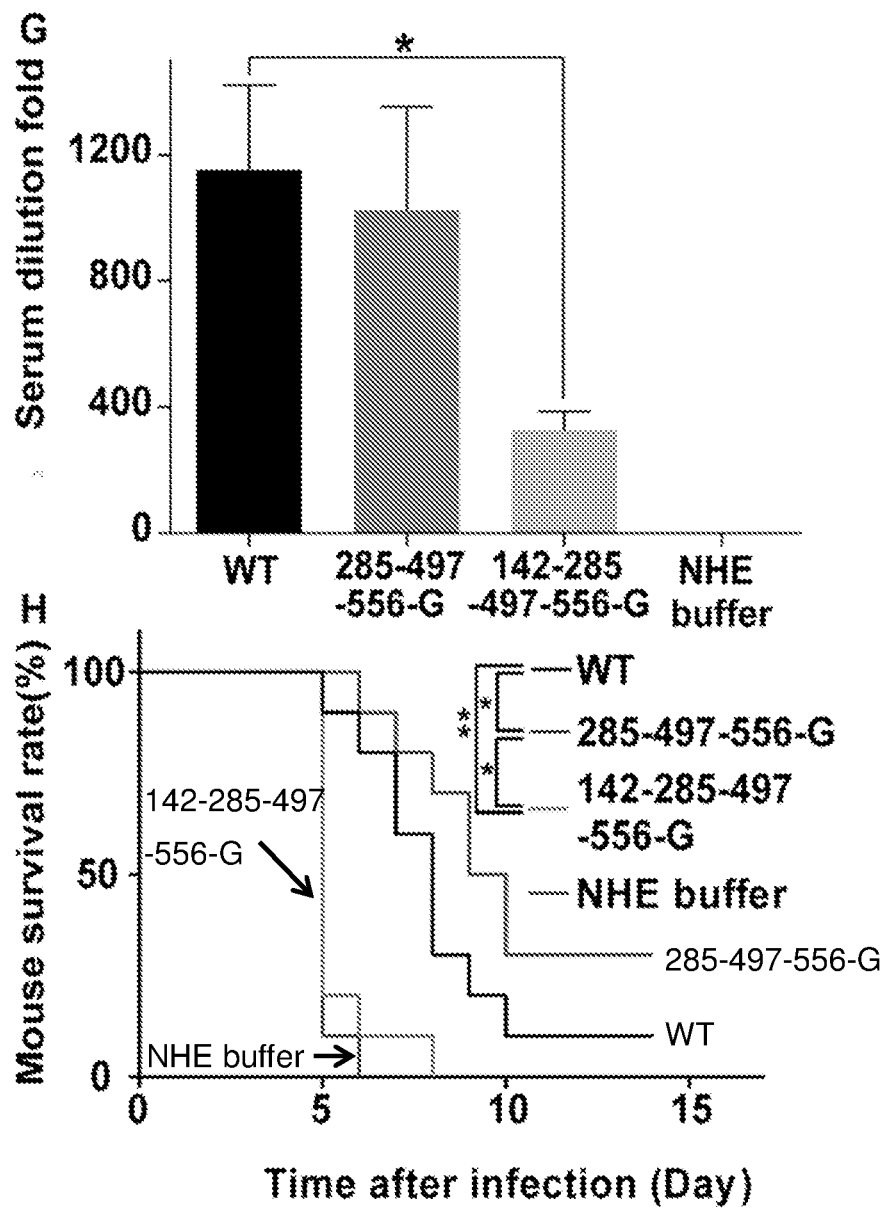

Recent development of universal influenza vaccines was focused on the use of conserved peptides or proteins as antigens with different adjuvants and administration methods to induce immune responses. Use of conserved peptides or proteins, however, often results in virulent viruses, which may raise safety concerns, and/or restricted immune responses against one influenza strain. The present disclosure aims to overcome these limitations via, in part, the development of hemagluttinin (HA) and neuraminidase (NA) immunopeptide variants with enhanced immunogenicity. Such HA and/or NA variants may induce immune responses against a broad spectrum of influenza virus strains and would be useful in making universal influenza vaccines.

Accordingly, provided herein are HA and NA variants having enhanced immunogenicity, influenza viral particles comprising such variants, immune compositions comprising influenza virus particles or HA/NA variants, and uses thereof for inducing immune responses against influenza virus.

I. Hemagglutinin (HA) Variants

Hemagglutinin (HA) is a glycoprotein found on the surface of influenza virus. HA is responsible for binding the virus to respiratory and erythrocyte cells, which have sialic acid on their cell membranes. HA proteins are often post-translationally modified through the addition of glycan to multiple asparagine residues in the consensus motif of Asn-Xaa-Ser/Thr (N-glycosylation). The Asn residues at which N-glycosylation occurs is referred to herein as glycosites or N-glycosylation sites.

As an example, the amino acid sequence of the wild-type HA from Influenza A virus (A/WSN/1933(H1N1) is provided as SEQ ID NO: 3 below. The glycosites (Asn or N residues) of this wild-type HA are in boldface.

```
                                       SEQ ID NO: 3
MKAFVLVLLY AFVATDADTI CIGYHANNST DTVDTIFEKN
                           27

VAVTHSVNLL EDRHNGKLCK LKGIAPLQLG KCNITGWLLG

NPECDSLLPA RSWSYIVETP NSENGACYPG DFIDYEELRE
```

-continued
```
QLSSVSSLER FEIFPKESSW PNHTFNGVTV SCSHRGKSSF
                       142

YRNLLWLTKK GDSYPKLTNS YVNNKGKEVL VLWGVHHPSS

SDEQQSLYSN GNAYVSVASS NYNRRFTPEI AARPKVKDQH

GRMNYYWTLL EPGDTIIFEA TGNLIAPWYA FALSRGFESG
                                           285

IITSNASMHE CNTKCQTPQG SINSNLPFQN IHPVTIGECP

KYVRSTKLRM VTGLRNIPSI QYRGLFGAIA GFIEGGWTGM

IDGWYGYHHQ NEQGSGYAAD QKSTQNAINR ITNKVNSVIE

KMNTQFTAVG KEFNNLEKRM ENLNKKVDDG FLDIWTYNAE

LLVLLENERT LDFHDLNVKN LYEKVKSQLK NNAKEIGNGC

FEFYHKCDNE CMESVRNGTY DYPKYSEESK LNREKIDGVK
                      497

LESMGVYQIL AIYSTVASSL VLLVSLGAIS FWMCSNGSLQ
                                        556

CRICI
```

Other wild-type HA antigens, e.g., H1, H2, or H3 HA antigens, were well known in the art and their amino acid sequences can be found in publically available gene databases, for example, GenBank. The glycosites of a particular wild-type HA subtype can be identified by comparing its amino acid sequence with the exemplary sequence, SEQ ID NO: 3, provided above.

The HA variants described here may be derived from any of the wild-type HA subtypes known in the art, e.g., H1, H2, or H3 HA antigens. Such an HA variant maintains one or more glycosites but has one or more of the other glycosites mutated such that no N-glycosylation occurs at the mutated sites (aglycosylated) as relative to the wild-type counterpart. For example, the HA variant described herein may retains the Asn residue (glycosite) at a position corresponding to residue 142 in SEQ ID NO:3 (same as residue 142 in SEQ ID NO:1 below) and optionally also retain the Asn residue at a position corresponding to residue 27 in SEQ ID NO:3 (same as residue 27 in SEQ ID NO:1 below), while having one or more of the Asn residues at positions corresponding to residues 285, 497 and 556 in SEQ ID NO: 3 (same as residues 285, 497, and 556 in SEQ ID NO:1 below) mutated. Thus, the HA variants described herein may be glycosylated at the Asn residue corresponding to position 142 and optionally position 27 in SEQ ID NO:3 (or SEQ ID NO:1), while being aglycosylated at the mutated glycosites corresponding to positions 285, 497 and/or 556 in SEQ ID NO: 3 (or SEQ ID NO:1).

The term "mutated" or "mutation" may refer to any type of mutations, for example, addition, deletion and amino acid substitutions. In some instances, the one or more Asn residues corresponding to positions 285, 497 and 556 in SEQ ID NO: 3 or SEQ ID NO:1 may be deleted. In other instances, one or more of these Asn residues can be substituted by another amino acid residue (e.g., Ala or Gly). In some examples, the HA variants described herein may have one of the three glycosites mutated. In other examples, the HA variants may have two of the three glycosites mutated, e.g., 285+497, 285+556, or 497+556. In another example, all of the three glycosites are mutated (e.g., substituted).

"A residue in sequence X corresponding to position a in sequence Y" refers to the residue at the counterpart position of a in sequence X when sequences X and Y are aligned using an amino acid sequence alignment tools known in the art, for example, BLAST®.

The amino acid sequence of an exemplary HA variant as described herein is provided below. Other exemplary HA variants are provided elsewhere in the present disclosure, for example, in Examples below.

(HA 285-497-556-G)

SEQ ID NO: 1

```
MKAFVLVLLY AFVATDADTI CIGYHANNST DTVDTIFEKN
                              27
VAVTHSVNLL EDRHNGKLCK LKGIAPLQLG KCNITGWLLG
NPECDSLLPA RSWSYIVETP NSENGACYPG DFIDYEELRE
QLSSVSSLER FEIFPKESSW PNHTFNGVTV SCSHRGKSSF
                       142
YRNLLWLTKK GDSYPKLTNS YVNNKGKEVL VLWGVHHPSS
SDEQQSLYSN GNAYVSVASS NYNRRFTPEI AARPKVKDQH
GRMNYYWTLL EPGDTIIFEA TGNLIAPWYA FALSRGFESG
                                          285
IITSAASMHE CNTKCQTPQG SINSNLPFQN IHPVTIGECP
KYVRSTKLRM VTGLRNIPSI QYRGLFGAIA GFIEGGWTGM
IDGWYGYHHQ NEQGSGYAAD QKSTQNAINR ITNKVNSVIE
KMNTQFTAVG KEFNNLEKRM ENLNKKVDDG FLDIWTYNAE
LLVLLENERT LDFHDLNVKN LYEKVKSQLK NNAKEIGNGC
FEFYHKCDNE CMESVRAGTY DYPKYSEESK LNREKIDGVK
              497
LESMGVYQIL AIYSTVASSL VLLVSLGAIS FWMCSAGSLQ
                                         556
CRICI
```

The HA variants may include amino acid sequences at least 85% (e.g., 90%, 95%, 97%, 98%, or 99%) identical to a wild-type HA antigen (e.g., SEQ ID NO:3) and contain the glycosite mutations as noted above. The term "sequence identity," as known in the art, refers to a relationship between the sequences of two polypeptides, as determined by sequence comparison (alignment). In the art, identity also means the degree of sequence relatedness between two sequences as determined by the number of matches between strings of two or more amino acid residues. Identity measures the percent of identical matches between the smaller of two or more sequences with gap alignments (if any) addressed by a particular mathematical model or computer program (e.g., "algorithms"). Identity of related peptides can be readily calculated by known methods. The "percent identity" of two amino acid sequences can be determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST® and XBLAST® programs (version 2.0) of Altschul, et al. J. Mol. Biol. 215:403-10, 1990. BLAST® protein searches can be performed with the XBLAST program, score=50, word-length=3 to obtain amino acid sequences homologous to the protein molecules of the invention. Where gaps exist between two sequences, Gapped BLAST® can be utilized as described in Altschul et al., Nucleic Acids Res. 25(17):3389-3402, 1997. When utilizing BLAST® and Gapped BLAST® programs, the default parameters of the respective programs (e.g., XBLAST® and NBLAST®) can be used. Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently, a Fast Optimal Global Sequence Alignment Algorithm (FOGSAA) was developed that purportedly produces global alignment of nucleotide and protein sequences faster than other optimal global alignment methods, including the Needleman-Wunsch algorithm.

In addition to the glycosite mutations described herein, the HA variants described herein may contain one or more conservative amino acid substitutions relative to its wild-type counterpart. The skilled artisan will realize that conservative amino acid substitutions may be made in HA variants to provide functionally equivalent variants, i.e., the variants retain the functional capabilities of the particular HA variant. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

To make an HA variant as described herein, a wild-type HA subtype antigen of interest can be selected and its glycosites corresponding to those noted above can be identified via conventional amino acid sequence alignment. Mutations (e.g., amino acid residue substitutions) can then be introduced into the coding sequence of the wild-type HA at one or more of the glycosites corresponding to positions 285, 497 and 556 in SEQ ID NO: 3 or SEQ ID NO:1 to obtain a coding sequence of the HA variant.

A coding sequence of any of the HA variants described herein may be incorporated into an expression vector for producing the HA variants via the conventional recombinant technology. In some instances, the coding sequence of the HA variant can be inserted into a viral vector for producing an influenza A viral particle that comprises the HA variant.

II. Neuraminidase (NA) Variants

Neuraminidase (NA) is a glycoprotein found on the surface of influenza virus. NA enzymatically cleaves sialic acid on respiratory and erythrocyte host cells to facilitate the release of viral particles and promote infection of additional cells.

NA protein comprises an N-terminal domain, a transmembrane domain, a stalk domain and a catalytic domain. Similar to HA proteins, NA protein are often post-translationally modified through N-glycosylation at glycosites. NA protein also comprises several "active site" residues, which are required for its catalytic activity.

As an example, the amino acid sequence of a wild-type NA from Influenza A virus strain (A/WSN/1933(H1N1)) is provided as SEQ ID NO: 4 below.

```
                                              SEQ ID NO: 4
MNPNQKIITI GSICMVVGII SLILQIGNII SIWISHSIQT

GNQNHTGICN QGSITYKVVA GQDSTSVILT GNSSLCPIRG
  44                                72

WAIHSKDNGI RIGSKGDVFV IREPFISCSH LECRTFFLTQ
                102

GALLNDKHSR GTFKDRSPYR ALMSCPVGEA PSPYNSRFES
                135

VAWSASACHD GMGWLTIGIS GPDDGAVAVL KYNGIITETI

KSWRKNILRT QESECTCVNG SCFTIMTDGP SDGLASYKIF
                    219

KIEKGKVTKS IELNAPNSHY EECSCYPDTG KVMCVCRDNW
                         262                277

HGSNRPWVSF DQNLDYKIGY ICSGVFGDNP RPKDGTGSCG

PVSADGANGV KGFSYKYGNG VWIGRTKSDS SRHGFEMIWD
                                        352

PNGWTETDSR FSMRQDVVAM TDRSGYSGSF VQHPELTGLD
                              386

CMRPCFWVEL IRGLPEENAI WTSGSIISFC GVNSDTVDWS
409

WPDGAELPFT IDK.
```

Residues 44, 72 and 219 of this wild-type NA (indicated in SEQ ID NO:4) above) are glycosites (Asn or N residues) and are in boldface. Residues 102R, 135D, 262E, 277R, 352R, 386Y and 409E (indicated in SEQ ID NO:4 above) are exemplary active sites and are in boldface. The N-terminal and transmembrane domains (SEQ ID NO:5 provided below) are indicated in italic type in SEQ ID NO: 4. The stalk domain (SEQ ID NO:6 provided below) of this wild-type NA is underlined in SEQ ID NO: 4. The catalytic domain (SEQ ID NO:7 provided below) is located at the C-terminus of this wild-type NA

```
N-TM domains (SEQ ID NO: 5):
MNPNQKIITI GSICMVVGII SLILQIGNI

Stalk domain (SEQ ID NO: 6):
I SIWISHSIQT GNQNHTGICN QGSITYKVVA GQDSTSVILT GNSS

Catalytic domain (SEQ ID NO: 7; active site
residues in boldface):
    LCPIRG WAIHSKDNGI RIGSKGDVFV IREPFISCSH

LECRTFFLTQ GALLNDKHSR GTFKDRSPYR ALMSCPVGEA

PSPYNSRFES VAWSASACHD GMGWLTIGIS GPDDGAVAVL

KYNGIITETI KSWRKNILRT QESECTCVNG SCFTIMTDGP

SDGLASYKIF KIEKGKVTKS IELNAPNSHY EECSCYPDTG

KVMCVCRDNW HGSNRPWVSF DQNLDYKIGY ICSGVFGDNP

RPKDGTGSCG PVSADGANGV KGFSYKYGNG VWIGRTKSDS

SRHGFEMIWD PNGWTETDSR FSMRQDVVAM TDRSGYSGSF

VQHPELTGLD CMRPCFWVEL IRGLPEENAI WTSGSIISFC

GVNSDTVDWS WPDGATLPFT IDK.
```

Other wild-type NA subtypes, e.g. N1, N2 or N3, are well-known in the art and their amino acid sequences can be found in publically available gene databases, for example, GenBank. The glycosites of a wild-type NA protein and the functional domains noted above (e.g., N-terminal and transmembrane domains, stalk domain, and catalytic domain), as well as the active sites/residues in the catalytic domain, can be identified by comparing its amino acid sequence with the exemplary sequence, SEQ ID NO: 4, provided above.

The NA variants described herein may be derived from any of the wild-type NA subtypes known in the art, e.g. N1, N2 or N3 NA subtypes. Such a NA variant may have a mutation (e.g., addition, deletion, or amino acid substitutions) in one or more active site and/or in one or more N-glycosylation sites such that the variant is defective in NA activity relative to its wild-type counterpart. "Defective" in regards to the activity of the NA variants described herein means that the biological activity of the NA variant is substantially reduced as compared with the wild-type counterpart, for example, the activity of the NA variants may be less than 30% (e.g., less than 20%, less than 10% or less than 5%) relative to that of the wild-type counterpart as determined by the same or a substantially similar assay under the same or substantially similar conditions. In some examples, the biological activity of the NA variants described herein may be at an undetectable level as measured by a conventional assay and/or assays described herein.

NA activity may be measured with an 2-(4-methylumbelliferyl)-α-D-N-acetylneuraminic acid (4-MUNANA) fluorescence-based assay (as indicated in Example 2 below), which is well-known in the art. Other measurements of NA activity include assays that determine NA substrate specificity. For example, 4-Muα-NeuAc, 6'-sialyl-N-acetyllactosamine (6-SLN), 3'-sialyl-N-acetyllactosamine (3-SLN), 3'-sialyllactose (3-SL) and 6'-sialyllactose (6-SL) may be used to determine NA substrate specificity. The kinetics of enzymatic cleavage of substrates by NA may be determined by reaction with N-acetylmannosamine (ManNAc) dehydrogenase and sialic acid aldolase (as indicated in Example 2 below).

In some instances, the NA variant described herein may have one or more mutations at one or more N-glycosylation sites (e.g., those noted herein), which may be identified via conventional methods and/or following the disclosures herein. Exemplary N-glycosylation sites include positions (Asn residues) corresponding to 44, 72 and 219 in SEQ ID NO: 4. For example, one or more of N-glycosylation sites (e.g., 44, 72 and/or 219) can be deleted. In other instances, one or more of these N-glycosylation sites can be substituted by another amino acid (e.g., Ala or Gly). In some examples, the NA variants described herein may have substitution at one glycosite (e.g., 44, 72 or 219). In other examples, the NA variants may have a substitution at two glycosites (e.g., 44+72, 72+219 or 44+219). In another example, three glycosites are substituted (e.g. 44+72+219).

The amino acid sequences of exemplary NA variants having one or more mutated glycosites are described herein is provided below. Amino acid substitutions compared to its wild-type counterpart are in boldface:

```
NA 44-G (SEQ ID NO: 8, substitution at position 44
in boldface):
MNPNQKIITI GSICMVVGII SLILQIGNII SIWISHSIQT

GNQAHTGICN QGSITYKVVA GQDSTSVILT GNSSLCPIRG
  44
```

WAIHSKDNGI RIGSKGDVFV IREPFISCSH LECRTFFLTQ

GALLNDKHSR GTFKDRSPYR ALMSCPVGEA PSPYNSRFES

VAWSASACHD GMGWLTIGIS GPDDGAVAVL KYNGIITETI

KSWRKNILRT QESECTCVNG SCFTIMTDGP SDGLASYKIF

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSGSF VQHPELTGLD

CMRPCFWVEL IRGLPEENAI WTSGSIISFC GVNSDTVDWS

WPDGAELPFT IDK.

NA 72-G (SEQ ID NO: 9, substitution at position 72 in boldface)
MNPNQKIITI GSICMVVGII SLILQIGNI<u>I</u> <u>SIWISHSIQT</u>

GNQNHTGICN QGSITYKVVA <u>GQDSTSVILT</u> <u>GA</u>SSLCPIRG
                 72

WAIHSKDNGI RIGSKGDVFV I<u>R</u>EPFISCSH LECRTFFLTQ

GALLNDKHSR GTFKDRSPYR ALMSCPVGEA PSPYNSRFES

VAWSASACHD GMGWLTIGIS GPDDGAVAVL KYNGIITETI

KSWRKNILRT QESECTCVNG SCFTIMTDGP SDGLASYKIF

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSGSF VQHPELTGLD

CMRPCFWVEL IRGLPEENAI WTSGSIISFC GVNSDTVDWS

WPDGAELPFT IDK.

NA 44-72-G (SEQ ID NO: 10, substitutions at positions 44 and 72 in boldface)
MNPNQKIITI GSICMVVGII SLILQIGNI<u>I</u> <u>SIWISHSIQT</u>
                 44

GNQAHTGICN QGSITYKVVA <u>GQDSTSVILT</u> <u>GA</u>SSLCPIRG
                 72

WAIHSKDNGI RIGSKGDVFV IREPFISCSH LECRTFFLTQ

GALLNDKHSR GTFKDRSPYR ALMSCPVGEA PSPYNSRFES

VAWSASACHD GMGWLTIGIS GPDDGAVAVL KYNGIITETI

KSWRKNILRT QESECTCVNG SCFTIMTDGP SDGLASYKIF

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSGSF VQHPELTGLD

CMRPCFWVEL IRGLPEENAI WTSGSIISFC GVNSDTVDWS

WPDGAELPFT IDK.

NA 44-72-219-G (SEQ ID NO: 11, substitutions at positions 44, 72, and 219 in boldface):
MNPNQKIITI GSICMVVGII SLILQIGNII SIWISHSIQT

GNQAHTGICN QGSITYKVVA GQDSTSVILT GASSLCPIRG
  44                72

WAIHSKDNGI RIGSKGDVFV IREPFISCSH LECRTFFLTQ

GALLNDKHSR GTFKDRSPYR ALMSCPVGEA PSPYNSRFES

VAWSASACHD GMGWLTIGIS GPDDGAVAVL KYNGIITETI

KSWRKNILRT QESECTCVAG SCFTIMTDGP SDGLASYKIF
         219

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSGSF VQHPELTGLD

CMRPCFWVEL IRGLPEENAI WTSGSIISFC GVNSDTVDWS

WPDGAELPFT IDK.

Alternatively or in addition, the NA variants described herein may have one or more mutations (e.g., deletion, addition, or amino acid substitutions) at one or more of the active sites as known in the art and/or described herein. Exemplary active sites include positions corresponding to 102, 135, 262, 277, 352, 386 and 409 in SEQ ID NO:4. For example, the NA variant may have the positions corresponding to residue 102 and/or 135 in SEQ ID NO:4 substituted by another amino acid (e.g. Ala or Gly).

The amino acid sequences of two exemplary NA variants having mutated active sites are provided below. Amino acid substitutions as compared to a wild-type counterpart are in boldface:

WSN-NA AS1 (SEQ ID NO: 12, substitution at position 102 indicated in boldface)
MNPNQKIITI GSICMVVGII SLILQIGNII SIWISHSIQT

GNQNHTGICN QGSITYKVVA GQDSTSVILT GNSSLCPIRG

WAIHSKDNGI RIGSKGDVFV IAEPFISCSH LECRTFFLTQ
            102

GALLNDKHSR GTFKDRSPYR ALMSCPVGEA PSPYNSRFES

VAWSASACHD GMGWLTIGIS GPDDGAVAVL KYNGIITETI

KSWRKNILRT QESECTCVNG SCFTIMTDGP SDGLASYKIF

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSGSF VQHPELTGLD

CMRPCFWVEL IRGLPEENAI WTSGSIISFC GVNSDTVDWS

WPDGAELPFT IDK

WSN-NA AS2 (SEQ ID NO: 13, substitution at position 135 indicated in boldface)
MNPNQKIITI GSICMVVGII SLILQIGNII SIWISHSIQT

GNQNHTGICN QGSITYKVVA GQDSTSVILT GNSSLCPIRG

```
                                    -continued
WAIHSKDNGI RIGSKGDVFV IREPFISCSH LECRTFFLTQ

GALLNDKHSR GTFKARSPYR ALMSCPVGEA PSPYNSRFES
                135

VAWSASACHD GMGWLTIGIS GPDDGAVAVL KYNGIITETI

KSWRKNILRT QESECTCVNG SCFTIMTDGP SDGLASYKIF

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSGSF VQHPELTGLD

CMRPCFWVEL IRGLPEENAI WTSGSIISFC GVNSDTVDWS

WPDGAELPFT IDK

WSN-NA-G388A (SEQ ID NO: 14, substitution at posi-
tion 388 indicated in boldface)
MNPNQKIITI GSICMVVGII SLILQIGNII SIWISHSIQT

GNQNHTGICN QGSITYKVVA GQDSTSVILT GNSSLCPIRG

WAIHSKDNGI RIGSKGDVFV IREPFISCSH LECRTFFLTQ

GALLNDKHSR GTFKDRSPYR ALMSCPVGEA PSPYNSRFES

VAWSASACHD GMGWLTIGIS GPDDGAVAVL KYNGIITETI

KSWRKNILRT QESECTCVNG SCFTIMTDGP SDGLASYKIF

KIEKGKVTKS IELNAPNSHY EECSCYPDTG KVMCVCRDNW

HGSNRPWVSF DQNLDYKIGY ICSGVFGDNP RPKDGTGSCG

PVSADGANGV KGFSYKYGNG VWIGRTKSDS SRHGFEMIWD

PNGWTETDSR FSMRQDVVAM TDRSGYSASF VQHPELTGLD
                                   388

CMRPCFWVEL IRGLPEENAI WTSGSIISFC GVNSDTVDWS

WPDGAELPFT IDK
```

In some examples, the NA variants described herein may comprise amino acid sequences at least 85% (e.g., 90%, 95%, 97%, 98% or 99%) identical to that of a wild-type NA protein, for example, SEQ ID NO: 4. Such a variant may contain one or more mutations at one or more glycosites and/or one or more mutations at one or more active sites as described herein. In addition, the NA variants may further comprise one or more amino acid substitutions, for example, conservative amino acid residue substitutions, at suitable positions, e.g., the position corresponding to 388 in SEQ ID NO:4.

In some embodiments, the NA variant described herein may be a truncated form of a wild-type NA, having the stalk region or a portion thereof, the catalytic domain or a portion thereof, or both deleted. In other instances, the NA variant may have a partial deletion in the stalk region and/or a partial deletion in the catalytic domain that results in loss of one or more active sites. Alternatively or in addition, the NA variant may have a partial deletion in the stalk region and/or a partial deletion in the catalytic domain that results in loss of one or more glycosylation sites. In one example, the NA variant may have a deletion of the entire catalytic domain (e.g. a region corresponding to residue 75 through residue 453 in SEQ ID NO: 4). In another example, a NA variant may have both the catalytic domain and the stalk region deleted (e.g. loss of residues corresponding to residue 30 through residue 453 in SEQ ID NO: 4).

The amino acid sequences of two exemplary truncated NA variants as described herein are provided below:

```
LAIV WSN-NA (SEQ ID NO: 2; having both the stalk
and catalytic domains deleted):
MNPNQKIITI GSICMVVGII SLILQIGNII WSN-NA-CD (SEQ ID NO: 15; having the catalytic
domain deleted):
MNPNQKIITI GSICMVVGII SLILQIGNII SIWISHSIQT

GNQNHTGICN QGSITYKVVA GQDSTSVILT GNSS
```

To make any of the NA variants as described herein, a wild-type NA subtype protein of interest can be selected and its glycosites and/or active sites corresponding to those noted above can be identified via conventional amino acid sequence alignment. Mutations (e.g., amino acid residue substitutions or deletions) can then be introduced into the coding sequence of the wild-type NA at one or more glycosite and/or active sites. For example, site-directed mutagenesis or CRISPR can be used to generate a mutation of interest. In another example, a stop codon may be incorporated into the coding sequence of an NA protein at a desired position for producing a truncated NA variant as described herein.

A coding sequence of any of the NA variants described herein can be inserted into avector such as a viral vector for producing an Influenza A viral particle that comprises the NA variant via conventional technology.

III. Influenza Viral Particles

Also described herein are influenza A viral (IAV) particles comprising any of the HA variants and/or any of the NA variants described herein. The IAV particle described herein may be of any influenza A virus subtype. It may be a live (viable) attenuated virus or a defective virus.

An influenza A virus subtype may be characterized by a hemagglutinin (HA) viral surf ace protein, and thus are labeled by an H number, such as, for example, H1, H3, and H5. In addition, the subtypes may be further characterized by a neuraminidase (NA) viral surface protein, indicated by an N number, such as, for example, N1 and N2. As such, a subtype may be referred to by both H and N numbers, such as, for example, H1N1, H5N1, and H5N2. A H1N1 IAV is a subtype that has a H1 HA protein and a N1 NA protein. As another example, an H5N1 IAV is a subtype that has H5 HA protein and N1 NA protein.

A live attenuated virus refers to a virus that is modified (e.g., genetically, chemically, or physically) in a manner that renders it less virulent relative to its wild-type counterpart. Typically, a live attenuated virus is capable of self-replication and assembly in a suitable host cell. For example, the virulence of the live attenuated recombinant virus may be 50% (e.g., 40%, 30%, 20%, 10%, or less) of that of the wild-type counterpart as determined by the same or a substantially similar assay under the same or substantially similar conditions. In some examples, the live attenuated virus may be completely inactivated, i.e., its virulence is undetectable by a conventional assay or an assay described herein. Attenuation may be attributable to the one or more mutations introduced into either the HA antigen or the NA antigen. For example, glycosylation of HA at the glycosite corresponding to 142 in SEQ ID NO:1 or SEQ ID NO:3 ("the 142 glycosite") and optionally also at the glycosite at the position corresponding to 27 in SEQ ID NO:1 or SEQ ID NO:3 ("the 27 glycosite") would be important to the bioactivity of HA, which may contribute to the virulence of an IAV carrying such an HA. Accordingly, IAV carrying an HA molecule which is glycosylated at the 142 glycosite and optionally at the 27 glycosite may need to be attenuated or inactivated via a conventional method (e.g., those known in the art and/or disclosed herein) for safety concerns. Mutations at one or more of the glycosites at positions corresponding to 285, 497 and 556 in SEQ ID NO: 1 or SEQ ID NO: 3 to eliminate glycosylation at one or more of these sites can enhance immunogenicity of such IAV particles, which may due to the enhanced exposure of conserved regions of HA to the immune system of a host. However, mutations at these glycosites have little or no impact on virus replication rates. See Examples below and also Wu et al., PNAS 114(2):280-285, 2017.

In other embodiments, the IAV virus described herein may be a defective virus, which is unable to self-replicate and/or assemble in a suitable host cell in the absence of a help virus or essential viral components for replication and/or viral particle assembly. For example, IAV particles comprising the NA variants described herein, which lack the neuraminidase enzymatic activity, would be defective in at least viral particle assembly. IAV particles comprising such an NA variants can be produced in the presence of a functional NA. These IAV particles are advantageous candidates for preparing live attenuated influenza vaccine compositions as they may activate IAV-specific $CD8^+$ T cells that can recognize various influenza virus strains and subtypes in the absence of neutralizing antibodies. See Examples below and also Wu et al., 2017.

Viral virulence may be determined by viral replication rate, viral entry, and/or subject (host) survival rate after infection with a virus. As described in Example 1, viral replicate rate can be determined using a plaque assay, which measures viral titer. Viral entry may be measured with an infectivity assay (described in Example 1). An exemplary host survival assay is provided in Example 1. Examples of subjects include human, mouse, pig, cow, rat, dog, guinea pig, hamster, rabbit, cat, goat, sheep, monkey, horse or bird.

A live attenuated virus may be generated through methods well-known in the art, such as passaging of a virus in tissue culture or on eggs for multiple generations to identify less virulent strains. A live attenuated virus may also be generated through chemical and/or physical treatment.

In some instances, a suitable host cell line (e.g., HEK293T, MDCK, A549, CHO or Vero cells) may be used for producing the IAV particles disclosure herein following routine practice. One or more expression vectors (e.g., viral vectors) encoding viral components, including one or more of the HA and/or NA variants described herein may be introduced into the suitable host cells, which can then be cultured under suitable conditions allowing for production of the IAV particles. When needed, a helper virus can be used to facilitate replication and/or assembly of the IAV particles. Alternatively, a host cell line producing one or more of essential viral components for viral genome replication and/or viral particle reassemble may be used. The supernatant of the cell culture may be collected and the viral particles contained therein can be collected via routine methodology. The viral particles thus obtained may be used for further proliferation in a suitable host (e.g., host cells or chick egg such as Specific Pathogen-Free (SPF) chicken eggs) using methods known in the art or disclosed herein.

In some examples, the IAV particles may further be attenuated by chemical or physical methods known in the art. For example, a virus may be inactivated using a chemical treatment, including, but not limited to, formaldehyde, betapropiolactone (BPL), binary ethylenimine (BEI), merthiolate, glutaraldehyde, sodium dodecyl sulfate, or a combination thereof. Alternatively or in addition, a virus may be inactivated by heat, UV irradiation, extreme pH, and freeze-thaw cycles or other methods well-known in the art.

Optionally, the recombinant IAV is suspended in a diluent for further use. Non-limiting examples of the diluent include, water, saline, dextrose, propanol, ethanol, mannitol, sorbitol, lactose, starch, lactitol, maltodextrin, glycerol, xylitol, trehalose, mineral oil, vegetable oil, sodium chloride, sodium carbonate, sodium bicarbonate, potassium chloride, dicalcium phosphate, calcium carbonate, calcium sulphate dehydrate, and magnesium carbonate.

Immunogenic Compositions

In some aspects, the present disclosure features an immunogenic composition (e.g. a vaccine) comprising (i) any of the recombinant IAV viruses, or any of the HA and/or NA variants described herein, and (ii) a pharmaceutically acceptable carrier, which may be an adjuvant. As used herein, "immunogenic composition" may refer to a composition, which, when inoculated into a host, has the effect of stimulating an immune response in the host and serves to fully or partially protect the host against a disease (e.g. IAV infection) or reducing its symptoms (e.g. fever, congestion and/or headaches). In some embodiments, the immunogenic composition described herein comprises an IAV particle as described herein. In other embodiments, the immunogenic composition described herein comprises any of the HA variants and/or NA variants as described herein. Such an immunogenic composition may be used as a prophylactic or as a therapeutic agent for treating an existing condition.

The term "antigen" or antigenic agent," as used herein, unless indicated otherwise, may indicate any agent that, when introduced into an immunocompetent human or animal, stimulates a humoral and/or cellular immune response. The antigen may be a pure substance, a mixture of substances, or particular material or a live, attenuated, virus. Examples of suitable antigens include a protein, glycoprotein, polypeptide, and a virus.

Immune responses elicited by an immunogenic composition as described herein may be monitored via routine practice. For example, an immune response may be measured by determining CD8+ T cell induction against an antigen, using antibody-profiling technologies (e.g. enzyme linked immunosorbent assay (ELISA), enzyme immunoassay (EIA), or radio immunoassay (RIA), cytotoxic T-lymphocyte assays and/or other methods well-known in the art.

The immunogenic composition can be prepared via conventional methods. Examples of pharmaceutically acceptable carriers include phosphate buffered saline, a bicarbonate solution, and/or an adjuvant. The carrier may be selected on the basis of the mode and route of administration, and standard pharmaceutical practice. Suitable pharmaceutical carriers and diluents, as well as pharmaceutical necessities for their use, are described in Remington's Pharmaceutical Sciences, 18th edition, Mack Publishing Co., Easton, Pa. (1990). The composition can also include a polymer that facilitates in vivo delivery. See Audran R. et al. Vaccine 21:1250-5, 2003; and Denis-Mize et al. Cell Immunol., 225:12-20, 2003.

As used herein, "adjuvant" may refer to any substance or mixture of substances that enhances, increases, upwardly modulates, diversifies or otherwise facilitates the immune response (e.g. humoral or cellular immune response) to an antigen. For example, the adjuvant may include complete Freund's adjuvant (FA), incomplete Freund's adjuvant (IFA), mineral gel (e.g. aluminum hydroxide or aluminum phosphate), surface active substance (e.g. lysolecithin), pluronic polyol, polyanion, peptide, oil emulsion, hydrocarbon emulsion, keyhole limpet hemocyanin, sulfolipo-cyclodextrin (SL-CD), and saponin (e.g. Quil A). In other examples, the adjuvant may be cholera toxin, *Escherichia coli* heat-labile enterotoxin (LT), liposome, immune-stimulating complex (ISCOM), or immunostimulatory sequences oligodeoxynucleotides (ISS-ODN), if necessary.

As known to a person of ordinary skill in the art, the immunogenic composition may further comprise a pH adjuster, which may be acetic acid, boric acid, carbonic acid, chromic acid, citric acid, lactic acid, hydrochloric acid, tartaric acid, propionic acid, malic acid, phosphoric acid, ammonium hydroxide, ammonium carbonate, ethylamine, dimethylamine, glycine, methylamine, trimethylamine, diethanolamine, sodium bicarbonate, sodium borate, sodium hydroxide, hydrazine, monoethanolamine, potassium hydroxide, sodium phosphate, trolamine, or the combination thereof.

In some examples, the present immunogenic composition may further comprise a preservative. Suitable examples of preservative include, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, and the combination thereof.

Methods for preparing immunogenic compositions such as vaccines are generally well known in the art, as exemplified by U.S. Pat. Nos. 4,601,903; 4,599,231; 4,599,230; and 4,596,792. Vaccines may be prepared as injectables, as liquid solutions or emulsions. The recombinant viruses or HA peptides of this invention may optionally be mixed with physiologically acceptable and excipients compatible. Excipients may include, water, saline, dextrose, glycerol, ethanol, and combinations thereof. The vaccine may contain minor amounts of auxiliary substances such as wetting or emulsifying agents, pH buffering agents, or an adjuvant to enhance the effectiveness of the vaccines. Methods of achieving adjuvant effect for immunogenic compositions include use of agents, such as aluminum hydroxide or phosphate (alum), commonly used as 0.05 to 0.1 percent solutions in phosphate buffered saline.

The pharmaceutical compositions described herein can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical composition containing the IAV particles or the HA and/or NA variants and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Therapeutic Applications

Any of the immunogenic compositions described herein may be used for treating influenza virus infection or for reducing the risk of such infection. Without being bound by the theory, the protection conferred by the present method may be partly mediated by an IAV-specific or HA/NA-specific $CD8^+$ T cell response against the corresponding IAV virus, which then provides cross-strain and/or cross-subtype protection in the subject.

To practice this embodiment, an effective amount of the immunogenic composition described herein may be administered to a subject who needs the treatment via a suitable route. The subject to be treated by the method described herein may be a mammal (e.g., human, mouse, pig, cow, rat, dog, guinea pig, hamster, rabbit, cat, goat, sheep, monkey, horse or bird) who is suffering from influenza A virus infection, suspected of having the infection, or at risk for the infection.

The term "an effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents. The quantity to be administered depends on the subject to be treated, including, for example, the capacity of the individual's immune system to synthesize antibodies, and if needed to produce a cell-mediated immune response. Precise mounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

The immunogenic composition described herein may be administered to a subject (e.g. human) to reduce the risk of having influenza virus infection (prophylactic treatment) or to treating influenza virus infection, which may be caused by any type of influenza A virus (e.g., H1N1, H1N2, H2N2, H3N2, H5N1, H5N2, H7N2, H7N3, H7N7, H9N2 or H10N7). In some embodiments, immunogenic compositions comprising an IAV derived from a particular influenza virus subtype or an HA and/or NA variant derived from the particular type of the virus may be used for treating or reducing the risk of infection caused by that particular influenza virus subtype. The term "treating" as used herein refers to the application or administration of a composition including one or more active agents to a subject, who has influenza virus infection, a symptom of the infection, or a predisposition toward the infection, with the purpose to cure, heal, alleviate, relieve, alter, remedy, ameliorate, improve, or affect the infection, the symptoms of the infection, or the predisposition toward the infection.

In some embodiments, the subject to be treated by the method described herein may be a human patient having infection caused by influenza virus as diagnosed by routine medical practice. In other embodiments, the subject may be a human patient exhibiting one or more symptoms associated with influenza virus infection, for example, fever, aching muscles, chills and sweats, headache, cough, fatigue and weakness, nasal congestion, and/or sore throat. Such a human patient may have exposure to IAV.

In some instances, the human subject may be at risk for infection; for example, the individual may be immunocompromised (e.g. suffer from HIV/AIDS, asthma, chronic heart disease, chronic heart or lung disease), may be of old age (e.g. older than 65 years), may be a child or infant (e.g. less than 5 years old), or may work/live in close proximity to infected individuals.

Any immunogenic compositions described in the present disclosure may be administered to a subject in need of the treatment via a suitable route, for example, parenterally, by injection or implantation subcutaneously, intramuscularly, intrathecally, intraperitoneally, intracuteanously, intrasternally, intraarticularlly, intracranially, intralesionally intrarectually, intravaginally, intranasally, intragastically, intratracheally, or intrapulmonarily. Alternatively, other modes of administration including suppositories, oral formulations, enteral, nasal, topical or transmucosal administration may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders. In some instances, the immunogenic composition described herein may be administered to the subject via nasal administration that functions as a universal influenza vaccine (e.g. an influenza vaccine that has cross-species, cross-strain and/or cross lineage specificity).

As mentioned above, the dosage required depends on the choice of the route of administration; the nature of the formulation; the nature of the subject's illness; the subject's species, size, weight, surface area, age, and sex; other drugs being administered; and the judgment of the practitioner. Suitable dosages are in the range of 0.01-100.0 mg/kg. Wide variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

A skilled artisan could calculate the human equivalent dose (HED) of any immunogenic composition herein, based on the doses determined from animal models. For example, the effective HED of an immunogenic composition comprising recombinant IAV that encodes an HA variant may equal to about 8.1 ng to 1.62 µg HA per dose for human; preferably, equals to about 81 ng to 810 ng HA per dose. In one preferred example, the effective HED of the present recombinant IAV equals to about 468 ng HA per dose.

As for a dosing schedule, the immunogenic compositions disclosed herein may be administered to a subject at least 2 times (e.g. 2, 3, 4, 5, 6, 7, 8, 9, 10, 11, 12, 13, 14, 15 or more times) in the course of prevention or treatment for a disease. As an example, the vaccine may be administered to the subject for 2-10 times with an interval from several days to several years.

The efficacy of an immunogenic composition of this disclosure can be evaluated both in vitro and in vivo, using assays that determine the extent of an immune response (described above and in the Examples below).

Antibodies Specific to HA or NA Variants

Also provided herein are antibodies that specifically bind to any of the HA or NA variants described herein. Such antibodies may bind to an HA or NA variant as described herein with greater affinity, avidity, more readily, and/or with greater duration than it binds to the wild-type counterpart of the variant. In some examples, an antibody that "specifically binds" to an HA or NA variant may not bind to the wild-type counterpart as determined by a routine assay (i.e., binding activity undetectable).

The antibodies described herein may be prepared via a conventional method. For example, any of the HA or NA variants described herein may be administered to a suitable animal host (e.g. mouse, rabbit or sheep) to produce an antibody capable of binding to the HA or NA variant. Polyclonal antibodies, heterogeneous populations of antibody molecules, are present in the sera of the immunized subjects. Monoclonal antibodies, homogeneous populations of antibodies to a peptide variant disclosed herein can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp.

77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production.

A potential method for generating a monoclonal antibody is as follows. A subject (e.g. mouse or rabbit) may be vaccinated subcutaneously, intramuscularly and/or intranasal administrating with any of the immunogenic compositions described herein on weekly basis for 2-5 consecutive weeks. After the final immunization, splenic cells and regional lymph nodes may be removed. Blood samples may be taken regularly after immunization and subject to centrifugation to separate sera. The resultant sera may be subject to measurement of antibody titers by any suitable method (e.g. ELISA or RIA). Then, final immunization may be given to those animals showing high antibody titers to the immunogenic composition administered. Antibody-producing cells may be prepared from splenic cells and regional lymph nodes or the like of the immunized animals. In the preparation of antibody-producing cells, it may be preferable to remove tissue debris and erythrocytes as much as possible. Commercial erythrocyte remover may be used to this purpose. Alternatively, a buffer ammonium chloride and Tris may be prepared and used. The thus prepared antibody-producing cells may be immediately fused with immortal cells, such as myeloma cells to produce hybridoma cells, which semi-eternally continue to proliferate while producing antibodies. Commonly available cell strain derived from an animal, such as mouse may be used. A preferable cell strain to be used in this invention should not survive in HAT selection medium, which contains hypoxanthine, thymidine and aminopterin; and should survive there only when fused with antibody-producing cells. Examples of myeloma cells may include mouse myeloma cell lines (e.g. myeloma FO cells) and human myeloma cell lines (e.g. Karpas 707H). Cell fusion may be carried out by mixing splenic cells or lymph node cells with a commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electroporation. After the fusion, the resultant cells may then be diluted and cultured in HAT medium.

Hybridomas of interest may be selected from the fused cells. The fused cells surviving cultured in HAT medium would form colonies. The supernatant of each culture well is then collected and examine for the presence or absence of antibody titers to the immunogenic composition. As a method of confirmation, ELISA, EIA or RIA may be used. Once antibody-positive wells are identified, cells may then be cultured in a HT medium, which does not contain aminopterin. After culturing for a while, antibody titers in the culture supernatant are confirmed again. Cells that are finally selected are then subject to cloning to obtain single cells. Clones that exhibit high specificity to the present polypeptide are selected, and are proliferated to some extent to establish hybridomas.

In some examples, one hybridoma may be selected, which produces a monoclonal antibody against the HA variant of interest. The thus produced monoclonal antibody may be isolated or prepared by any known method. For example, the antibody may be prepared from cultured supernatant obtained by culturing hybridoma in a medium with low serum concentration. Alternatively, hybridoma may be injected into abdominal cavities of animals and the resultant abdominal dropsies are collected to prepare antibodies. The antibody may be purified or isolated by methods that employ affinity column, gel filtration chromatography, ion exchange chromatography or the like. Any of these known methods may be appropriately selected or used in combination.

Antibodies thus obtained may be characterized for their binding ability to the HA or NA variant versus the wild-type counterpart HA or NA antigen. Those that specifically bind the variant can be isolated.

Alternatively, antibodies specifically binding to HA or NA variants described herein may be isolated by screening an antibody library following routine practice. In some examples, an antibody library can be screened against a wild-type HA or NA antigen first to deplete antibodies capable of binding to the wild-type antigens. The resultant sub-library may be used for identifying antibodies that specifically bind the HA or NA variants.

The antibodies described herein may exhibit binding affinity and specificity to different IAV subtypes. These antibodies can be used for detecting peptide variants in immunized subjects or administered as a form of immunotherapy.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Impact of Glycosylation of Hemagglutinin (HA) on Immunogenicity

Materials and Methods
Cell Lines and Virus

Madin-Darby canine kidney cells (MDCK) and human embryonic kidney cells (HEK293T) were maintained in Dulbecco's modified Eagle's medium (DMEM) (Invitrogen, Rockville. Md.). A549 human adenocarcinoma alveolar basal epithelial cells were kept in F-12K medium (Invitrogen, Rockville, Md.) and LMH chicken hepatocellular carcinoma cells were cultured in Waymouth's MB 752/1 medium (Invitrogen, Rockville, Md.). All media were supplemented with 10% heat-inactivated fetal bovine serum (PBS) (Thermo Scientific) and antibiotics (100 U/ml penicillin G and 100 gm/ml streptomycin). The influenza A virus A/WSN/33 strain was used in the studies.

Generation of Recombinant Viruses

Eight fragments of A/WSN/33 viral genome were amplified by RT-PCR. The putative sequon N-X-S/T was used to create (from different amino acid to N) or delete (from N to A) the glycosites in the HA genome. The amino acid sequence of WT HA is SEQ ID NO: 3 as provided above.

The amino acid sequence of 285-497-556-G HA is SEQ ID NO: 1 as provided above. The amino acid sequences of 142-G HA and 142-285-497-556-G HA are provided below:

```
142-G HA (SEQ ID NO: 16, substitution at position
142 indicated in boldface):
MKAFVLVLLY AFVATDADTI CIGYHANNST DTVDTIFEKN

VAVTHSVNLL EDRHNGKLCK LKGIAPLQLG KCNITGWLLG

NPECDSLLPA RSWSYIVETP NSENGACYPG DFIDYEELRE

QLSSVSSLER FEIFPKESSW PAHTFNGVTV SCSHRGKSSF
                             142

YRNLLWLTKK GDSYPKLTNS YVNNKGKEVL VLWGVHHPSS

SDEQQSLYSN GNAYVSVASS NYNRRFTPEI AARPKVKDQH

GRMNYYWTLL EPGDTIIFEA TGNLIAPWYA FALSRGFESG

IITSNASMHE CNTKCQTPQG SINSNLPFQN IHPVTIGECP

KYVRSTKLRM VTGLRNIPSI QYRGLFGAIA GFIEGGWTGM

IDGWYGYHHQ NEQGSGYAAD QKSTQNAINR ITNKVNSVIE

KMNTQFTAVG KEFNNLEKRM ENLNKKVDDG FLDIWTYNAE

LLVLLENERT LDFHDLNVKN LYEKVKSQLK NNAKEIGNGC

FEFYHKCDNE CMESVRNGTY DYPKYSEESK LNREKIDGVK

LESMGVYQIL AIYSTVASSL VLLVSLGAIS FWMCSNGSLQ

CRICI

142-G HA (SEQ ID NO: 17, substitution at positions
142, 285, 497 and 556 indicated in boldface):
MKAFVLVLLY AFVATDADTI CIGYHANNST DTVDTIFEKN

VAVTHSVNLL EDRHNGKLCK LKGIAPLQLG KCNITGWLLG

NPECDSLLPA RSWSYIVETP NSENGACYPG DFIDYEELRE

QLSSVSSLER FEIFPKESSW PAHTFNGVTV SCSHRGKSSF
                             142

YRNLLWLTKK GDSYPKLTNS YVNNKGKEVL VLWGVHHPSS

SDEQQSLYSN GNAYVSVASS NYNRRFTPEI AARPKVKDQH

GRMNYYWTLL EPGDTIIFEA TGNLIAPWYA FALSRGFESG
                                        285

IITSAASMHE CNTKCQTPQG SINSNLPFQN IHPVTIGECP

KYVRSTKLRM VTGLRNIPSI QYRGLFGAIA GFIEGGWTGM

IDGWYGYHHQ NEQGSGYAAD QKSTQNAINR ITNKVNSVIE

KMNTQFTAVG KEFNNLEKRM ENLNKKVDDG FLDIWTYNAE

LLVLLENERT LDFHDLNVKN LYEKVKSQLK NNAKEIGNGC

FEFYHKCDNE CMESVRAGTY DYPKYSEESK LNREKIDGVK
                  497

LESMGVYQIL AIYSTVASSL VLLVSLGAIS FWMCSAGSLQ
                                        556

CRICI
```

Viral cDNAs were inserted into pcDNA3.1 containing the pol I and CMV promoter similar to the generation of pHW2000. Recombinant viruses were generated by the 8-plasmid co-transfection method into MDCK/293T cells according to routine methods. Supernatants were collected, titrated, and frozen at −80° C. until use.

Antibodies

Mouse monoclonal anti-HA antibody was obtained from Sino Biological. Mouse monoclonal anti-actin antibody was purchased from Millipore. Goat polyclonal anti-M1 and mouse monoclonal anti-6×His antibodies were purchased from Santa Cruz Biotechnology. Rat monoclonal anti-INF gamma antibody was obtained from ABcam. Rabbit polyclonal anti-granzyme B antibody was purchased from Aviva Systems Biology. All commercial antibodies were validated for specificity by companies and us via Western blot.

Virus Replication Rate

Monolayer cultures of MDCK, A549, and LMH cells in 12-well dishes were washed twice with 1× phosphate-buffered saline (PBS). The cells were infected with variants of modified influenza virus at an MOI of 0.01, 0.1 and 1 respectively in serum-free medium containing 0.1 (0.01 for LMH) g/ml L-(tosylamido-2-phenylethyl) chloromethyl ketone (TPCK)-trypsin (Pierce) and incubated at 37° C. for 1 h; cells were washed twice with 1×PBS and then incubated with the complete medium. At the time points shown in the figure, the supernatants were collected to determine the virus titer by performing plaque assay in MDCK cells.

Plaque Assay

Monolayers of MDCK cells in 6-well dishes were washed twice with 1×PBS. The cells were then inoculated with serial 10-fold dilutions of the virus in serum-free medium containing 0.5 µg/ml TPCK-trypsin and incubated at 37° C. for 1 h. Afterward, the cells were washed and overlaid with MEM containing 0.5% agarose (Lonza) and 0.5 gm/ml TPCK-trypsin. After 3 days, the cells were fixed with 10% formaldehyde and stained with 0.1% crystal violet solution.

Protein Expression and Purification

The plasmid encoding secretory HA was transfected into the HEK293T cell lines using polyethyleneimine and was cultured in Freestyle 293 expression medium (Invitrogen) supplemented with 0.5% bovine calf serum. The supernatant was collected 72 h after transfection and cleared by centrifugation. HA proteins were purified with nickel-chelation chromatography as previously described. The purified proteins were concentrated by a Millipore Amicon Ultra Filter and loaded onto a Superdex-200 gel filtration column (GE) pre-equilibrated in PBS buffer, and different fractions were collected.

Glycan Array

Glycan microarrays were prepared by printing (AD3200, BioDot) the glycans with a pentyl amine tail prepared in the labs to the NHS-activated glass slide (Nexterion H) by robotic pin (SMP2B, TeleChem International) at 25° C. with 60% humidity. Nexterion H slides were spotted with solutions of glycan 1-29 and 30-39 at 100 µM from bottom to top with 3 replicates horizontally in each grid and dried under vacuum. The resulting images were analyzed with GenePix Pro 6.0 (Molecular Devices) to locate and quantify the fluorescence intensity of all of the spots on the grid.

Virus Binding Assay

The same amount of viruses was inactivated in a buffer containing the neuraminidase inhibitor Oseltamivir carboxylate (10 µM). Suspensions of the inactivated viruses with Oseltamivir carboxylate were overlaid onto the arrays and incubated at room temperature for 30 min. Slides were subsequently washed by successive rinses in PBS-0.05% Tween, PBS, and deionized water three times. Bound viruses were detected using the anti-H1 antibody. The slides were gently rocked at room temperature for 60 min. After repeating the washing steps, binding was detected by overlay with labeled secondary antibodies.

Infectivity Assay

A PEG virus precipitation kit (BioVision) was used to concentrate viruses following the manufacturer's protocol, and determined the amount of virus by using Western blot. The same amounts of variant viruses were used to infect A549 cells in F-12K serum-free medium containing 0.5 μg/ml TPCK-trypsin and incubated at 37° C. for 30 min. Then, the cells were washed twice and overlaid with F-12K medium containing 10% heat-inactivated fetal bovine serum (FBS) (Thermo Scientific) and antibiotics (100 U/ml penicillin G and 100 gm/ml streptomycin). After 10 hpi, the total cell lysate was collected and analyzed. MDCK cells were infected with variant viruses infected in serum-free medium containing 0.5 gm/ml TPCK-trypsin and incubated at 37° C. for 30 min. Then, the plaque assay procedure was followed.

Hemagglutination Assay

The same amounts of IAV and HA proteins were serially diluted 2-fold in a total volume of 100 μl. Next, 25 ul of a 2% (vol/vol) turkey erythrocyte solution were added. The virus and erythrocytes were gently mixed and the hemagglutination was read after incubation for 60 min at room temperature.

Hemagglutination Inhibition Assay

After serum samples were serially diluted two-fold in a 96-well plate, 4 hemagglutination units (HAU) of WT WSN were added to each well for 1 h at room temperature. After incubation, 25 μl of a 2% (vol/vol) turkey erythrocyte solution were added to give a total volume of 125 μl and incubated for 1 h at room temperature. The HAI titer of the individual serum sample was determined to be the inverse of last dilution where cells were not agglutinated.

Cell Binding Assay

Turkey erythrocytes were pretreated with different amounts (0-60 μg/mL) of *Vibrio cholerae* neuraminidase (receptor destroying enzyme, RDE) (Sigma) for 60 min at 37° C. Then, the erythrocytes were washed once with PBS and made into 2% (vol/vol) erythrocyte solutions using PBS. Twenty-five microliters of each 2% solution were added to the same amount of IAV and HA proteins to have a total volume of 125 μl. IAV and RDE-treated erythrocytes were incubated for 1 h at room temperature and then agglutination was measured. Data were expressed as the maximal concentration of RDE that still gave full agglutination.

Deglycosylation

An aliquot of viruses or proteins was deglycosylated in a buffer solution purchased from Sigma-Aldrich. After ultracentrifugation, 200 μl infection medium containing virus (1×107 pfu) or purified proteins were mixed with protease inhibitor (Roche), 1 μg endoglycosidase F1, 1 μg endoglycosidase F2, 1 μg endoglycosidase F3, and 1 μg endoglycosidase H or 1 μg PNGase F at 37° C. for 24 h in the dark. The endoglycosidase cocktail (endo F1, F2, F3 and H) or PNGase F can trim all of the glycan structure down to a single GlcNAc residue to produce mono-glycosylated samples or non-glycosylated samples, individually. After deglycosylation, samples were checked by Western blot.

IAV Preparation for Immunogenicity Test

WT, 285-497-556-G and 142-285-497-556-G HA viruses were cultured in MDCK cells. These viruses were inactivated by using 0.1% BPL (Acros Organics, Geel, Belgium) at room temperature for 24 h followed by dialysis for 24 h against FINE buffer (5 mM HEPES, 150 mM NaCl, 0.1 mM EDTA, pH 7.4) and tested by performing serial passages on MDCK cells. Female C57Bl/6 mice, aged 6-8 weeks, were immunized intramuscularly with an equal amount of 6 μg HA per inactivated virus dose, and immunized twice subcutaneously on days 0 and 21. One week after the booster immunization, mice were divided into two groups and every group contained 10 mice. One group was anesthetized and inoculated intranasally with 10×LD50 of WSN/33 or H5N1 virus, and the serum sample of the other group was collected for analysis of the antiserum production. The mice were monitored daily for survival in a period of 14 days after challenge. All animal experiments were evaluated and approved by the Institutional Animal Care and Use Committee of Academia Sinica.

Virulence Assay

Figure 3:
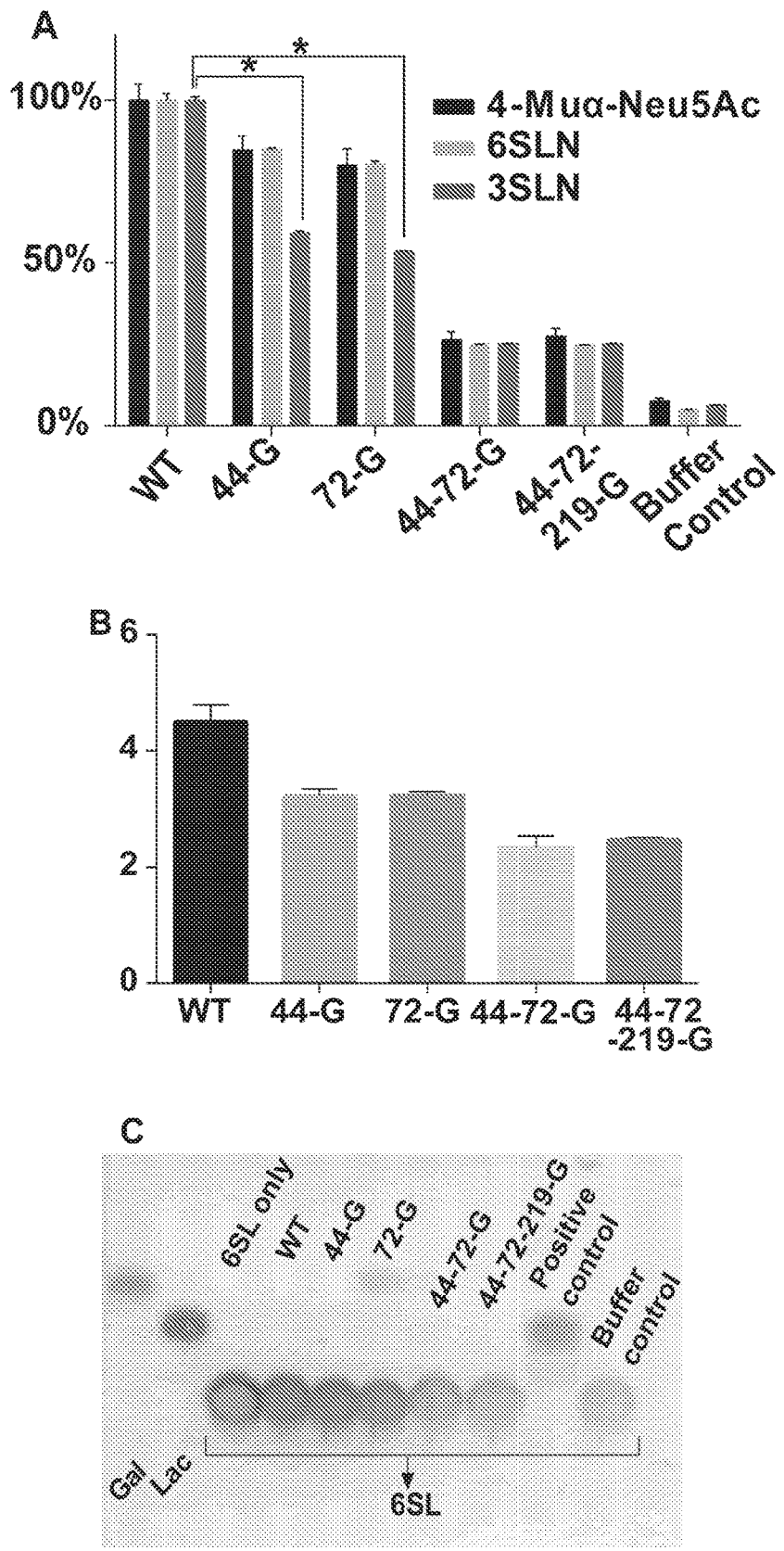
FIG. 3 includes diagrams showing the impact of glycosylation on immunogenicity of neuraminidase (NA) on IAV. (A): a chart showing measurements of NA activity using different glycoconjugates, 4-Muα-Neu5Ac, 6-SLN and 3-SLN; the NA activity was relative to each WT substrate designated as 100%. (B): a chart showing the comparison of virus production in LMH cells. The virus titers were determined at 48 hpi. (C): a photo showing thin layer chromatography of variants of viruses that interact with 6-SL. (D): a chart showing NA activity of 44-72-G virus, deglycosylated 44-72-G virus and 44-72-219-G virus at 37° C. and 55° C., using a 4-MUNANA assay. (E): a photo showing viral morphology, using transmission electron microscopy for WT virus. (F): a photo showing viral morphology as in panel E but for 44-72-219-G virus. (G): a diagram showing the survival rate of mice challenged with WT IAV (WSN) or with IAV containing indicated NA variant. (H): a chart showing the body of mice treated as in panel G. In panels A, B and D, Mean±SEM for 3 independent experiments is shown; in panel G, 5 independent experiments is shown; in panel H, Mean±SEM. for 5 independent experiments is shown. *: $P<0.001$. **: $P<0.05$.
Figure 3:
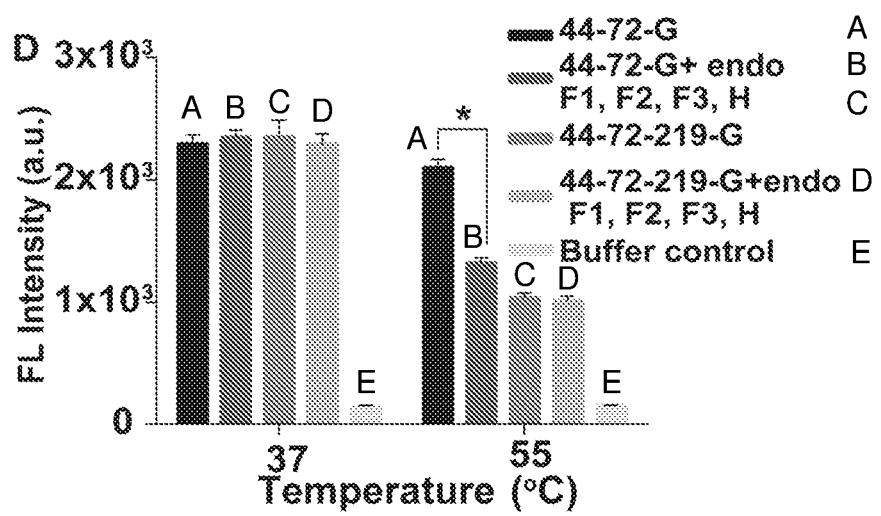
Figure 3:
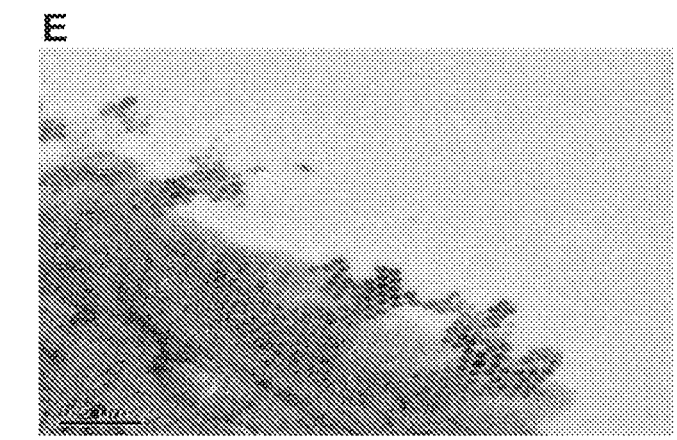
Figure 3:
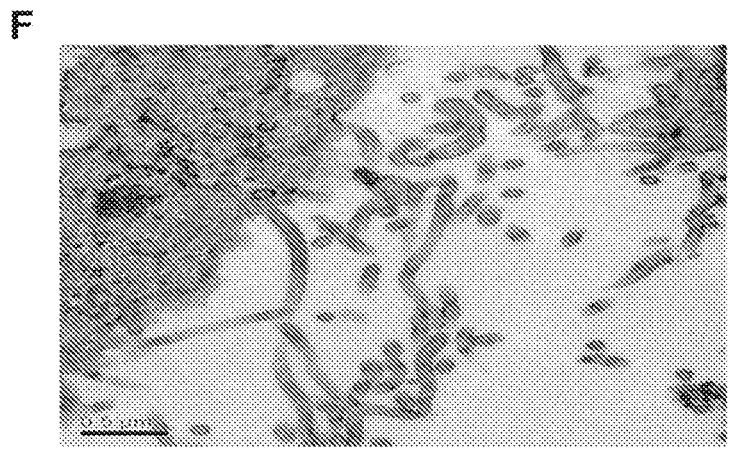
Figure 3:
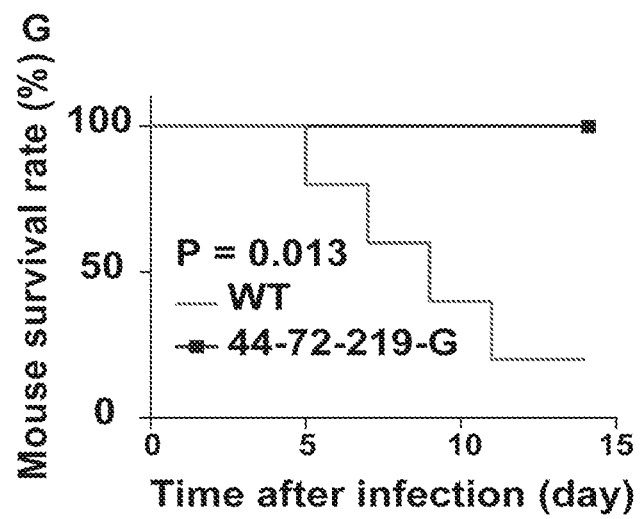
Figure 3:
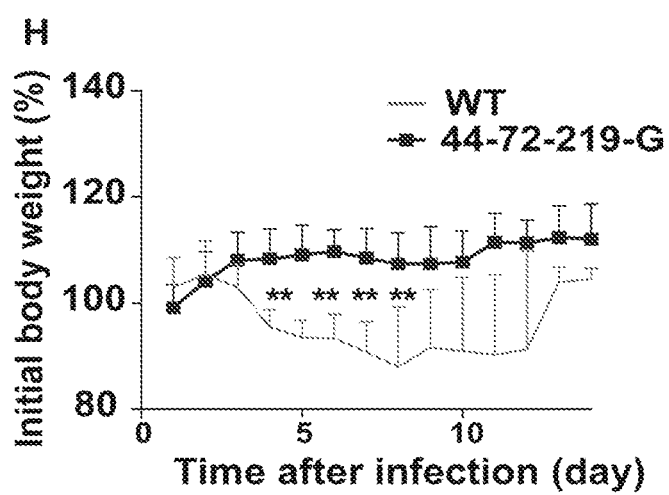

The virulence of recombinant viruses was measured using groups of five female 4-6-week-old BALB/c mice that were intranasally inoculated with 50 μl of virus ($5 \times 10^5$ PFU for WSN and LAIV 44-72-219-G virus in FIG. 3: panel G). Survival and body weight changes were recorded daily for 14 days after infection.

Results

Impact of N142-Glycosylation on HA Structure and Activity

Figure 5:
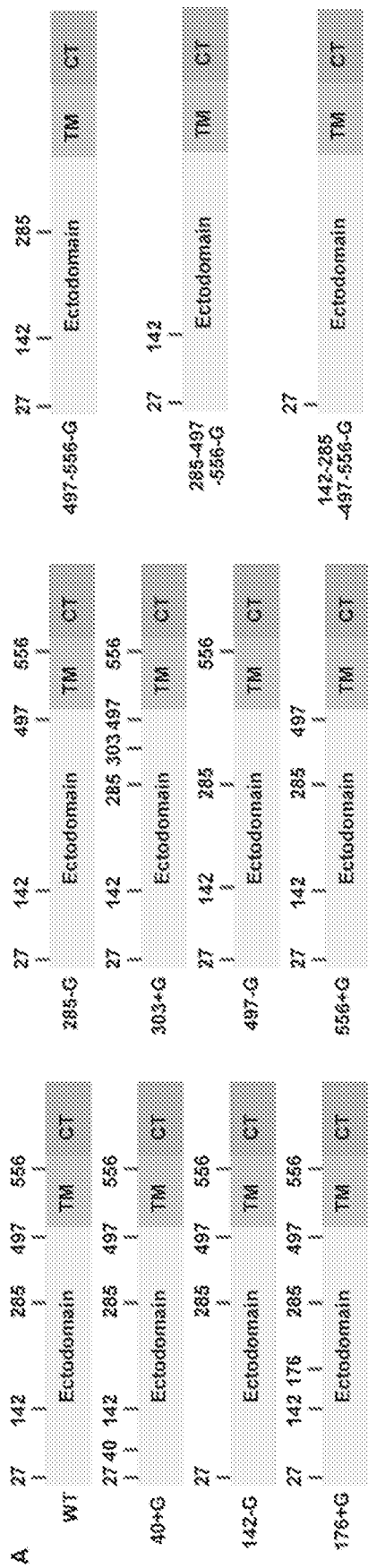
FIG. 5 includes diagrams showing the impact of HA deglycosylation on the immunogenicity of HA on IAV. (A): a schematic overview of 11 IAVs with different glycosites on HA; CT indicates C-terminal cytoplasmic domain; TM indicates transmembrane domain. All recombinant viruses were confirmed by genome sequencing. (B): a diagram showing the comparison of virus production in A549 cells infected with 11 variants of virus at 48 hpi. (C): a chart showing the circular dichroism spectra of HA variants as indicated. (D): a photo showing western blot analysis of the same concentration of four variants of IAV as indicated, using anti-HA and anti-M1 antibodies. The filter was probed with anti-HA and anti-M1 monoclonal antibodies. (E): a diagram showing the infectivity of viruses with the indicated HA variants, using a plaque assay to determine viral titer post infection of MDCK cells. (F): a diagram showing cell receptor binding avidities, using a cell-binding assay. (G): a diagram showing the comparison of virus production (as determined by viral titer) of the indicated viruses in LMH cells infected at 48hpi. (H): a photo showing western blot analysis of 3 variants of IAV after deglycosylation by an endoglycosidase cocktail, using anti-HA antibody. (I): a diagram showing mouse survival rate after mice were challenged with a lethal dose of indicated viruses that had been treated with an endoglycosidase cocktail. In panels B, E, F and G, Mean±SEM of 3 independent experiments is shown; in panel I, 10 independent experiments are shown. *: $P<0.001$.
Figure 5:
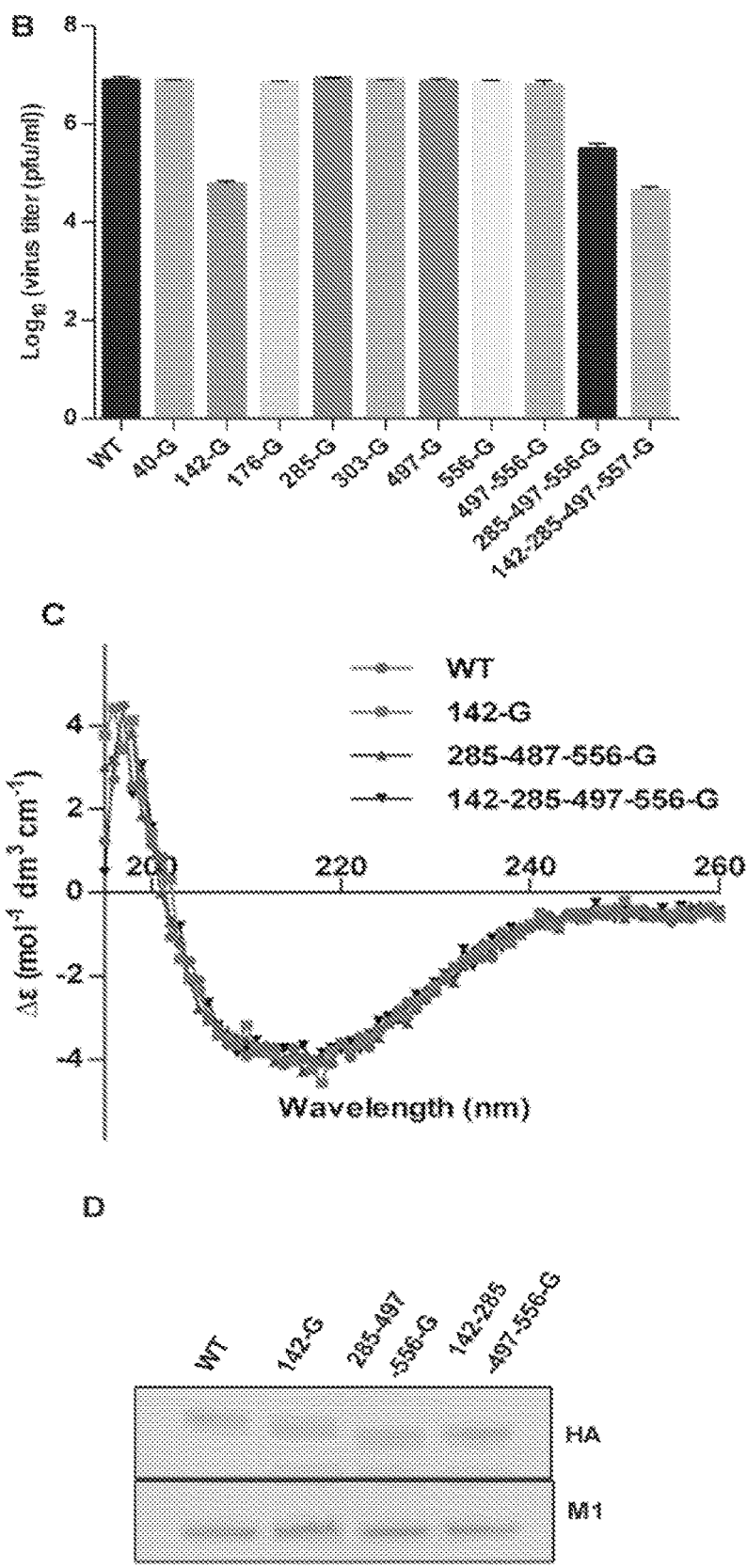
Figure 5:
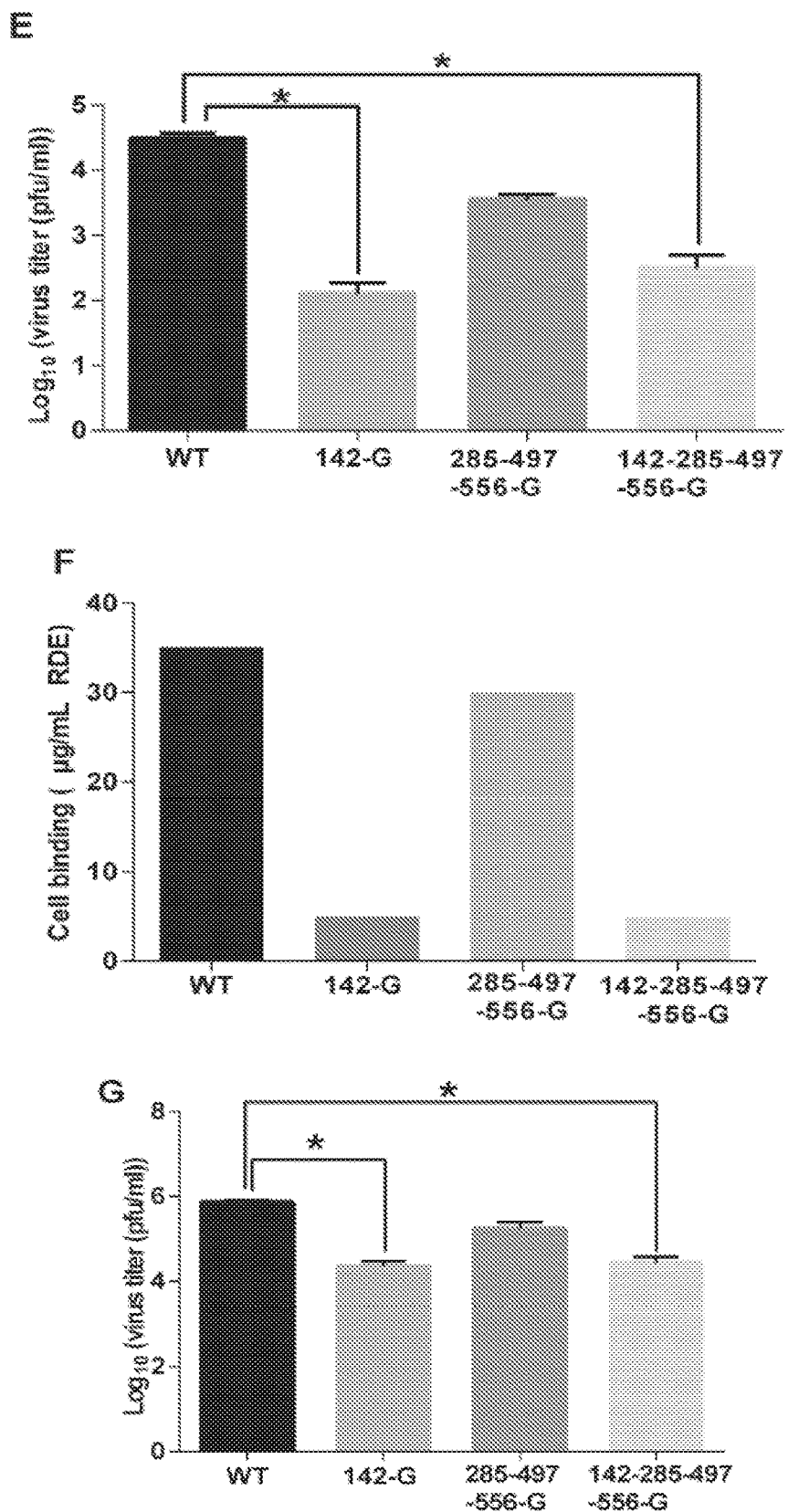

Since several glycosylation sites (glycosites 27, 40, 176, 303, and 497) on HA are highly conserved among the H1, H3 and H5 subtypes, wild-type H1N1 A/WSN/33 (WSN) was used as a model to create or delete specific glycosites to address the effect of glycosylation by using reverse genetics (FIG. 1, panel A and FIG. 5: panel A). The virus did not survive glycosite-27 deletion (i.e., N27A mutation designated as 27-G). Similarly, the highly conserved and potential glycosite at position 40, 176 or 303 was mutated (designated as 40+G, 176+G, and 303+G) to determine the effect on replication. The results showed that the replication rates of variants with mutation at the highly conserved or potential glycosite (40+G, 176+G, 303+G, or 497-G) and WT were similar, but the replication rate of glycosite-142-deleted virus (142-G and 142-285-497-556-G virus) was two orders of magnitude lower than that of the WT virus in both MDCK and A549 cells, suggesting that glycosite 142 plays an important role in IAV replication (FIG. 1, panel B and FIG. 5: panel B). In a circular dichroism study, the glycans at glycosite 142 did not affect the secondary structure of HA (FIG. 5, panel C), and the ratios of HA to M1 among the glycosite-142 deleted variants were similar, suggesting that glycosite 142 is not essential for virus assembly and/or maturation (FIG. 5, panel D).

Figure 6:
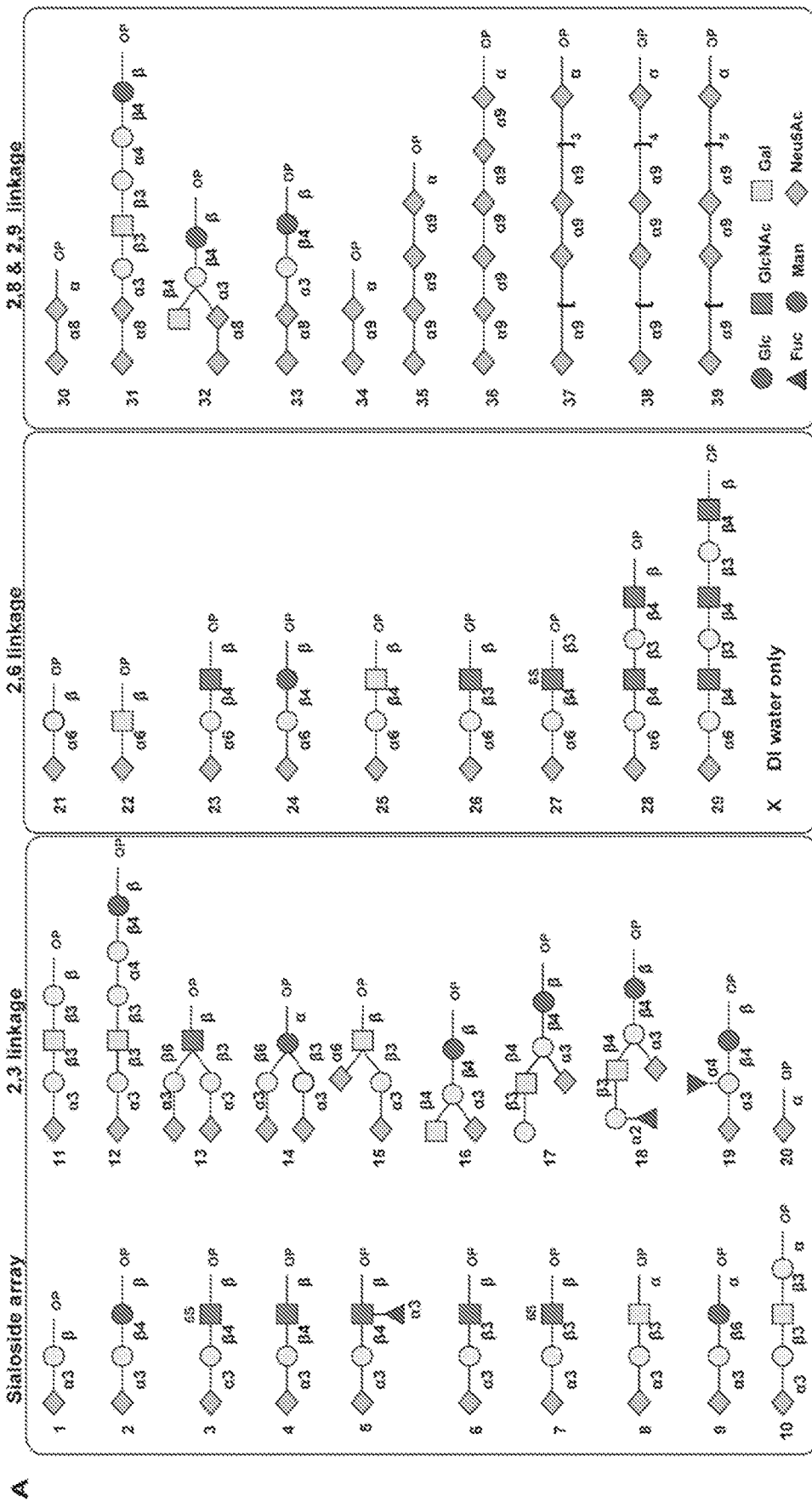
FIG. 6 includes diagrams showing the impact of glycosylation on binding specificity and binding avidity of HA. (A): a schematic overview of sialoside structures on the glycan array for IAV binding studies. This synthetic SA glycan array consisted of the following sialosides: 20 α2,3-glycans (1-20), 9 α2,6-glycans (21-29), and 10 α2,8 and α2,9 glycans (30-39), designed to study IAV binding. (B): a diagram showing glycan array analysis of 4 variants of virus as indicated. (C): a diagram showing glycan array analysis of 4 HA protein variants. (D) a diagram showing glycan array analysis of deglycosylated 285-497-556-G HA IAV. (E): a diagram showing glycan array analysis of 142-285-497-556-G HA IAV. In panels B, C, D and E, Mean±SEM of 3 independent experiments is shown.
Figure 6:
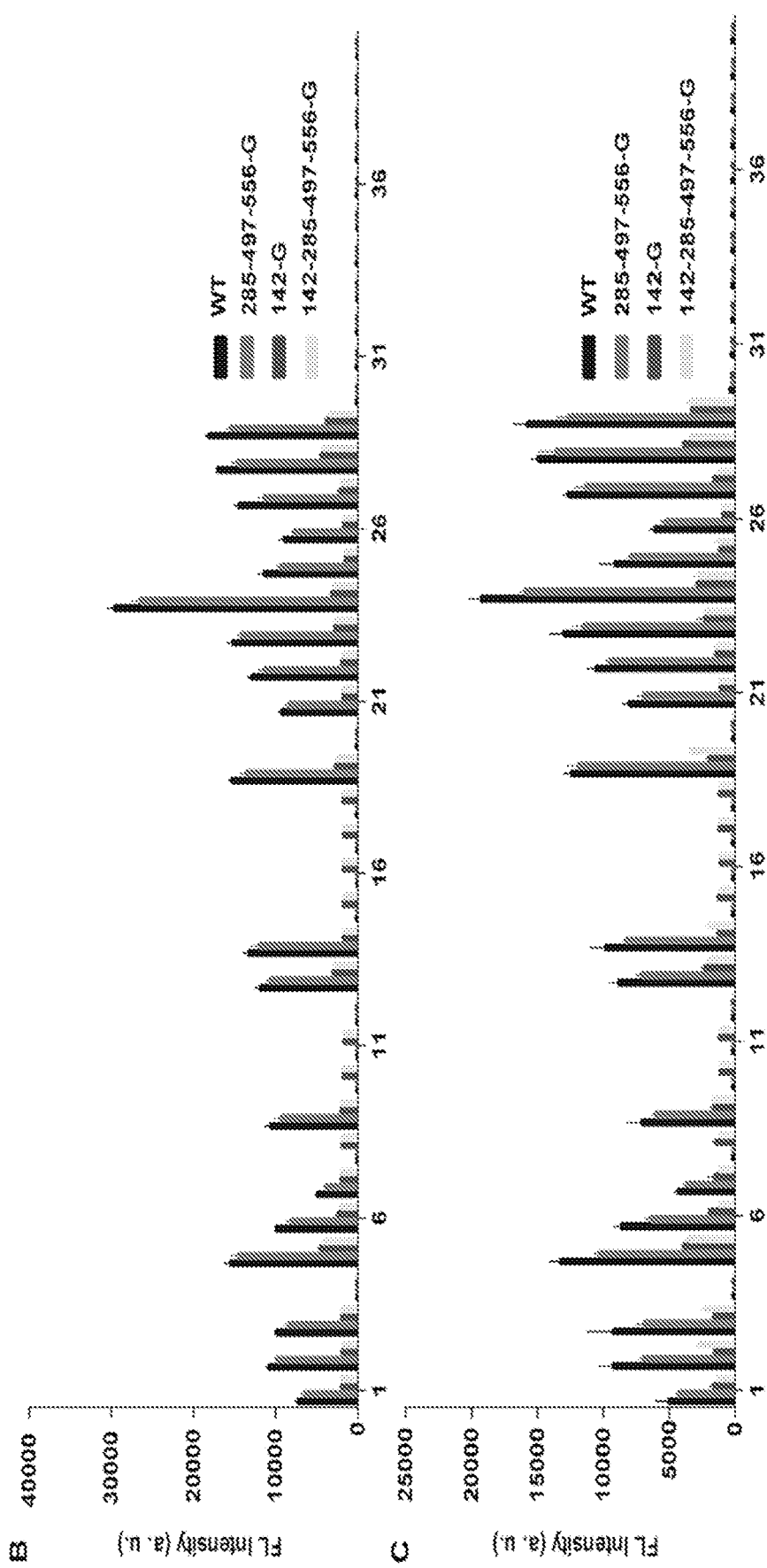
Figure 6:
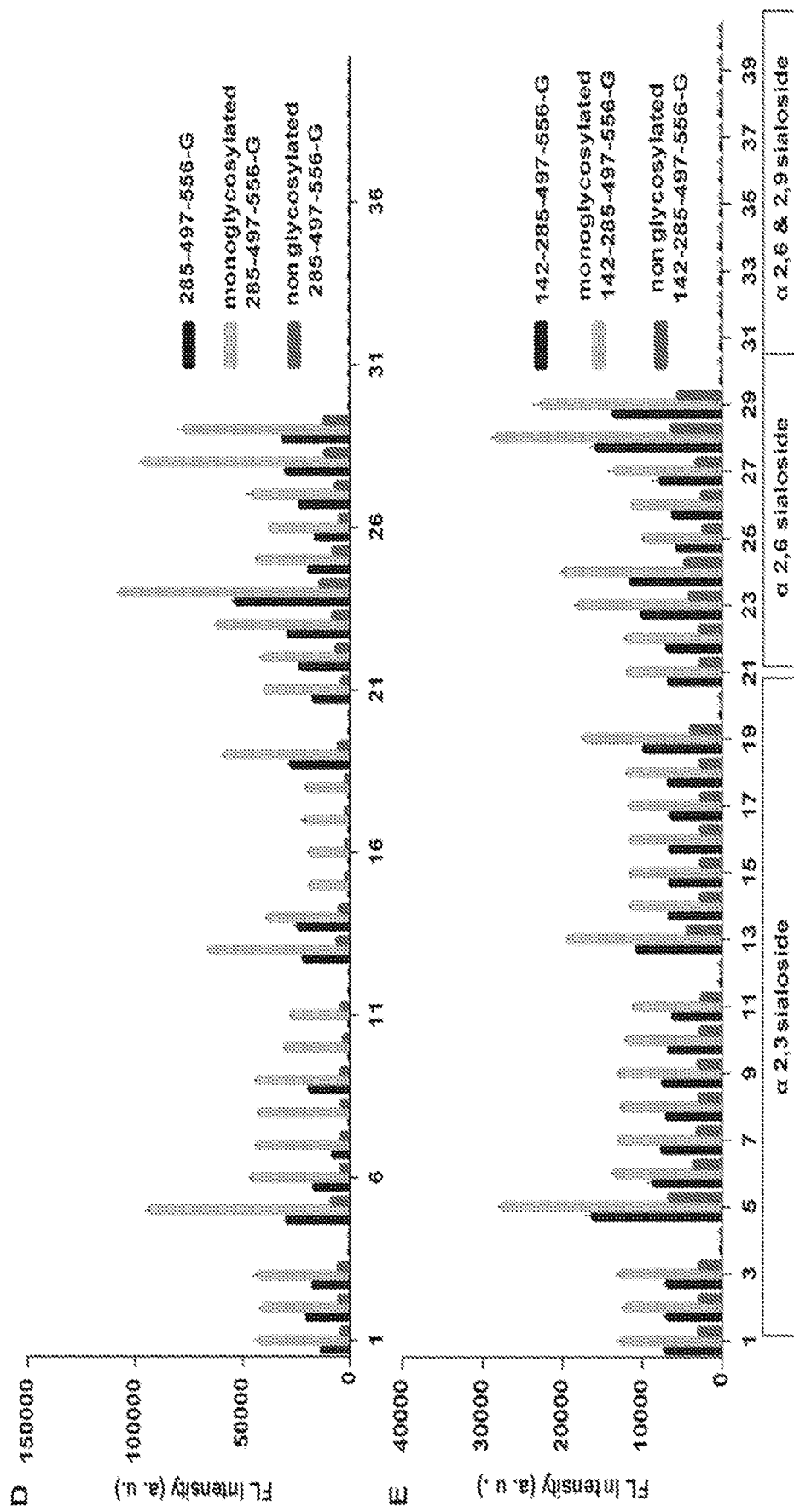

Glycosite 142 is required for virus entry, because, in the virus infectivity assay, very weak signals of HA and M1 were detected in the A549 cells infected with glycosite-142-deleted virus (142-G or 142-285-497-556-G virus) (FIG. 1, panel C and FIG. 5, panel E). 142-G and 142-285-497-556-G are SEQ ID NOs: 16 and 17, respectively, as provided above. The glycan array analysis showed that the glycosite-142-deleted virus interacted with more sialosides than the WT virus (glycans 8, 10, 11, and 15-18) and the same results were also observed from the corresponding HA protein, suggesting that glycosylation at glycosite 142 affects the receptor binding specificity of HA (FIG. 1: panel D, and FIG. 6, panels A-C). In addition, glycosite 142 modulates the binding avidity of HA, because the glycosite-142-deleted virus showed lower fluorescence intensity in glycan array analysis, and had lower capability in hemagglutination and cell binding (FIG. 1, panels D-E and FIG. 5, panel F). Although the glycosite-142-deleted virus can interact with more α2,3-sialosides in the glycan array analysis, it is not involved in the human and/or avian adoption of WSN HA, as the replication rate of 142-G or 142-285-497-556-G virus in LMH cell lines (from chicken hepatocellular carcinoma) was still two orders of magnitude lower than that of WT (FIG. 5, panel G).

The molecular mechanism of avidity and specificity affected by the glycosylation at glycosite 142 was further studied and it was found that both avidity and specificity were modulated by the glycan composition. Treatment with a cocktail of endoglycosidases (Endo-F1, F2, F3 and H), changed the interaction profile of the WT and 285-497-556-G viruses on the glycan array and the interaction patterns were similar to that of the 142-G and the 142-285-497-556-G viruses. HA 285-497-556-G is provided above as SEQ ID NO: 1. Surprisingly, after treatment with the endoglycosidase cocktail, the fluorescence intensity of the monoglycosylated virus on the glycan array was increased, but decreased in all types of non-glycosylated variants (PNGase F treatment) (FIG. 1, panel F, FIG. 5, panel H and FIG. 6, panels D-E).

Mice were challenged with H5N1 to determine whether glycosite 142 is involved in the host immune response The mice immunized with the inactivated 142-285-497-556-G virus survived for a shorter period of time and induced less HA antiserum compared to the mice immunized with inactivated WT virus, and the inactivated 285-497-556-G virus-immunized mice induced the same amount of HA antiserum but survived longer, and survived well in all cases after WSN challenge in the immunogenicity test (FIG. 1, panels G-H and FIG. 5, panel I). This study suggested that glycosylation at glycosite 142 is important for the immunogenicity of IAV.

In the seasonal H1N1 strains, glycosite 142 in HA is believed to play a significant role in evading the human immune response and human H3N2 IAV also gains the glycosite in this region (glycosite 144 in H3 numbering) during evolution through positive selection. Surprisingly, after IAV acquired glycosite 142 in HA, results of this example suggests that the efficiency of virus infectivity is promoted by the regulation of the HA-SA interaction, and the host immune response was altered. Therefore, glycosite 142 may be an important factor that should be considered in the development of vaccines against human IAV.

Example 2: Impact of Glycosylation of Neuraminidase (NA) on Immunogenicity

Materials and Methods
Generation of Recombinant Viruses

Same method as described in Example 1 except site-directed mutagenesis was used to add a stop codon in the NA genome to remove the stalk and catalytic domain of NA. For the preparation of virus without NA stalk and catalytic domains (LAIV WSN-NA, SEQ ID NO: 2), MDCK/293T cell lines stably expressing NA were generated to rescue, maintain and analyze the virus. Briefly, full-length NA (from WSN strain, SEQ ID NO: 4) was cloned into a cDNA expression lentivector (pLAS2w.Ppuro). Then, NA-expression lentivirus was generated using the protocol provided by the National RNAi Core Facility, Academia Sinica, Taiwan (http://rnai.genmed.sinica.edu.tw). HEK293T and MDCK cells were infected with NA-expression lentivirus with triple multiplicity of infection in the presence of Polybrene (Sigma) at a final concentration of 8 μg/ml. Cells were incubated with virus for 24 h prior to replacing the medium with selective medium containing puromycin (3 μg/ml) (Invitrogen). After 3-day incubation, total cell lysate was collected to check the expression efficiency of NA by Western blot analysis.

NA Activity

The enzymatic activity of NA was measured by standardizing the virus samples with pfu and the protein samples as described. Aliquots of virus were prepared at a titer of 1×106 pfu and then incubated at 37° C. with 4-MUNANA (Sigma). After 30 min, the reaction was stopped with 0.14 M NaOH and 83% ethanol, and the NA activity was measured with excitation at 360 nm and emission at 450 nm. The final concentration of the substrate ranged from 0 to 1500 mM. Fluorescence was monitored every 5 min for 60 min (12 measures) (4-MUNANA assay). Km (substrate concentration that yield half-maximal velocity) and Vmax (maximum velocity) of NA were calculated with Prism software (GraphPad) by fitting the data to the Michaelis-Menten equation using nonlinear regression. For measuring the kinetics of enzymatic cleavage of different glycoconjugates (4-Muα-Neu5Ac, 3-SLN, 6-SLN, 3-SL and 6-SL from Sigma), the N-acetylneuraminic acid released from the glycoconjugates was determined by reaction with N-acetylmannosamine (ManNAc) dehydrogenase and sialic acid aldolase. ManNAc, the aldolase-cleaved product of N-acetylneuraminic acid, was interacted with ManNAc dehydrogenase and NAD+ to form the NADH byproduct, and the fluorescence intensity of NADH at 340/450 nm was measured. In the reactions, 2 μg sialic acid aldolase (*Pasteurella multocida*, recombinant), 3 μg ManNAc dehydrogenase (*Flavobacterium* sp. 141-8, recombinant), 50 mM MES buffer, pH 6.5, 0.2 mM NAD+, and an appropriate amount of NA were mixed, and the final concentration of the glycoconjugate was adjusted to a range from 0 to 1500 mM. Fluorescence was monitored every 5 min for 30 min (6 measures).

Mice Treated with LAIV WSN-44-72-219-G and LAIV WSN-NA

LAIV WSN-NA virus was cultured in MDCK cells with NA expression. 25 μl of LAIV WSN-44-72-219-G or LAIV WSN-NA (nonlethal dose for WT WSN) were introduced into each nostril on days 0 and 21 while the mouse was conscious and the virus did not reach the lower respiratory tract. NA 44-72-219 is listed as SEQ ID NO: 11 above. Then the immunogenicity test procedure was followed.

Antibodies

Anti-NA antibodies were obtained from Sino Biological.
Protein Expression and Purification NA was produced by the method described in Example 1 above.

IAV Preparation for Immunogenicity Test

LAIV WSN-NA virus was produced in MDCK cells expressing NA, using the same method described in Example 1 above.

Transmission Electron Microscopy

MDCK cells were grown on ACLAR embedding film with 7.8-mil thickness (E,M,S) for 1 day followed by infection with influenza virus at an MOI of 5. At 18 hpi, virus-infected cells were rinsed with 0.1M cacodylate buffer and fixed with 2.5% glutaraldehyde in 0.1 M cacodylate buffer at 4° C. for 30 min. Then cells were postfixed with 1% osmium tetroxide in 0.1 M cacodylate for 30 min, stained with 1% uranyl acetate and lead citrate for 1 h, dehydrated by using ethanol, and embedded with resin. After baking, the sample was cut into 80-nanometer thin sections using ultramicrotome. Finally, samples were examined with Tecnai G2 Spirit TWIN (FEI Company).

Virulence Assay

Mice were intranasally inoculated with 50 μl of virus (1×10$^6$ PFU for WSN and LAIV WSN-NA shown in FIG. 12, panel E), following the descriptions provided in Example 1 above.

Neuraminidase Inhibition Assay

Neuraminidase inhibition assay was used to analyze the production of NA antibody. Here, a NA-Fluor™ Influenza Neuraminidase Assay Kit (Life Technologies) was used to perform this experiment. Briefly, the virus was incubated with the reaction buffer from the kit, then mixed and heat inactivated, followed by serial dilutions to different concentrations as indicated in the figure, and the fluorescence was monitored. Neuraminidase inhibition titers were calculated as the reciprocal of the highest dilution with at least 50% inhibition.

IAV-Specific CD8+ T Cell Analysis

The PBMC obtained from PBS, WSN or LAIV WSN-NA treated mice was incubated with live or inactivated WSN (UV treatment) at an MOI of 3 in RPMI 1640 medium containing 0.5 µg/ml TPCK-trypsin and incubated at 37° C. for 1 h. Then, the cells were washed twice and overlaid with RPMI 1640 medium containing 10% heat-inactivated FBS and antibiotics. After incubation for 24 h, CD8+ T cells were isolated by Dynabeads Untouched Mouse CD8 Cells kit (Invitrogen) following the procedure from the company, and analyzed by flow cytometry and Western blot. For viral protein M1 and NP stimulation, the GM-CSF-cultured bone marrow-derived dendritic cells (BMDC) were incubated with or without 100 µM viral M1 and NP epitopes in complete RPMI 1640 medium for 24 h at 37° C., then mixed with PBMCs from immunized mice at the ratio 1:1. After incubation for 48 h, CD8+ T cells were isolated and analyzed by flow cytometry and Western blot. The M1 epitopes were GILGFVFTL (SEQ ID NO: 18), RLEDVFAGK (SEQ ID NO: 19) and ASCMGLIY (SEQ ID NO: 20), and NP epitopes were CTELKLSDY (SEQ ID NO: 21), SRYWAIRTR (SEQ ID NO: 22) and LELRSRYWA (SEQ ID NO: 23) (Mission Biotech). Peptides were dissolved in dimethyl sulfoxide at 5.0 mg/ml, diluted in RPMI 1640 to 100 µM, and stored at 20° C.

Flow Cytometry

Cells were harvested and suspended in FACS buffer (2% FBS in PBS) at a density of 106/mL. The antibody used in this study was anti-INF gamma antibody. Cellular fluorescence intensity was analyzed by FACSCanto (BD Biosciences) and FCS Express 3.0 software.

Results

Glycosylation at N-44, N-72 and N-219 Affected the Secondary Structures of NA

Figure 2:
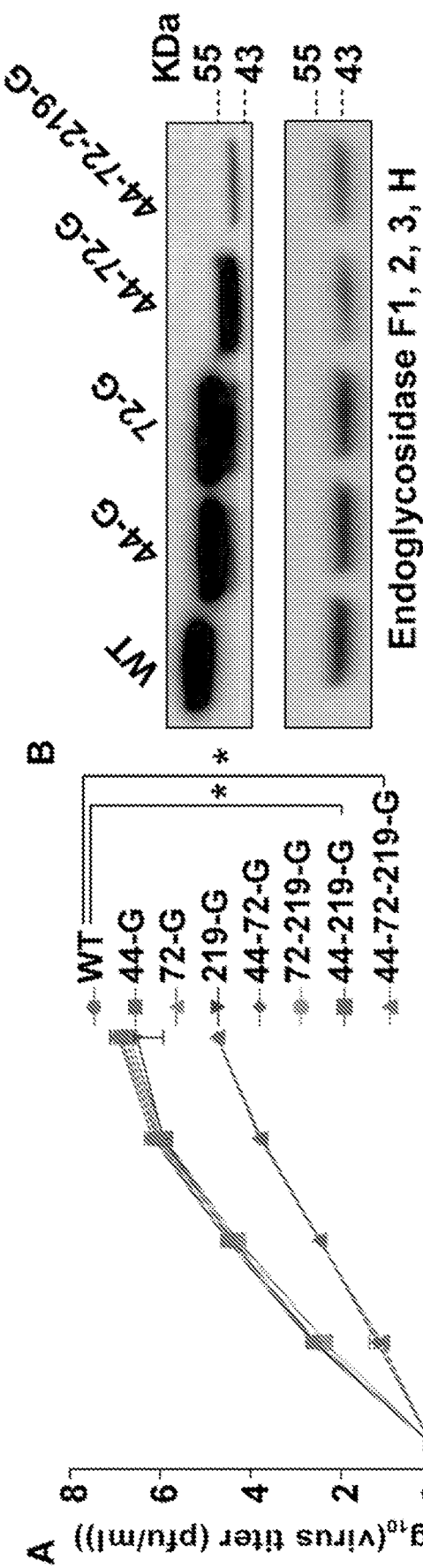
FIG. 2 includes diagrams showing the impact of glycosylation on virulence and structure of neuraminidase (NA) on IAV. (A): a chart showing the comparison of virus replication rates in A549 cells. (B): a photo showing western blot analysis of the molecular weights of glycosylated and deglycosylated NA variants as indicated, using anti-NA antibody. (C): a chart showing circular dichroism spectra of different types of NA as indicated. (D): a chart showing circular dichroism spectra of deglycosylated variants of NA. (E): a chart showing NA activity of IAV measured using a 4-MUNANA assay. In panel B, Mean±SEM for 3 independent experiments is shown; in panel E, Mean±SEM for 5 independent experiments is shown. *: $P<0.001$.
Figure 2:
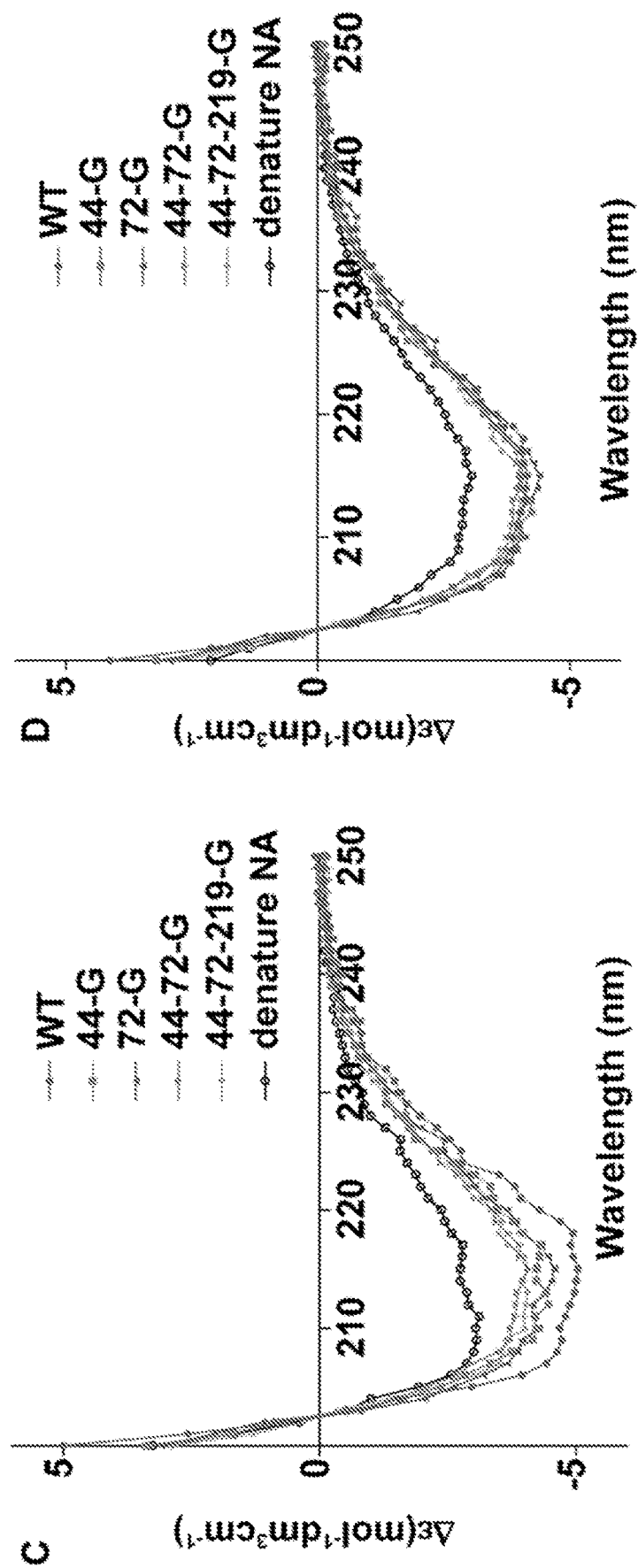
Figure 2:
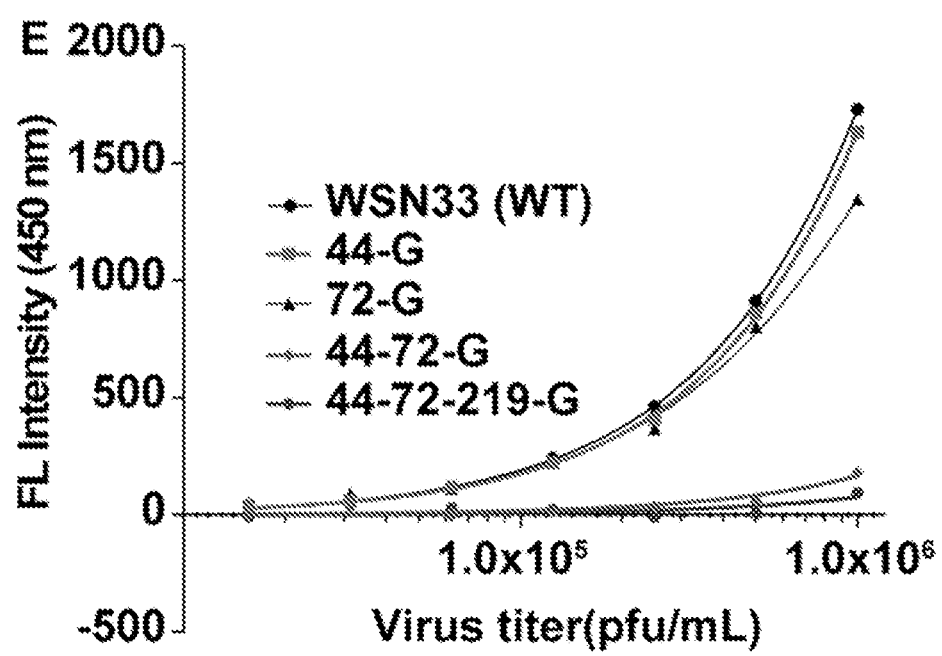
Figure 7:
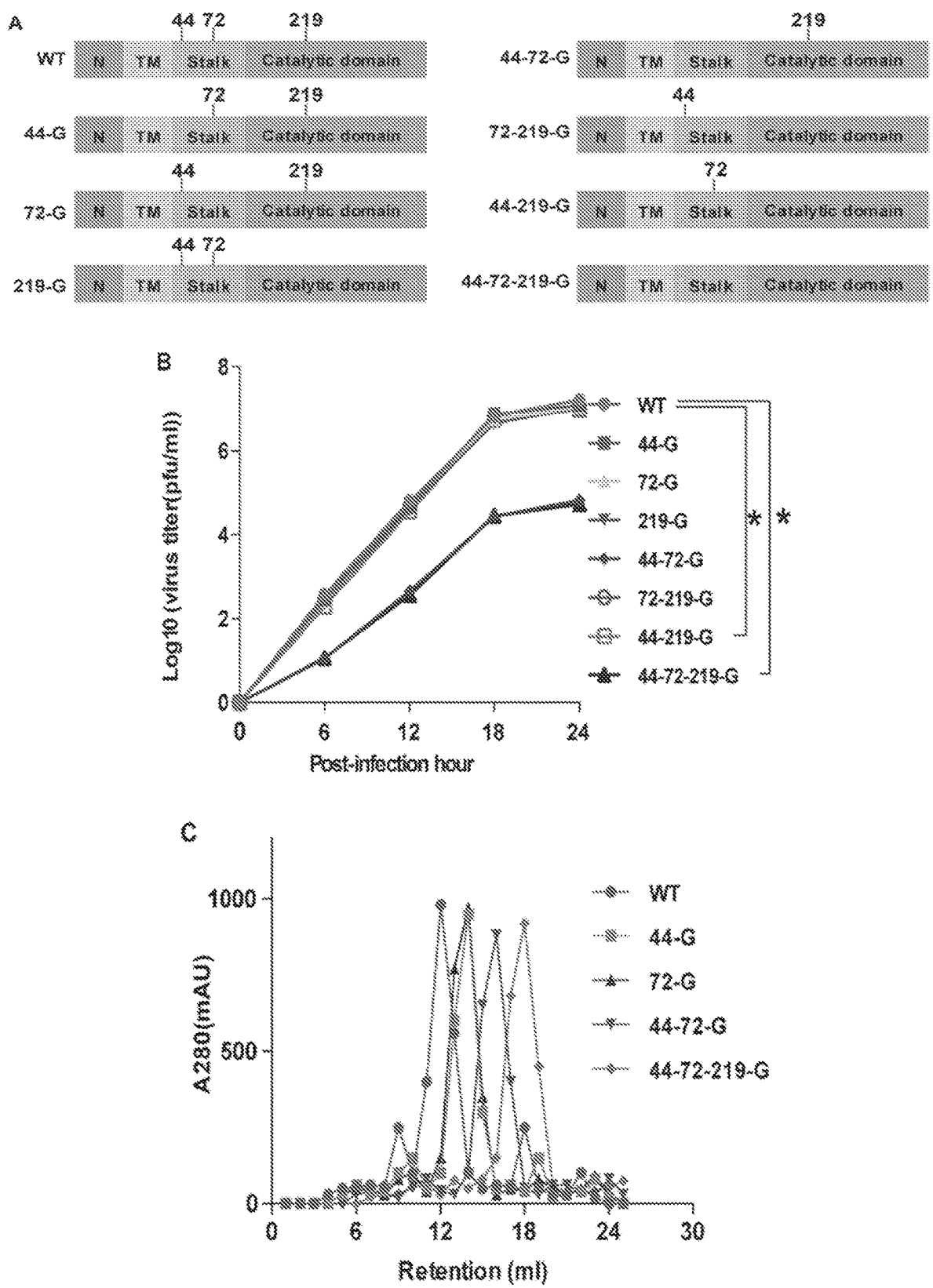
FIG. 7 includes diagrams showing the impact of glycosylation on activity of NA on IAV. (A): a schematic overview of 8 IAVs with different glycosylation patterns on NA. Glycosites are indicated; N indicates N-terminal cytoplasmic domain; TM indicates transmembrane domain. All recombinant viruses were confirmed by genome sequencing. (B): a diagram showing the comparison of virus production in MDCK cells infected with 8 variants of virus as indicated. (C): a diagram showing gel filtration analysis of five types of NA proteins. (D): a diagram showing gel filtration analysis of five types of deglycosylated NA proteins. (E): a photo showing western blot analysis of viruses after treatment with the endoglycosidase cocktail, using an anti-NA antibody. (F): a chart showing measurements of NA activity on deglycosylated IAV by 4-MUNANA assay. In panel B, Mean±SEM for 3 independent experiments is shown; in panel F, Mean±SEM for 5 independent experiments is shown. *: P<0.001.
Figure 7:
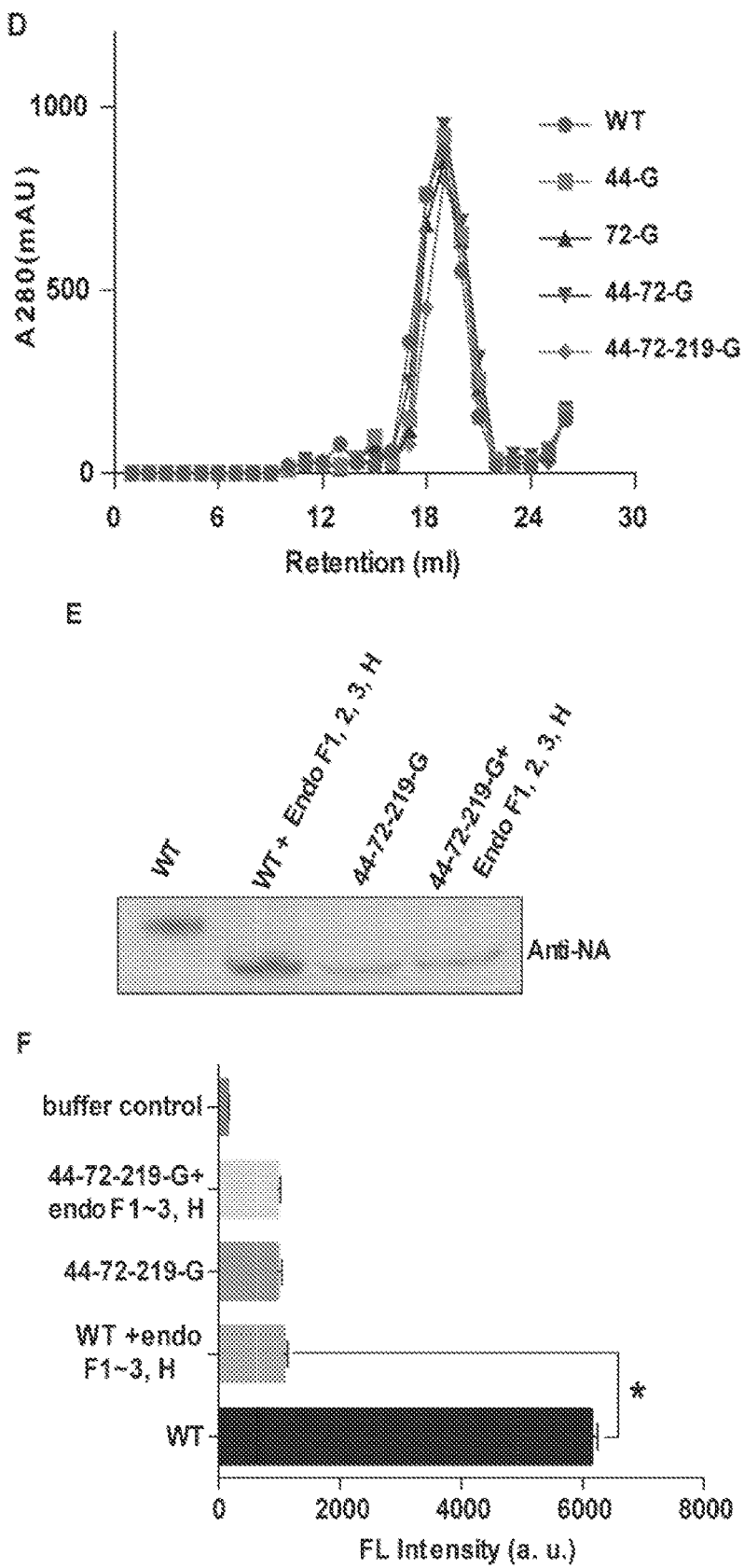

To understand whether NA glycosylation is involved in the lifecycle of IAV, the same virus strain A/WSN/33 was used as a model for investigation of each glycosite by using reverse genetics (FIG. 7, panel A). The amino acid sequences of NA 44-G, NA 72-G, NA 44-72-G and NA 44-72-219-G are provided above as SEQ ID Nos: 8-11 respectively. It was found that glycosites 44 and 72 (in the stalk domain) played an important role in virus replication, and the replication rate of the virus with deleted glycosites 44 and 72 (44-72-G or 44-72-219-G virus) was two orders of magnitude lower than the WT virus in both MDCK and A549 cells (FIG. 2, panel A and FIG. 7, panel B). Glycosites 44, 72 and 219 on NA were glycosylated to form variants of NA proteins with different molecular weights, but these variants showed similar molecular weights after treatment with the endoglycosidase cocktail in Western blot analysis and gel filtration. (FIG. 2, panel B, FIG. 7, panels C-D). Interestingly, the secondary structures of these variants were slightly different, but became the same after de-glycosylation (FIG. 2, panels C-D). These results suggest that the glycans attached to glycosites 44, 72 and 219 are heterogeneous and affect the secondary structures of NA.

Glycosylation at N-44 and N-72 Affected NA Activity and Virulence

The glycans at glycosites 44 and 72 were also found to be important for the NA activity. The viruses without glycosites 44 and 72 (44-72-G and 44-72-219-G) showed significantly lower NA activity than the WT based on an assay using 2-(4-methylumbelliferyl)-α-D-N-acetylneuraminic acid (4-MUNANA) as substrate (FIG. 2, panel E). In addition, after the WT virus was treated with the endoglycosidase cocktail, the molecular weight and NA activity were lower than that of the untreated virus (FIG. 7, panels E-F).

The glycans on NA affected the enzyme activity, affinity and specificity, as the maximum velocity (Vmax) and the affinity value (Km) for different substrates were altered. When 2'(4-meyhylumbelliferyl)-α-D-N-actylneuraminic acid (4-Muα-Neu5Ac), and 6'-sialyl-N-acetyllactosamine (6-SLN) were used as substrates, the NA without glycosites 44 and 72 had lower neuraminidase activity but the Km values of all mutants were similar. Surprisingly, when 3-SLN was used as substrate, the activity of NA with glycosite 44 or 72 deleted decreased about 50%, but the Km value increased more than two-fold (FIG. 3: panel A and Table 1). Interestingly, the virus production rates of these variants in LMH cells were related to the NA activity on 3-SLN, which is an avian receptor (FIG. 3, panel B). These results suggested that glycosylation on NA affected IAV replication in mammal and avian cells differently (FIG. 2, panel A and FIG. 3, panel B).

Figure 8:
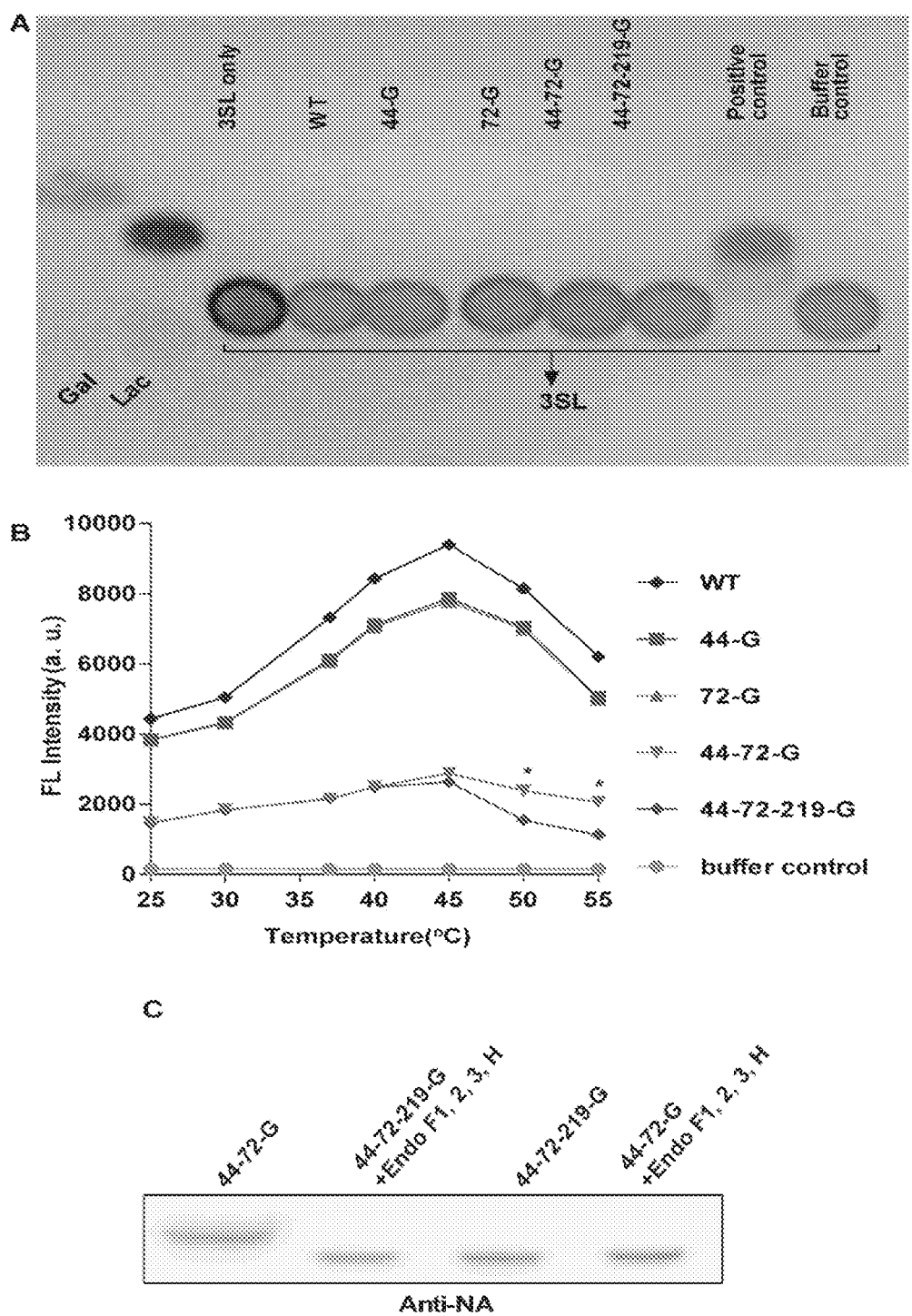
FIG. 8 includes diagrams showing the impact of glycosylation on thermostability of NA and on IAV morphology. (A): a photo showing that indicated WSN NA mutants could not cleave 3-SL. (B): a diagram showing the effect of temperature on NA activity on viruses as indicated, using a 4-MUNANA assay. (C): a photo showing western blot analysis of 44-72-G and 44-72-219-G viruses after treatment with the endoglycosidase cocktail (F1, F2, F3 and H), using an anti-NA antibody. (D): a photo showing morphology of the 44-G NA virus, using transmission electron microscopy. (E): a photo showing morphology of the 72-G virus, using electron microscopy. (F): a photo showing morphology of the 44-72-G virus, using electron microscopy. In panel B, Mean±SEM for 5 independent experiments is shown. *: P<0.001.
Figure 8:
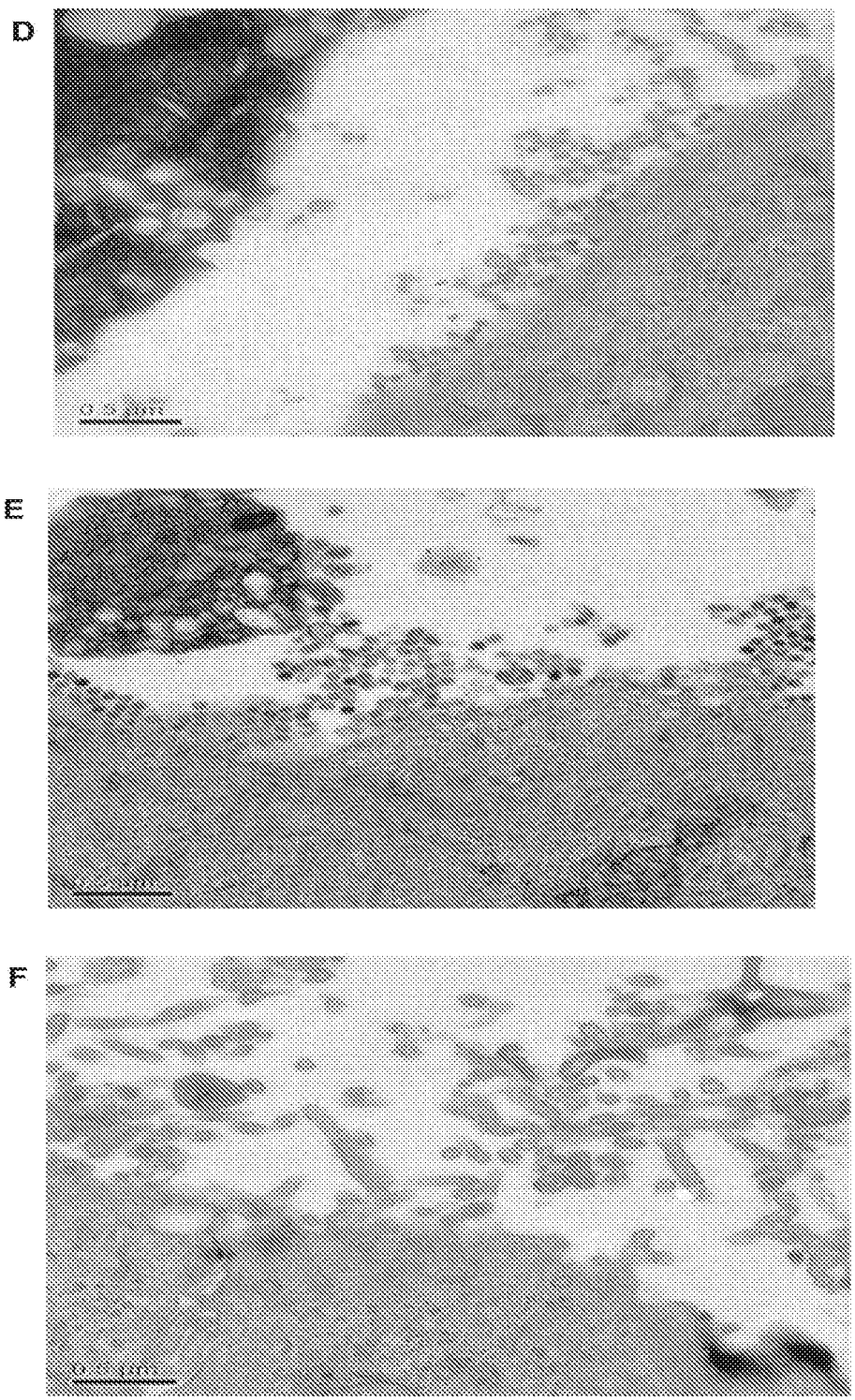

In addition, while the NA without glycosite 72 (72-G) interacted with 6'-sialyllactose (6-SL) as substrate, none of the variants interacted with 3'-sialyllactose (3-SL) (FIG. 3, panel C and FIG. 8, panel A). Interestingly, the activity of 44-72-219-G was similar to that of 44-72-G (with glycosite 219) from 25 to 40° C. but lower at higher temperatures (45, 50 and 55° C.) (FIG. 8, panel B). After 44-72-G was treated with the endoglycosidase cocktail, the activity of NA was lower than that without treatment at 55° C.; these results suggested that glycans on glycosite 219 (in the catalytic domain) affected the thermostability of NA (FIG. 3, panel D and FIG. 8: panel C).

Glycosites 44 and 72 also modulate the virus release and morphogenesis, because the cells infected with WT, 44-G, and 72-G viruses released many more spherical viral particles, but the cells infected with the 44-72-G or the 44-72-219-G virus produced mainly elongated and filamentous shaped particles, which were not observed in the WT virus-infected cells (FIG. 3, panels E-F and FIG. 8, panels D-F). In addition, mice infected with viruses without any glycans on NA (44-72-219-G virus) showed less prominent changes in survival rate and body weight compared with the WT-infected mice, which had a 20% survival rate and considerable loss of body weight. These results suggested that the glycosylation on NA affected virulence (FIG. 3, panels G-H).

Figure 9:
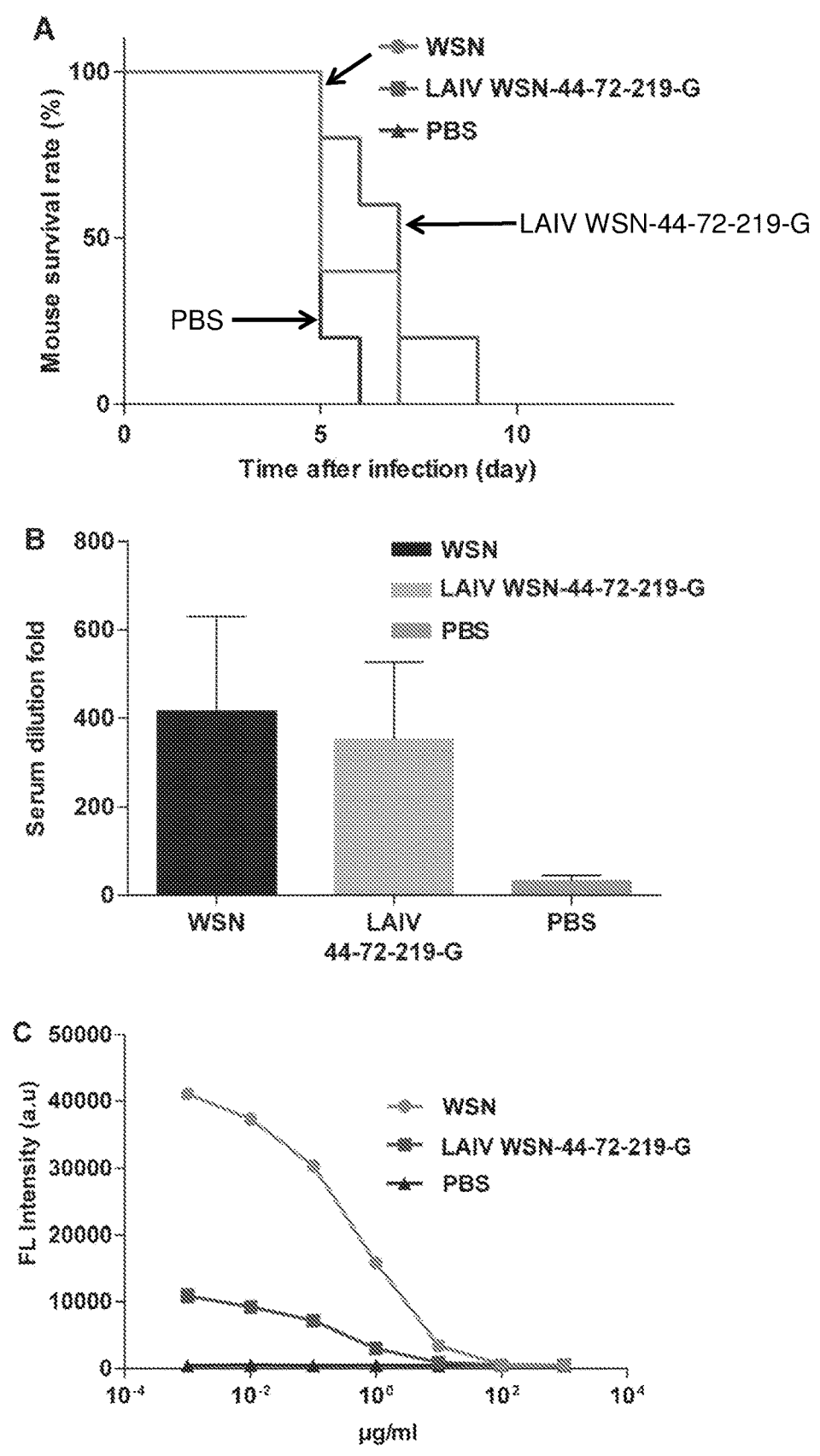

Live Attenuated Vaccine without the Stalk and Catalytic Domains of NA Showed Broad Protection with Strong CD8+ T-Cell Response IAV with non-glycosylated NA (44-72-219-G) was used as a live attenuated influenza vaccine (LAIV WSN-44-72-219-G) to determine the vaccine's prophylactic potential. Non-glycosylated NA was chosen because it had low NA activity and virulence. However, the non-glycosylated NA virus showed a similar immunogenicity as WT (FIG. 9, panels A-C).

Figure 4:
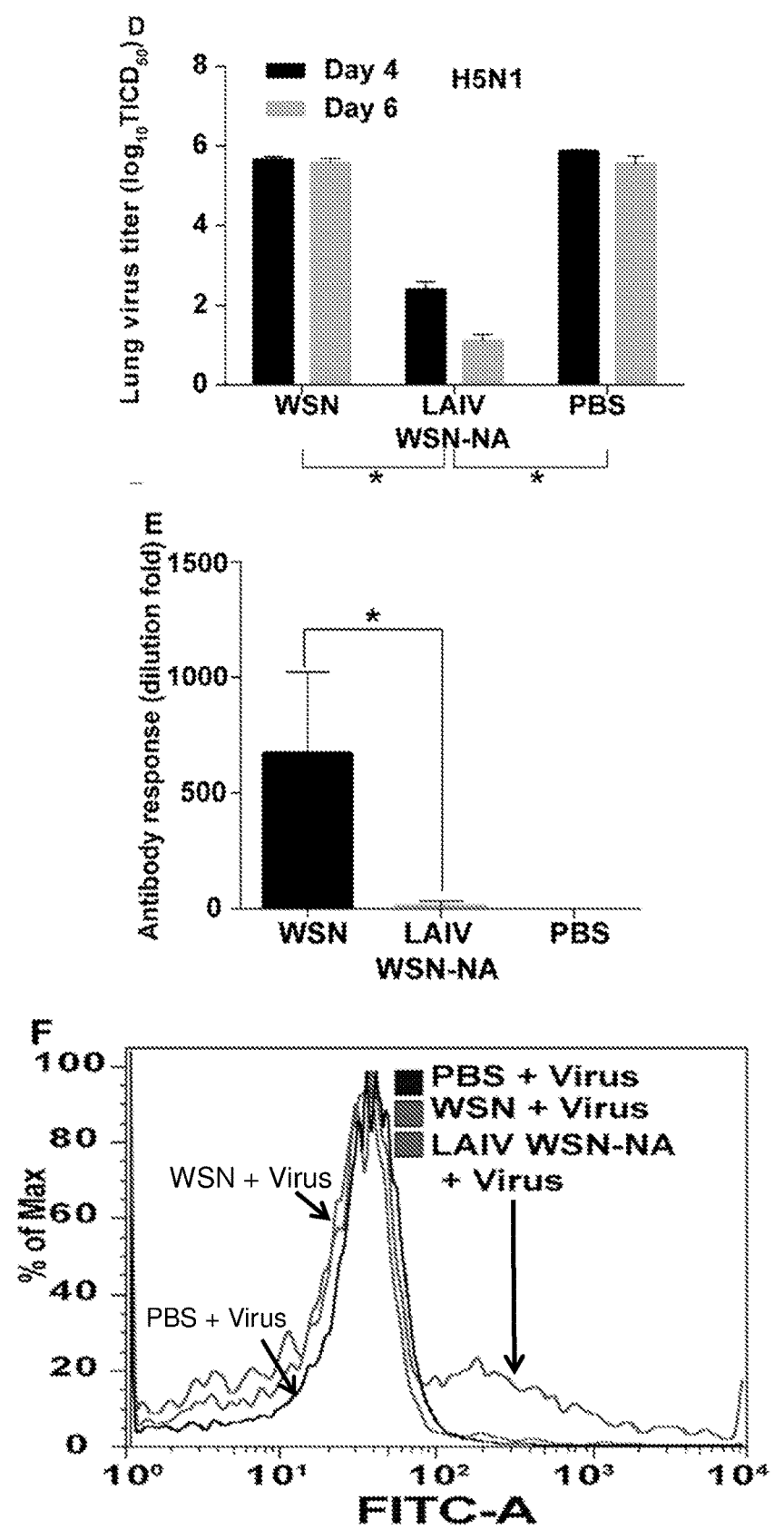
Figure 4:
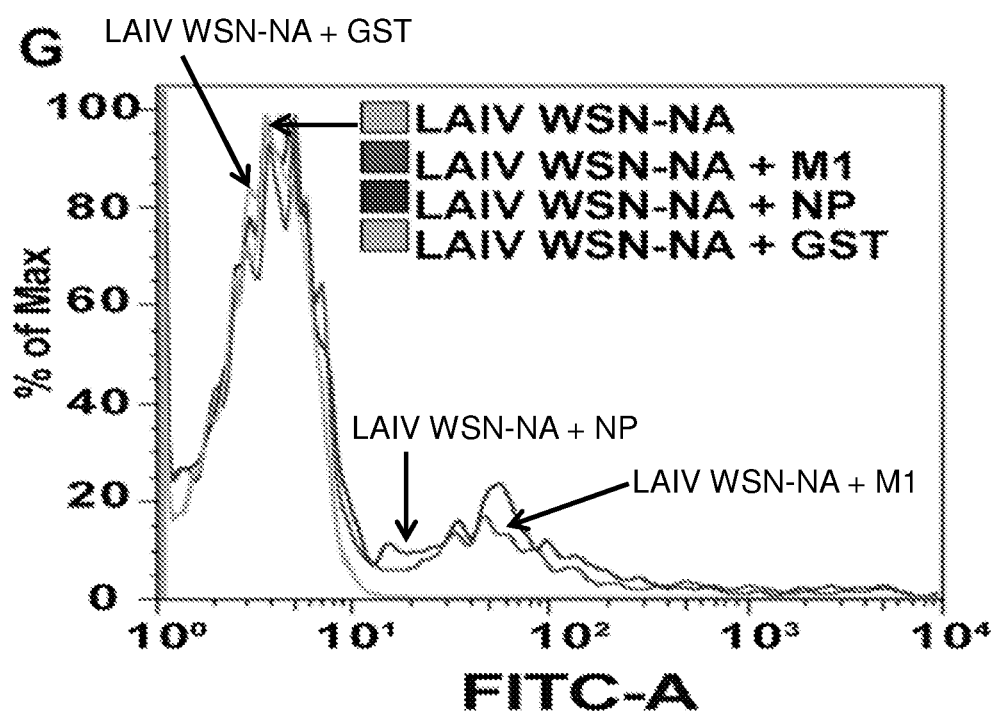
Figure 10:
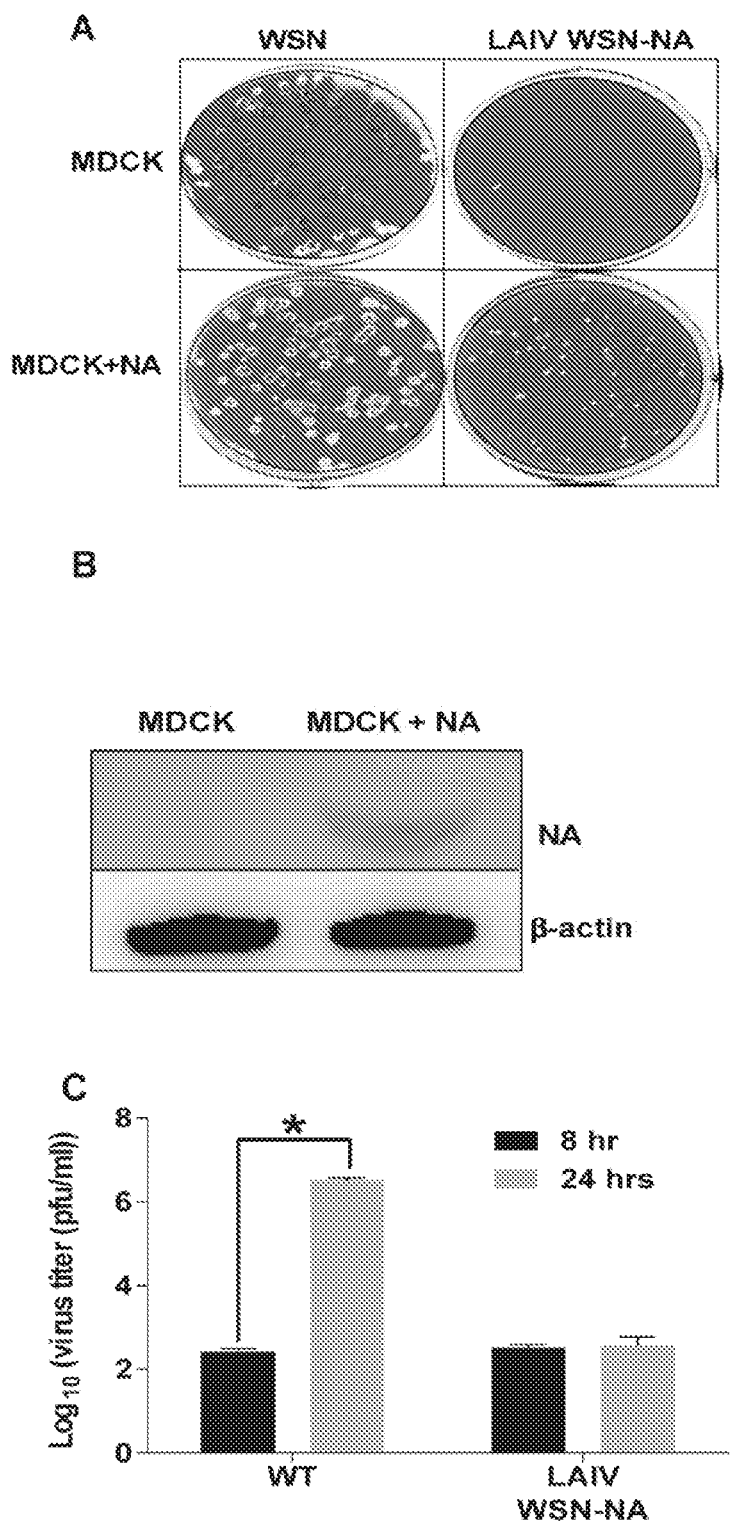
FIG. 10 includes diagrams showing that the LAIV WSN-NA virus is an effective vaccine with low pathogenicity. (A): a diagram showing the comparison of plaque formation by WSN and LAIV WSN-NA virus in WT MDCK and MDCK with NA expression (MDCK+NA). (B): a photo showing western blot analysis of NA expression in MDCK+NA cells, using anti-NA and anti-β-actin antibody. (C): a diagram showing indicated viral titers at indicated times after A549 cells were infected virus at an MOI of 3. (D): a photo showing western blot analysis of intracellular viral M1 protein levels in A549 cells infected with indicated viruses, using an anti-M1 antibody and anti-β-actin antibody. (E): a diagram showing the survival rate of mice infected with WSN or LAIV WSN-NA virus as indicated. (F): is a diagram showing body weight of mice infected with indicated virus over 14 days. In panel C, Mean±SEM for 3 independent experiments is shown. In panel E, 5 independent experiments is shown. In panel F, Mean±SEM for 5 independent experiments is shown. *: P<0.001.
Figure 10:
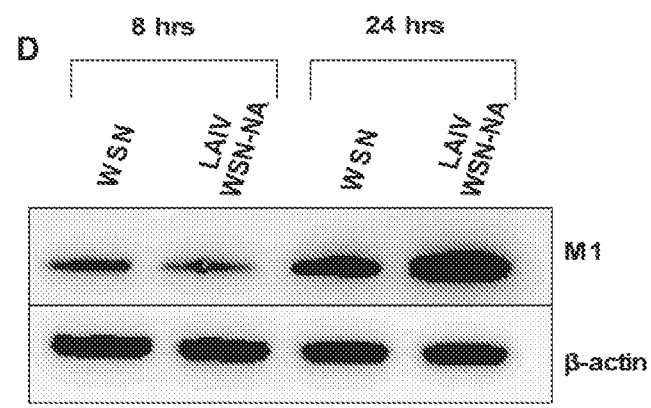
Figure 10:
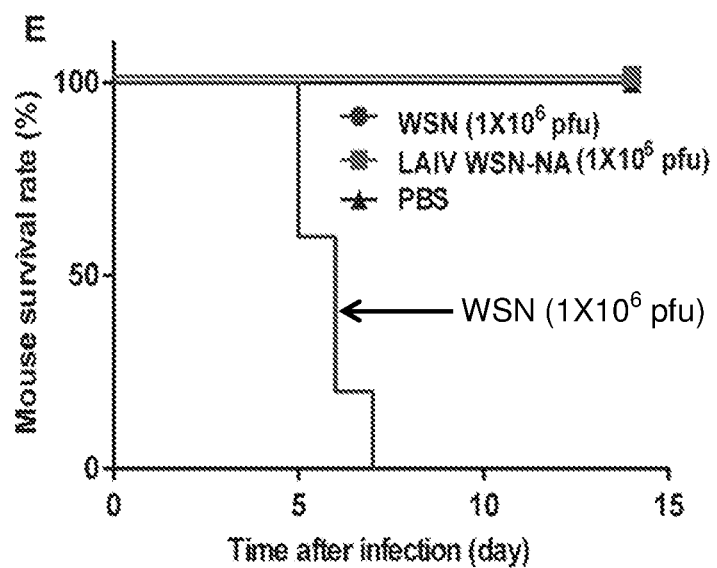
Figure 10:
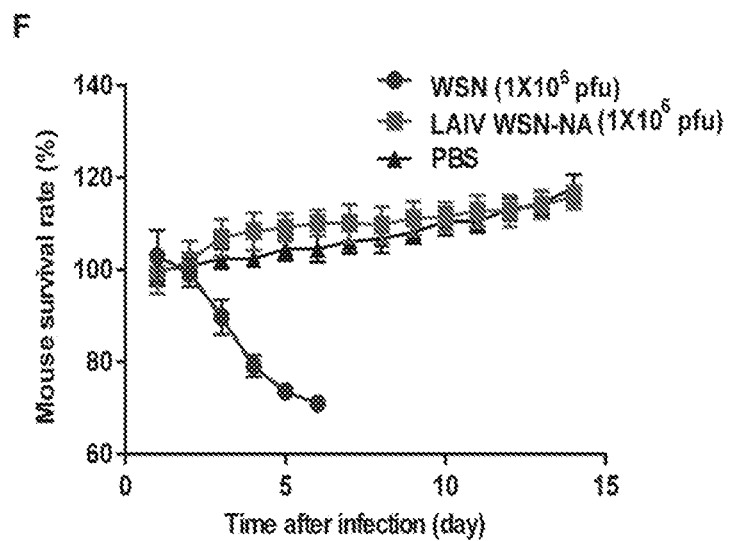
Figure 11:
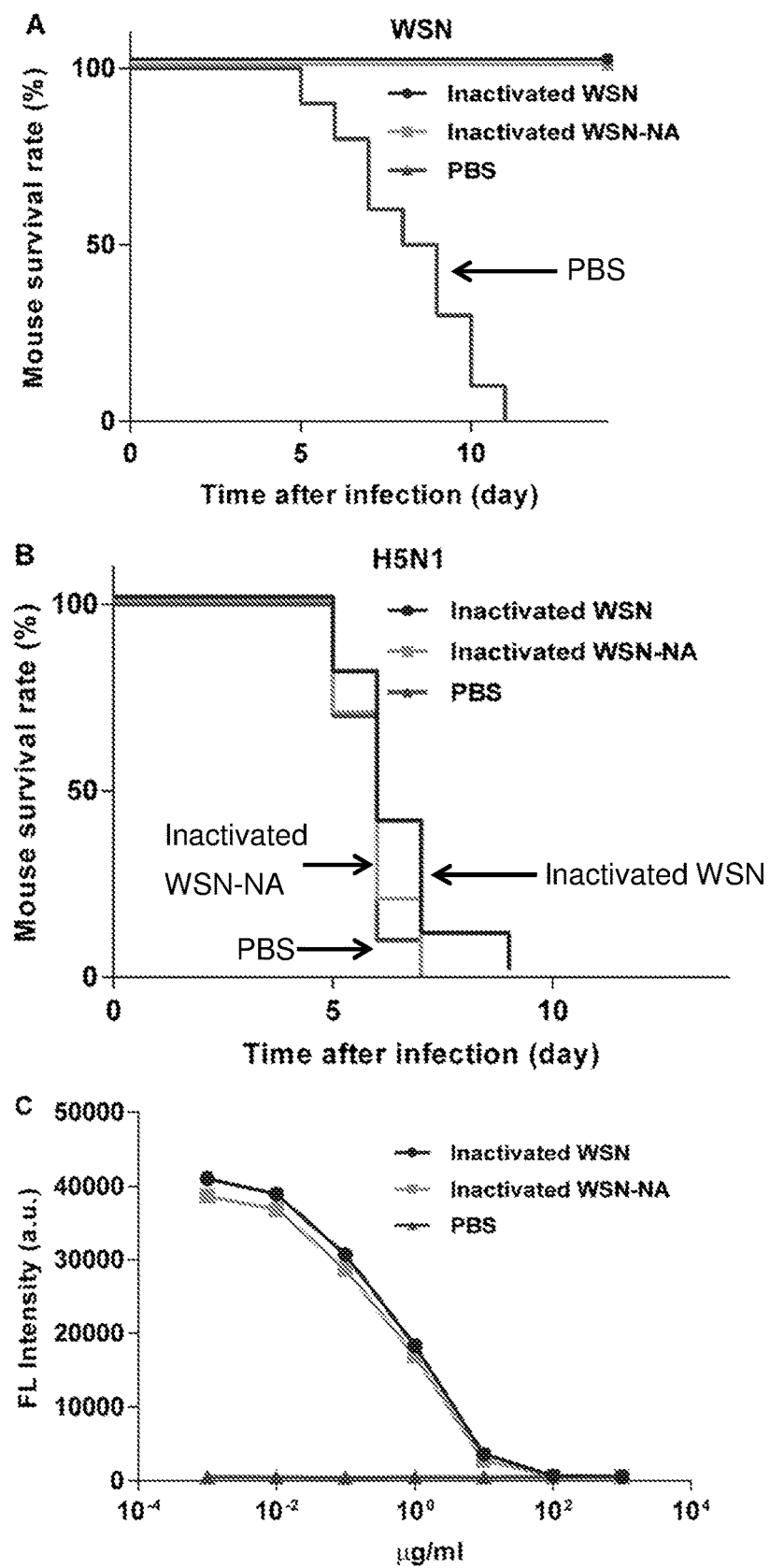
FIG. 11 includes diagrams comparing the host immune response to inactivated WSN and WSN-NA viruses. (A): a chart showing the survival rate of mice immunized with indicated inactivated viruses and subsequently challenged with a lethal dose of WSN virus. (B): a chart showing the survival rate of mice immunized with indicated viruses and subsequently challenged with a lethal dose of H5N1 virus. (C): a chart showing the titer of NA antibody from mice immunized with indicated viruses, using the neuraminidase inhibition assay. IC50 of sera from WSN virus treated mice was 5.2 µg/ml, and WSN-NA virus was 4.7 µg/ml. In panels A and B, 10 independent experiments are shown; in panel C, Mean±SEM for 10 independent experiments is shown.

In addition, the NA activity had no effect on the efficiency of inactive vaccine, and the level of antibody produced was very low. Therefore, a virus was generated without both the stalk and catalytic domains of NA (LAIV WSN-NA) by adding a stop codon to the RNA genome segment of NA to enhance the immunogenicity of NA (FIG. 4, panel A). It was found that LAIV WSN-NA virus did not form the plaque in MDCK cells and could be rescued by expressing WT NA in the cell (FIG. 10, panels A-B). After 24 hpi, the A549 cells infected by LAIV WSN-NA virus showed fewer viruses released into the supernatant and the intracellular viral protein M1 was accumulated; these results suggested that LAIV WSN-NA virus had a defect in virus release (FIG. 10, panels C-D). The body weight of mice infected with 1×10$^6$ PFU of WSN viruses rapidly decreased, and these mice died at 6 days post-infection. On the other hand, the mice infected with 1×106 PFU of LAIV WSN-NA viruses via oral administration survived well and showed no body weight loss; these results indicated that LAIV WSN-NA virus was an effective LAIV with low pathogenicity, and attenuation of viruses in cells was essential for the efficacy of live vaccine (FIG. 10, panels E-F). The immunogenicity of inactivated WSN-NA virus was similar to that of inactivated WSN virus in the immunogenicity test (FIG. 4, panel B and FIG. 11, panels A-C).

Figure 12:
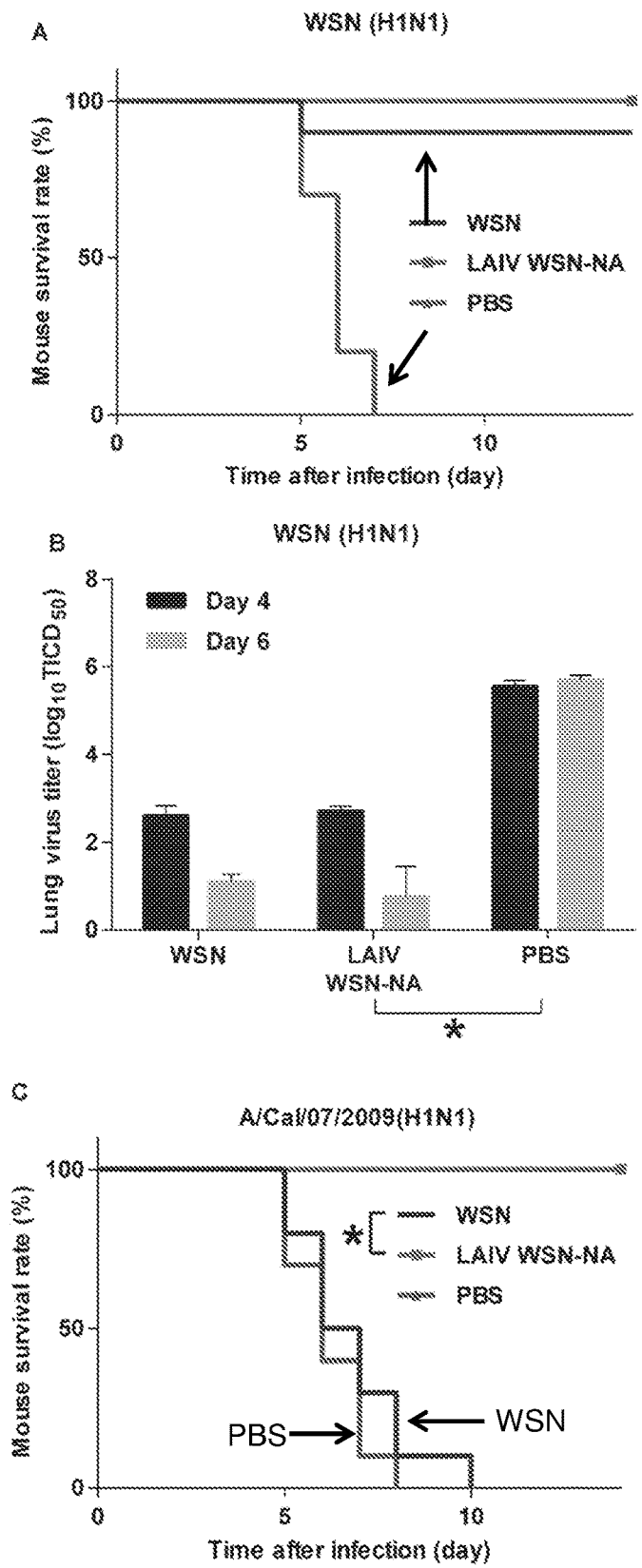
FIG. 12 includes diagrams showing cross-strain protection from LAIV WSN-NA treatment. (A): a chart showing the mouse survival rate after mice were treated with WSN, LAIV WSN-NA or PBS and subsequently challenged with a lethal dose of WSN. (B): a chart showing WSN virus replication kinetics in the lung of mice treated as indicated on day 4 and 6 post-infection. (C): a chart showing the mouse survival rate after mice were treated with WSN, LAIV WSN-NA or PBS and subsequently challenged with a lethal dose of A/cal/07/2009 (H1N1). (D): a chart showing A/cal/07/2009 virus replication kinetics in the lung of mice treated as indicated on day 4 and 6 post-infection. (E): a chart showing the relationship between the dose of LAIV WSN-NA treatment and mouse survival rate after H5N1 and WSN challenge. (F): a chart showing the impact of inactivated WSN virus on INF-γ expression in CD8+ T cells from live WSN-, LAIV WSN-NA- and PBS-treated mice, using flow cytometry. (G): a photo showing western blot analysis of granzyme B expression incubation of CD8+ cells from mice immunized with LAIV WSN-NA with live WSN virus (+virus), NP (+NP) or M1 (+M1) epitope, using anti-granzyme B and anti-β-actin antibodies. In panels A, C, and E, 10 independent experiments are shown. In panels B, D, Mean±SEM of 3 independent experiments is shown. F, Data are representative of three similar experiments. *: P<0.001.
Figure 12:
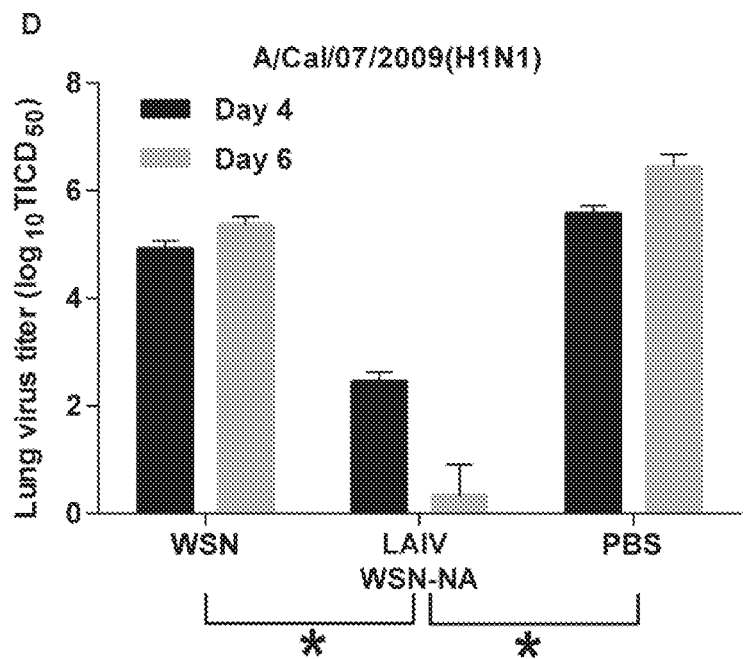
Figure 12:
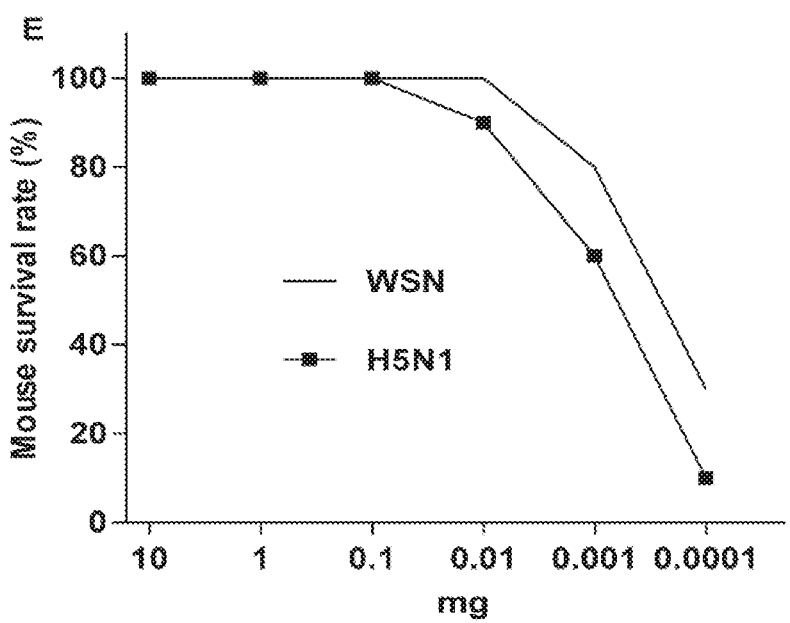
Figure 12:
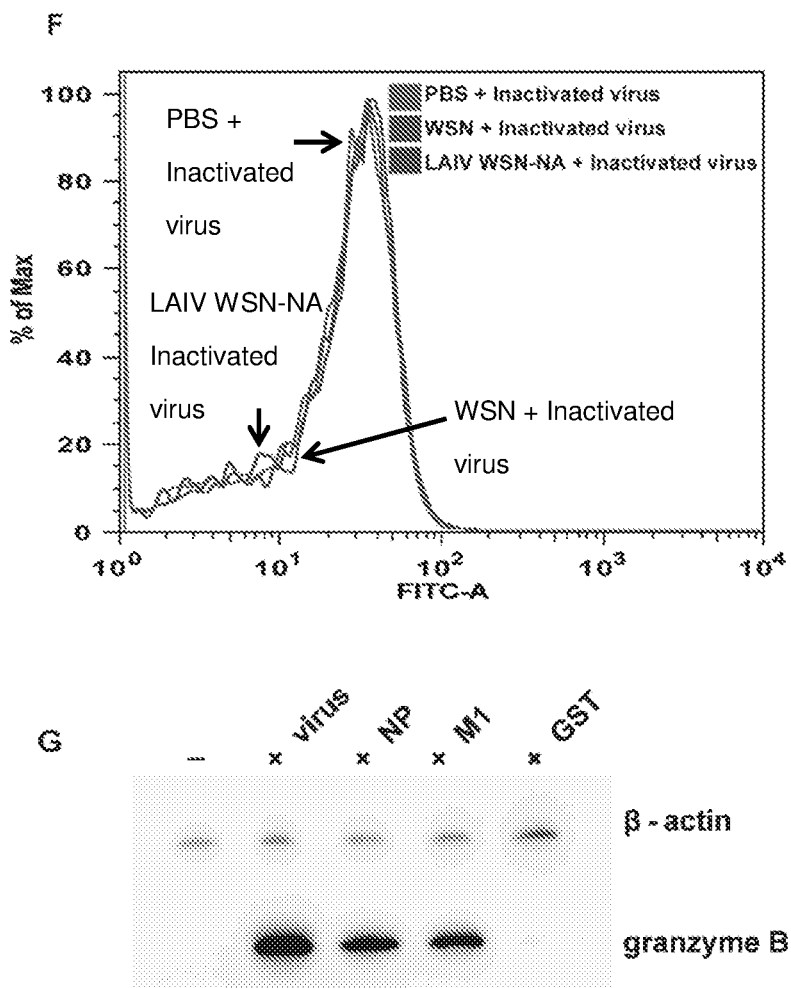

However, when LAIV WSN-NA virus was used as vaccine, it showed cross-strain and cross-subtype protection against WSN, A/Cal/07/2009 and H5N1 in the virus challenge study; the LAIV WSN-NA-treated mice survived well and cleared viruses from the lung, but did not induce any notable antibody response (FIG. 4: panels C-E and FIG. 12, panels A-D). In addition, the protective ability of LAIV WSN-NA also showed a dose-dependent response (FIG. 12: panel E). After the virus infected the peripheral blood mononuclear cells (PBMC) from LAIV WSN-NA-treated mice, CD8+ T cells were specifically activated via IFN-γ and granzyme B expression, but the inactive virus did not show this activity, suggesting that LAIV WSN-NA can induce CD8+ T-cell activation upon virus infection (FIG. 4, panel E and FIG. 12, panels F-G). Furthermore, the highly conserved viral epitopes NP and M1 also stimulated CD8+ T cell activation (FIG. 4, panel G and FIG. 12, panel G). These results suggested that NA plays a key role in regulating the host immune response via CD8+ T-cell activation and LAIV WSN-NA was an effective vaccine.

Finally, it was observed that the one glycosite on M2 did not affect virus replication (FIG. 13).

Several studies have suggested that diversification in the stalk domain of NA is associated with the virulence and transmission of IAV from ducks to land-based poultry, and its spread among humans via evolutionary processes, including sequence deletion and glycosite modification. However, the structural and functional roles of the stalk domain of NA were unknown thus far, and there was no report about the glycosylation of these canonical glycosites. Results from this example indicated that glycosites in the stalk domain of NA are glycosylated to regulate the activity, affinity and specificity of NA to modulate IAV replication, suggesting that the glycans in the stalk domain of NA play an important role in the virulence and transmission of IAV.

Example 3: Identification of Immunogenic NA Variants on IAV with Low Virulence Materials and Methods
Generation of Recombinant Viruses Site directed mutagenesis was used to generate NA variants described herein. To generate an NA variant having the catalytic domain deleted (WSN-NA-CD, SEQ ID NO: 15 provided above), a stop codon was used in place of the first

TABLE 1

Km and Vmax of NA proteins and viral variants.

| Protein | WT | 44-G | 72-G | 44-72-G | 44-72-219-G | unit |
|---|---|---|---|---|---|---|
| For 4-Muα-Neu5Ac | | | | | | |
| Vmax | 5.025 | 4.95 | 4.45 | 1.15 | 1.2 | nM/s |
| Kcat | 514.3 | 468.5 | 426.8 | 100.3 | 105.8 | /s |
| Km | 585.4 | 595.2 | 591 | 588.1 | 596.7 | μM |
| For 3SLN | | | | | | |
| Vmax | 7.04 | 4.09 | 3.89 | 1.46 | 1.48 | nM/s |
| Kcat | 688.2 | 389.8 | 364.4 | 136.4 | 139.1 | /s |
| Km | 125.3 | 295.2 | 288.7 | 296.3 | 299.1 | μM |
| For 6SLN | | | | | | |
| Vmax | 1.07 | 0.92 | 0.85 | 0.24 | 0.21 | nM/s |
| Kcat | 104.2 | 90.6 | 83.6 | 19.8 | 20.7 | /s |
| Km | 678.7 | 684 | 688 | 679 | 675 | μM |

| Virus | WT | 44-G | 72-G | 44-72-G | 44-72-219-G | unit |
|---|---|---|---|---|---|---|
| For 4-Muα-Neu5Ac | | | | | | |
| Specific | 9.7 | 7.78 | 7.34 | 2.3 | 2.42 | nmol/sec/mg |
| Km | 487 | 508 | 485 | 429 | 415 | μM |
| For 3SLN | | | | | | |
| Specific | 14.9 | 9 | 8.35 | 2.92 | 2.96 | nmol/sec/mg |
| Km | 115 | 274 | 268 | 285 | 281 | μM |
| For 6SLN | | | | | | |
| Specific | 2.25 | 1.88 | 1.78 | 0.48 | 0.42 | nmol/sec/mg |
| Km | 534 | 525 | 540 | 521 | 515 | μM |

Km and Vmax in the upper panal were from NA proteins and those in the bottom panel were from viral variants.

codon in the NA catalytic domain. A variant having active site 1 inactivated (WSN-NA-AS1, SEQ No: 12 provided above) was constructed by changing 8102 to A. A variant having Active site 2 inactivated (WSN-NA-AS2, SEQ ID NO: 13 provided above) was constructed by changing D135 to A. Variant WSN-NA G388A (SEQ ID NO: 14 provided above) was constructed by replacing amino acid residue G388 with A388.

Mice Treatment with LAIV WSN-44-72-219-G, LAIV WSN-NA and WSN-NA-AS1

LAIV WSN-NA and WSN-NA-AS1 virus were cultured in MDCK cells with NA expression. A total of 25 μL of LAIV WSN-44-72-219-G, LAIV WSN-NA and WSN-NA-AS1 and nonlethal dose for WT WSN were introduced into each nostril on days 0 and 21 while the mouse was conscious and the virus did not reach the lower respiratory tract. Then, the immunogenicity test procedure was performed.

Virulence Assay

Figure 15:
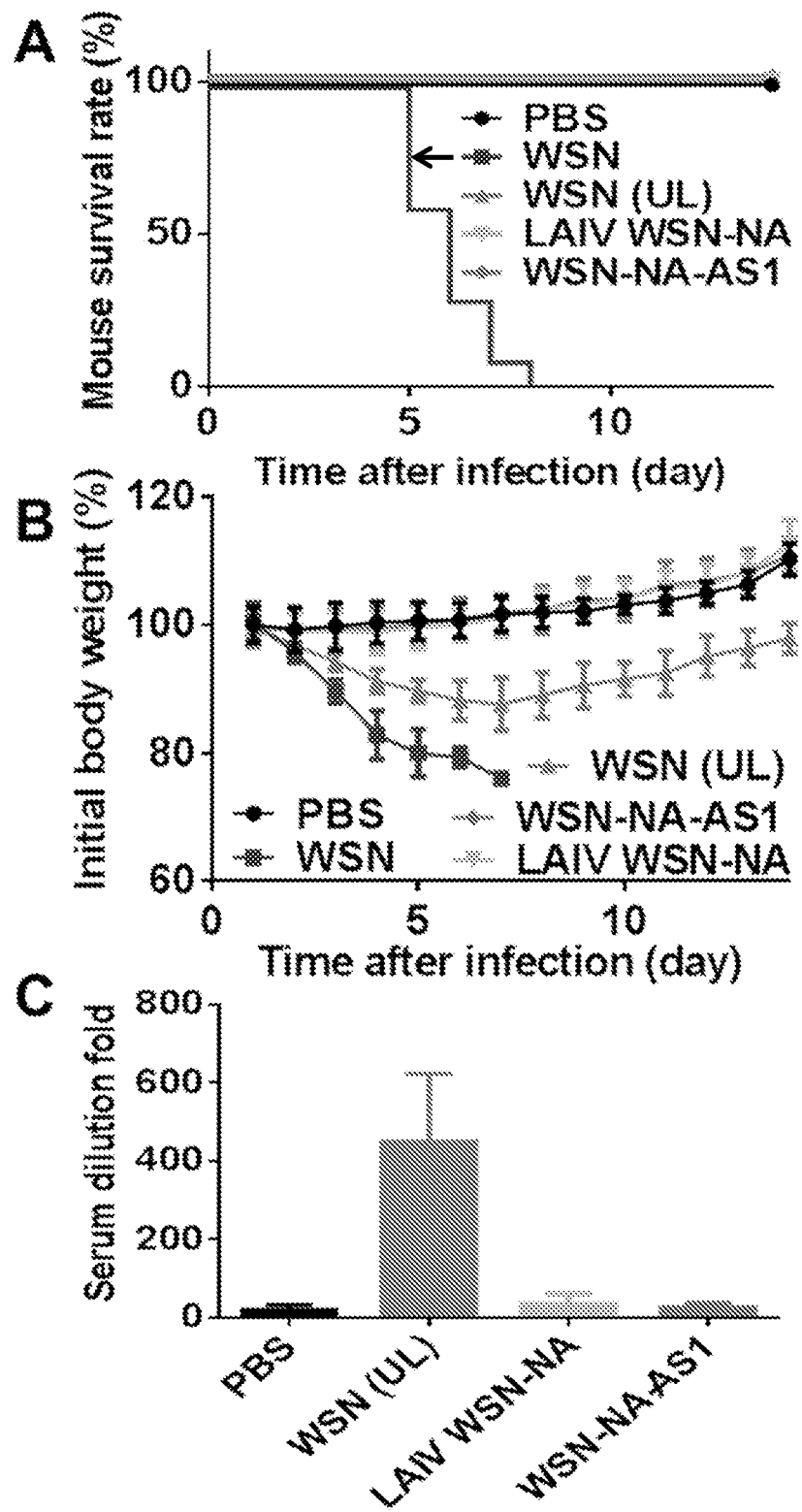
FIG. 15 includes diagrams comparing the host immune response with LAIV WSN-NA and WSN-NA-AS1. After mice were infected with 1×10⁶ pfu of WSN, LAIV WSN-NA, WSN-NA-AS1 or unlethal dosage of WSN (WSN (UL)) viruses, survival rate (A) and body weight (B) were recorded for 14 days. (C) The sera of the treated mice were analyzed using hemagglutination inhibition assay. (D) Virus replication kinetics in the lung of the mice treated by different IAV constructs as indicated at day 4 after infection. (E) Analysis of the survival rate of WSN (UL), LAIV WSN-NA, WSN-NA-AS1 or PBS treatment mice after challenge with a lethal dose of H5N1. (A, B and E) Ten independent experiments are shown. (C and D) Three independent experiments are shown.
Figure 15:
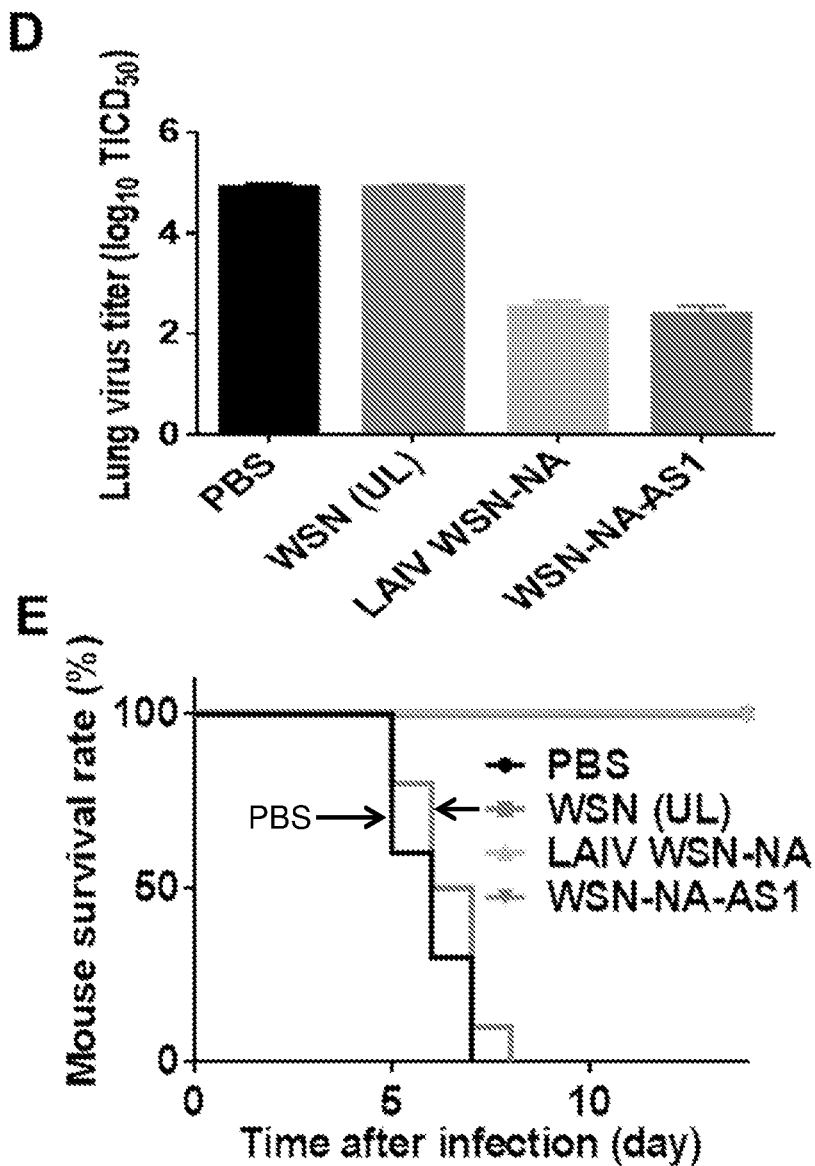

The virulence of recombinant viruses was measured using groups of five female 4- to 6-wk-old BALB/c mice that were intranasally inoculated with 50 μL of virus ($1 \times 10^6$ PFU for WSN, LAIV WSN-NA and WSN-NA-AS1 in FIG. 15, panel A). Survival and body weight changes were recorded daily for 14 d after infection.

Results

Figure 14:
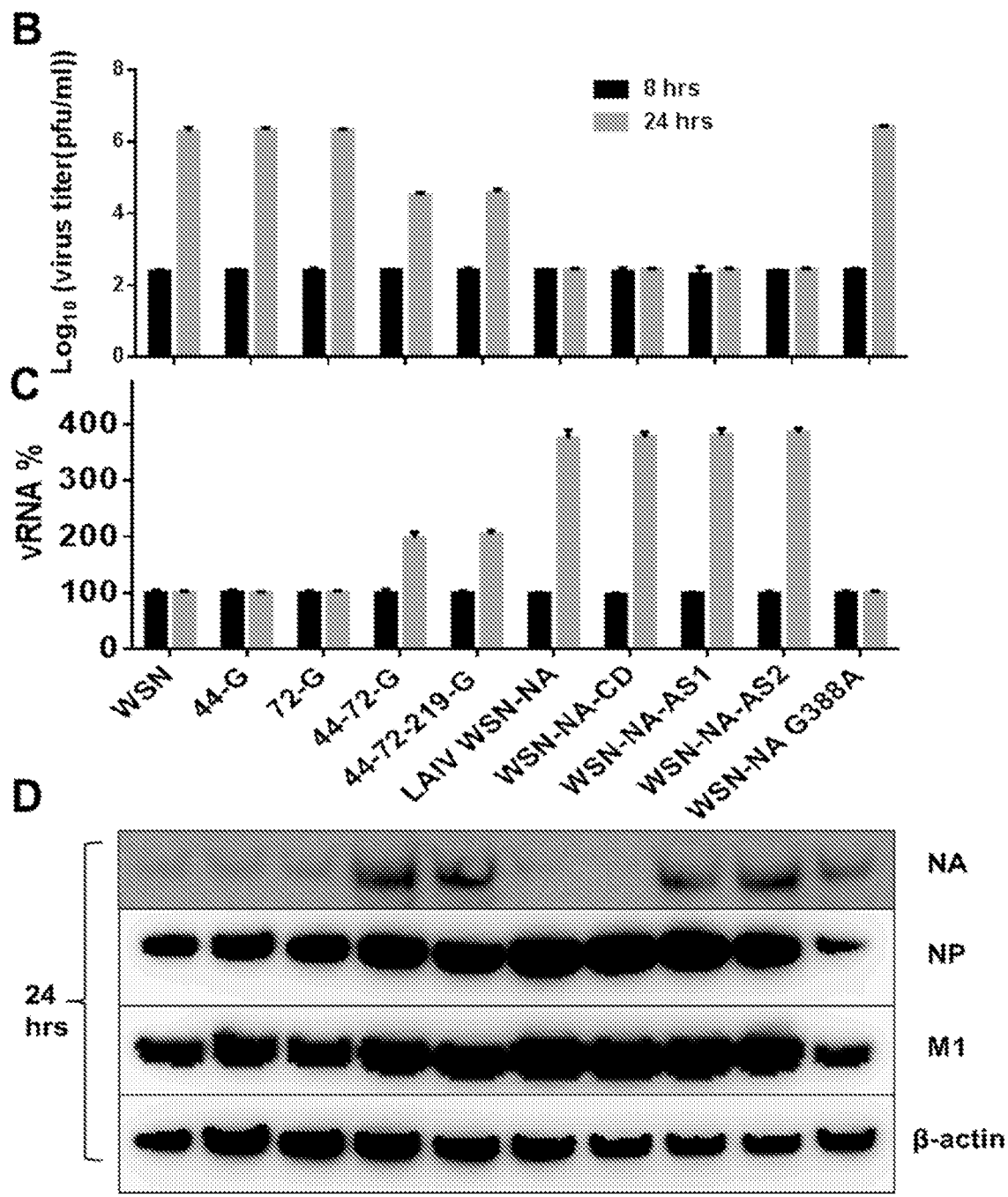
FIG. 14 includes diagrams showing the impact of NA activity on virus release. (A): a schematic overviews of ten IAVs with different modifications on NA. Glycosites are indicated; AS1 construct contains a R102A mutation, which inactivates activity site 1; AS2 construct contains a D135A mutation, which inactivates activity site 2; N indicates N-terminal cytoplasmic domain; TM indicates transmembrane domain. All recombinant viruses were confirmed by genome sequencing. (B): a diagram showing viral titers of A549 cells after infection with indicated virus variants at a MOI of 3. Culture fluids were collected 8 and 24 hours post infection. (C): a chart showing intracellular viral RNA from total cell lysates of A549 cells infected as in panel B. (D): a photo showing western blot analysis of NA, N and M1 protein levels from total cell lysates of A549 cells infected as in panel B, using anti-NA, anti-NP, anti-M1 and anti-β-actin antibodies. In panels B and C, Mean±SEM for three independent experiments.

Various NA variants noted above were generated to determine which regions of the stalk and catalytic domain affected immunogenicity and virulence (FIG. 14, panel A). When A549 cells were infected with NA activity-defected viruses (LAIV WSN-NA, WSN-NA-CD, WSN-NA-AS1 and WSN-NA-AS2), fewer viruses were released into the supernatant, and the intracellular viral RNA (vRNA) and viral proteins (NP and MD accumulated in the cells, suggesting that NA activity, but not the protein itself, is the key for virus release (FIG. 14: panels B-D). Since NA activity plays an important role of virus release, the NA active site mutant virus (WSN-NA-AS1) was used as live attenuated influenza vaccine (LAIV) to compare its immunogenicity with LAIV WSN-NA. The survival rate and body weight over time of mice infected with WSN-NA-AS1 virus via oral administration were similar to that of mice infected with LAIV WSN-NA or PBS (FIG. 15: panels A-B). Similar to LAIV WSN-NA, vaccination with WSN-NA-AS1 also did not induce any notable antibody response (FIG. 15, panel C) and the replication rate of WSN-NA-AS1 virus was comparable to that of LAIV WSN-NA (FIG. 15, panel D). Despite the decrease in virulence of WSN-NA-AS1 virus compared to an unlethal dosage of WSN (FIG. 15, panels C and D), exposure to WSN-NA-AS1 virus protected mice from a lethal dose of H5N1 (FIG. 15, panel E).

These results from WSN-NA-AS1 variant were similar as those of LAIV WSN-NA (see Example 2 above), suggesting that NA activity would affect the host immune responses. Since viral proteins exposed on IAV vaccines would be an important way to induce IAV-specific CD8+ T cell, IAV carrying NA variants with defective enzymatic activity would be expected to have the ability of cross-subtype protection, for example, conferring protection to both H1N1 and H5N1 IAV strains.

Expression of the conserved regions of IAV proteins by using viral vector systems can induce CD8+ T cells against lethal IAV challenge in animals. However, such approaches could only elicit immune responses specific to one target. Alternatively, it was reported to use a mixture of MVA-NP and M1 for making influenza virus vaccine compositions. As disclosed herein, IAV particles comprising defective NA, e.g., truncated versions having no stalk and catalytic domains, significantly induced IAV-specific CD8+ T cells that recognize various strains and different subtypes of IAV in the absence of neutralizing antibodies. These results indicate that the IAVs provided here would be a promising approach for making universal influenza vaccine compositions.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A recombinant Influenza A virus (IAV), comprising: a mutant neuraminidase (NA), which, as compared with its wild-type counterpart, (a) comprises a substitution at a position corresponding to residue 102 or 135 in SEQ ID NO:4, or (b) consists of the amino acid sequence of SEQ ID NO:2; wherein the mutant NA is defective in neuraminidase activity.

2. The recombinant IAV of claim 1, wherein the mutant NA comprises the substitution at the position corresponding to residue 102 or 135 in SEQ ID NO:4.

3. The recombinant IAV of claim 2, wherein the mutant NA comprises an amino acid sequence at least 85% identical to SEQ ID NO: 4.

4. The recombinant IAV of claim 1, wherein the mutant NA consists of the amino acid sequence of SEQ ID NO:2.

5. An immunogenic composition, comprising the recombinant Influenza A virus (IAV) of claim 1, and a pharmaceutically acceptable carrier.

6. The immunogenic composition of claim 5, wherein the pharmaceutically acceptable carrier is an adjuvant.

7. A method for inducing immune responses against influenza A virus in a subject, the method comprising administering to a subject in need thereof an effective amount of the immunogenic composition of claim 5.

8. The method of claim 7, wherein the subject is a human subject.

9. The method of claim 8, wherein the human subject is infected, suspected of being infected, or at risk for infection by an influenza A virus.

10. The method of claim 9, wherein the influenza A virus is an H1N1 or H5N1 influenza A virus.

11. The method of claim 7, wherein the immunogenic composition is administered to the subject via a route selected from the group consisting of oral administration, enteral administration, nasal administration, topical administration, and transmucosal administration.

12. The method of claim 7, wherein the immunogenic composition is administered to the subject parenterally.

* * * * *